United States Patent
Arimori et al.

(10) Patent No.: US 9,675,072 B2
(45) Date of Patent: *Jun. 13, 2017

(54) TETRAZOLINONE COMPOUND AND APPLICATION OF SAME

(71) Applicant: SUMITOMO CHEMICAL COMPANY, LIMITED, Tokyo (JP)

(72) Inventors: Sadayuki Arimori, Takarazuka (JP); Nao Maehata, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/787,836

(22) PCT Filed: May 26, 2014

(86) PCT No.: PCT/JP2014/064556
§ 371 (c)(1),
(2) Date: Oct. 29, 2015

(87) PCT Pub. No.: WO2014/192953
PCT Pub. Date: Dec. 4, 2014

(65) Prior Publication Data
US 2016/0081340 A1    Mar. 24, 2016

(30) Foreign Application Priority Data

May 29, 2013   (JP) .................................. 2013-112702
Jul. 3, 2013   (JP) .................................. 2013-139492
Oct. 2, 2013   (JP) .................................. 2013-207035

(51) Int. Cl.
*A01N 43/713* (2006.01)
*C07D 403/12* (2006.01)

(52) U.S. Cl.
CPC ......... *A01N 43/713* (2013.01); *C07D 403/12* (2013.01)

(58) Field of Classification Search
None
See application file for complete search history.

(56) References Cited

U.S. PATENT DOCUMENTS

| 6,583,090 B1 | 6/2003 | Gewehr et al. |
| 2015/0031733 A1 | 1/2015 | Yoshimoto et al. |
| 2015/0051171 A1 | 2/2015 | Yoshimoto et al. |
| 2015/0299146 A1 | 10/2015 | Hasegawa et al. |
| 2015/0336908 A1 | 11/2015 | Shioda et al. |

FOREIGN PATENT DOCUMENTS

| JP | 2002-506060 A | 2/2002 |
| WO | WO 97/05115 A1 | 2/1997 |
| WO | WO 2013/162072 A1 | 10/2013 |
| WO | WO 2013/162077 A1 | 10/2013 |
| WO | WO 2014/051161 A1 | 4/2014 |
| WO | WO 2014/051165 A1 | 4/2014 |
| WO | WO 2014/084223 A1 | 6/2014 |
| WO | WO 2014/104268 A1 | 7/2014 |
| WO | WO 2014/104382 A1 | 7/2014 |
| WO | WO 2014/104384 A1 | 7/2014 |
| WO | WO 2014/175465 A1 | 10/2014 |
| WO | WO 2015/005499 A1 | 1/2015 |
| WO | WO 2015/016335 A1 | 2/2015 |
| WO | WO 2015/016372 A1 | 2/2015 |
| WO | WO 2015/016373 A1 | 2/2015 |
| WO | WO 2015/030217 A1 | 3/2015 |
| WO | WO 2015/041360 A1 | 3/2015 |
| WO | WO 2015/046480 A1 | 4/2015 |
| WO | WO 2015/056806 A1 | 4/2015 |
| WO | WO 2015/060461 A1 | 4/2015 |

OTHER PUBLICATIONS

International Search Report, issued in PCT/JP2014/064556, dated Sep. 2, 2014.
First Office Action (including an English translation thereof) issued in the corresponding Chinese Patent Application No. 201480030222.6 on Jun. 8, 2016.
Chinese Office Action, dated Dec. 30, 2016, for Chinese Application No. 201480030222.6, with English translation of the Chinese Office Action.

*Primary Examiner* — Alicia L Otton
(74) *Attorney, Agent, or Firm* — Birch, Stewart, Kolasch & Birch, LLP

(57) ABSTRACT

A tetrazolinone compound represented by formula (1):

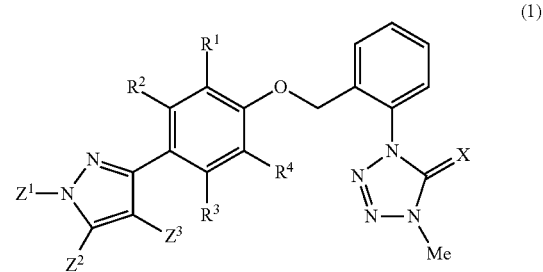

wherein $R^1$ represents a C1-C3 alkyl group optionally having a fluorine atom, etc.; $R^2$ and $R^4$ represents a hydrogen atom, etc.; $R^3$ represents a hydrogen atom, etc.; $Z^1$ represents a C1-C3 alkyl group optionally having a halogen atom, etc.; $Z^2$ represents a C1-C3 alkoxy group optionally having a halogen atom, a C3-C4 alkynyloxy group, etc.; $Z^3$ represents a hydrogen atom, a C1-C3 alkyl group optionally having a halogen atom, etc.; and X represents an oxygen atom, etc., has excellent control activity against pests.

5 Claims, No Drawings

TETRAZOLINONE COMPOUND AND APPLICATION OF SAME

TECHNICAL FIELD

The present invention relates to tetrazolinone compounds and applications thereof.

BACKGROUND ART

Heretofore, various chemicals have been developed so as to control pests and provides in practice use, but in some cases, these chemicals may not exert enough activity.

Meanwhile, there have been known, as pest control agents having a tetrazolinone ring, 1-{2-[2-methyl-4-(1,5-dimethyl-1H-pyrazol-3-yl)phenoxymethyl]phenyl}-4-methyl-1,4-dihydrotetrazol-5-one (A) and 1-{2-[2-methyl-4-(4-chloro-1,5-dimethyl-1H-pyrazol-3-yl)phenoxymethyl]phenyl}-4-methyl-1,4-dihydrotetrazol-5-one (B) represented by formula (A) and formula (B) shown below (see WO 99/046246 A).

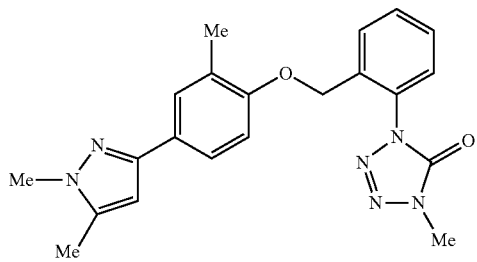

(A)

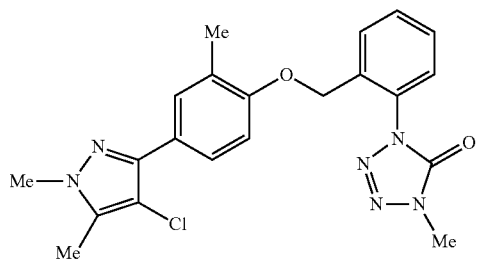

(B)

The present invention provides compounds having excellent control activity against pests.

DISCLOSURE OF THE INVENTION

The present inventors have intensively studied so as to find compounds having excellent control activity against pests and found that the below-mentioned tetrazolinone compound represented by formula (1) have excellent control activity against pests, thus completing the present invention.

Specifically, the present invention includes the following [1] to [6].

[1] A tetrazolinone compound represented by formula (1):

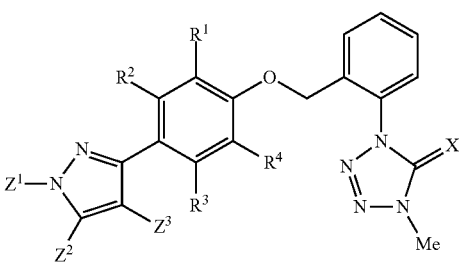

(1)

wherein
$R^1$ represents a C1-C3 alkyl group optionally having a fluorine atom, or a halogen atom;
$R^2$ and $R^4$ each independently represents a hydrogen atom or a fluorine atom;
$R^3$ represents a hydrogen atom, a C1-C3 alkyl group, or a halogen atom;
$Z^1$ represents a C1-C3 alkyl group optionally having a halogen atom;
$Z^2$ represents a C1-C3 alkoxy group optionally having a halogen atom, a C3-C4 alkynyloxy group optionally having a halogen atom, a C1-C3 alkylthio group optionally having a halogen atom, a C2-C4 dialkylamino group, or a cyano group;
$Z^3$ represents a hydrogen atom, a C1-C3 alkyl group optionally having a halogen atom, a halogen atom, or a cyano group; and
X represents an oxygen atom or a sulfur atom.

[2] The tetrazolinone compound according to [1], wherein
$R^1$ is a C1-C3 alkyl group or a halogen atom;
$R^2$ and $R^4$ are hydrogen atoms;
$R^3$ is a hydrogen atom, a C1-C3 alkyl group, or a halogen atom;
$Z^1$ is a C1-C3 alkyl group;
$Z^2$ is a cyano group, a C1-C3 alkoxy group, or a C1-C3 alkylthio group;
$Z^3$ is a C1-C3 alkyl group or a halogen atom; and
X is an oxygen atom.

[3] The tetrazolinone compound according to [1], wherein
$R^1$ is a C1-C3 alkyl group;
$R^2$, $R^3$, and $R^4$ are hydrogen atoms;
$Z^1$ is a C1-C3 alkyl group;
$Z^2$ is a cyano group;
$Z^3$ is a C1-C3 alkyl group; and
X is an oxygen atom.

[4] A pest control agent comprising the tetrazolinone compound according to any one of [1] to [3].

[5] A method for controlling pests, which comprises treating plants or soil with an effective amount of the tetrazolinone compound according to any one of [1] to [3].

[6] Use of the tetrazolinone compound according to any one of [1] to [3].

According to the present invention, pests can be controlled.

MODE FOR CARRYING OUT THE INVENTION

A compound represented by formula (1) is sometimes referred to as the present compound, and a pest control agent containing the present compound is sometimes referred to as the present control agent.

Substituents as used herein will be mentioned in detail below.

Examples of the halogen atom include a fluorine atom, a chlorine atom, a bromine atom, and an iodine atom.

Examples of the C1-C3 alkyl group include an ethyl group, an ethyl group, a propyl group, and an isopropyl group.

Examples of the C1-C3 alkyl group optionally having a fluorine atom include a methyl group, an ethyl group, a propyl group, an isopropyl group, a fluoromethyl group, a difluoromethyl group, a trifluoromethyl group, a 2-fluoroethyl group, a 2,2-difluoroethyl group, a 2,2,2-trifluoroethyl group, a pentafluoroethyl group, 1,1-difluoroethyl group, a 2-fluoropropyl group, a 3-fluoropropyl group, a 2,2-difluoropropyl group, a 2,3-difluoropropyl group, a 3,3,3-trifluoropropyl group, a 3,3,4,4,4-pentafluoropropyl group, a heptafluoropropyl group, and a heptafluoroisopropyl group.

Examples of the C1-C3 alkyl group optionally having a halogen atom include a methyl group, an ethyl group, a propyl group, an isopropyl group, a chloromethyl group, a dichloromethyl group, a fluoromethyl group, a difluoromethyl group, a chlorofluoromethyl group, a dichlorofluoromethyl group, a chlorodifluoromethyl group, a trifluoromethyl group, a trichloromethyl group, a tribromomethyl group, a 2-fluoroethyl group, a 1,1-difluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, a 2-chloro-2-fluoroethyl group, a 2-chloro-2,2-difluoroethyl group, a 2-fluoropropyl group, a 3-fluoropropyl group, a 2,2-difluoropropyl group, a 2,3-difluoropropyl group, a 3,3,3-trifluoropropyl group, a heptafluoropropyl group, and a heptafluoroisopropyl group.

Examples of the C1-C3 alkoxy group include a methoxy group, an ethoxy group, a propoxy group, and an isopropoxy group.

Examples of the C1-C3 alkoxy group optionally having a halogen atom include a methoxy group, an ethoxy group, a propoxy group, an isopropoxy group, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, and a 3-bromopropoxy group.

Examples of the C1-C3 alkylthio group include a methylthio group, an ethylthio group, a propylthio group, and an isopropylthio group.

Examples of the C1-C3 alkylthio group optionally having a halogen atom include a methylthio group, an ethylthio group, a propylthio group, an isopropylthio group, a monofluoromethylthio group, a difluoromethylthio group, a trifluoromethylthio group, a trichloromethylthio group, a tribromomethylthio group, a triiodomethylthio group, a chlorofluoromethylthio group, a chlorodifluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-trifluoroethylthio group, a 2,2,2-tribromoethylthio group, a 2,2,2-triiodoethylthio group, and a 2,2-difluoroethylthio group.

Examples of the C3-C4 alkynyloxy group include a 2-propionyloxy group, a 2-butynyloxy group, and a 3-butynyloxy group.

Examples of the C3-C4 alkynyloxy group optionally having a halogen atom include a 2-propionyloxy group, a 2-butynyloxy group or 3-butynyloxy group, a 1,1-difluoro-2-propionyloxy group, a 1,1-dichloro-2-propionyloxy group, a 1,1-difluoro-2-butynyloxy group, a 1,1-dichloro-2-butynyloxy group, a 4,4,4-trifluoro-2-butynyloxy group, a 4,4,4-trichloro-2-butynyloxy group, a 4,4,4-tribromo-2-butynyloxy group, a 1,1-difluoro-3-butynyloxy group, a 2,2-difluoro-3-butynyloxy group, a 1,1,2,2-tetrafluoro-3-butynyloxy group, and a 2,2-dichloro-3-butynyloxy group.

The C2-C4 dialkylamino group represents an amino group in which two hydrogen atoms on nitrogen are substituted with the same or different straight and/or branched alkyl group(s), and represents an amino group in which the total number of carbon atoms of two alkyl groups on nitrogen is 2 to 4. Examples of the C2-C4 dialkylamino group include an N,N-dimethylamino group, an N,N-diethylamino group, an N-ethyl-N-methylamino, an N-methyl-N-propylamino group, and an N-methyl-N-isopropylamino.

Examples of the aspect of the present compound represented by formula (1) include compounds in which the substituent is shown below.

A compound in which $R^2$ is a C1-C3 alkyl group optionally having a fluorine atom.
A compound in which $R^2$ is a C1-C3 alkyl group.
A compound in which $R^2$ is a halogen atom.
A compound in which $R^2$ and $R^4$ are hydrogen atoms.
A compound in which $R^3$ is a hydrogen atom.
A compound in which $R^3$ is a C1-C3 alkyl group.
A compound in which $R^3$ is a halogen atom.
A compound in which $Z^2$ is a C1-C3 alkyl group.
A compound in which $Z^2$ is a C1-C3 alkoxy group optionally having a halogen atom.
A compound in which $Z^2$ is a C1-C3 alkoxy group.
A compound in which $Z^2$ is a C3-C4 alkynyloxy group optionally having a halogen atom.
A compound in which $Z^2$ is a C3-C4 alkynyloxy group.
A compound in which $Z^2$ is a C1-C3 alkylthio group optionally having a halogen atom.
A compound in which $Z^2$ is a C1-C3 alkylthio group.
A compound in which $Z^2$ is a C2-C4 dialkylamino group.
A compound in which $Z^2$ is a cyano group.
A compound in which $Z^3$ is a hydrogen atom.
A compound in which $Z^3$ is an alkyl group optionally having a halogen atom.
A compound in which $Z^3$ is a C1-C3 alkyl group.
A compound in which $Z^3$ is a halogen atom.
A compound in which $Z^3$ is a cyano group.

A compound in which $R^1$ is a C1-C3 alkyl group or a halogen atom, $R^2$, $R^3$, and $R^4$ are hydrogen atoms, $Z^1$ is a C1-C3 alkyl group, $Z^2$ is a C1-C3 alkoxy group optionally having a halogen atom, or a C1-C3 alkylthio group, $Z^3$ is a C1-C3 alkyl group, and X is an oxygen atom.

A compound in which $R^1$ is a C1-C3 alkyl group optionally having a fluorine atom, or a halogen atom, $R^2$ and $R^4$ are hydrogen atoms, $R^3$ is a hydrogen atom or a C1-C3 alkyl group, $Z^1$ is a C1-C3 alkyl group optionally having a halogen atom, $Z^2$ is a C1-C3 alkoxy group optionally having a halogen atom, a C3-C4 alkynyloxy group, a C1-C3 alkylthio group optionally having a halogen atom, or a cyano group, $Z^3$ is a hydrogen atom, a C1-C3 alkyl group optionally having a halogen atom, a halogen atom, or a cyano group, and X is an oxygen atom.

A compound in which $R^1$ is a C1-C3 alkyl group optionally having a fluorine atom, or a halogen atom, $R^2$ and $R^4$ are hydrogen atoms, $R^3$ is a hydrogen atom or a C1-C3 alkyl group, $Z^1$ is a C1-C3 alkyl group optionally having a halogen atom, $Z^2$ is a C1-C3 alkoxy group optionally having a halogen atom, a C3-C4 alkynyloxy group, or a C1-C3 alkylthio group optionally having a halogen atom, $Z^3$ is a hydrogen atom, a C1-C3 alkyl group optionally having a halogen atom, or a halogen atom, and X is an oxygen atom.

A compound in which $R^1$ is a C1-C3 alkyl group optionally having a fluorine atom, or a halogen atom, either or both of $R^2$ and $R^4$ is/are fluorine atom(s), $R^3$ is a hydrogen atom or a C1-C3 alkyl group, $Z^1$ is a C1-C3 alkyl group optionally having a halogen atom, $Z^2$ is a C1-C3 alkoxy group optionally having a halogen atom, a C3-C4 alkynyloxy group, a C1-C3 alkylthio group optionally having a halogen atom, or a cyano group, $Z^3$ is a hydrogen atom, a C1-C3 alkyl group optionally having a halogen atom, a halogen atom, or a cyano group, and X is an oxygen atom.

A compound in which $R^1$ is a C1-C3 alkyl group, $R^2$ and $R^4$ are hydrogen atoms, $R^3$ is a hydrogen atom, $Z^1$ is a C1-C3 alkyl group optionally having a halogen atom, $Z^2$ is a C1-C3 alkoxy group optionally having a halogen atom, a C3-C4 alkynyloxy group, or a C1-C3 alkylthio group optionally having a halogen atom, $Z^3$ is a C1-C3 alkyl group optionally having a halogen atom, or a halogen atom, and X is an oxygen atom.

A compound in which $R^1$ is a C1-C3 alkyl group, $R^2$, $R^3$, and $R^4$ are hydrogen atoms, $Z^1$ is a C1-C3 alkyl group, $Z^2$ is a C1-C3 alkoxy group, $Z^3$ is a C1-C3 alkyl group or a halogen atom, and X is an oxygen atom.

A compound in which $R^1$ is a C1-C3 alkyl group or a halogen atom, $R^2$, $R^3$, and $R^4$ are hydrogen atoms, Z is a C1-C3 alkyl group, $Z^2$ is a C1-C3 alkoxy group, a C1-C3 alkylthio group, or a cyano group, $Z^3$ is a C1-C3 alkyl group optionally having a halogen atom, a halogen atom, or a cyano group, and X is an oxygen atom.

A compound in which $R^1$ is a C1-C3 alkyl group or halogen atom, $R^2$, $R^3$, and $R^4$ are hydrogen atoms, $Z^1$ is a C1-C3 alkyl group, $Z^2$ is a C1-C3 alkoxy group, $Z^3$ is a C1-C3 alkyl group optionally having a halogen atom, halogen atom, or a cyano group, and X is an oxygen atom.

A compound in which $R^1$ is a C1-C3 alkyl group or a halogen atom, $R^2$, $R^3$, and $R^4$ are hydrogen atoms, $Z^1$ is a C1-C3 alkyl group, $Z^2$ is a C1-C3 alkylthio group, $Z^3$ is a C1-C3 alkyl group optionally having a halogen atom, a halogen atom, or a cyano group, and X is an oxygen atom.

A compound in which $R^1$ is a C1-C3 alkyl group or halogen atom, $R^2$, $R^3$, and $R^4$ are hydrogen atoms, $Z^1$ is a C1-C3 alkyl group, $Z^2$ is a cyano group, $Z^3$ is a C1-C3 alkyl group optionally having a halogen atom, a halogen atom, or a cyano group, and X is an oxygen atom.

A compound in which $R^1$ is a C1-C3 alkyl group or a halogen atom, $R^3$ is a hydrogen atom or a C1-C3 alkyl group, $R^2$ and $R^4$ are hydrogen atoms, $Z^1$ is a C1-C3 alkyl group, $Z^2$ is a C1-C3 alkoxy group, a C1-C3 alkylthio group, or a cyano group, $Z^3$ is a hydrogen atom, a C1-C3 alkyl group optionally having a halogen atom, a halogen atom, or a cyano group, and X is an oxygen atom.

A compound in which $R^1$ is a C1-C3 alkyl group, $R^3$ is a hydrogen atom or a C1-C3 alkyl group, $R^2$ and $R^4$ are hydrogen atoms, $Z^1$ is a C1-C3 alkyl group, $Z^2$ is a C1-C3 alkoxy group, $Z^3$ is a hydrogen atom, a C1-C3 alkyl group optionally having a halogen atom, a halogen atom, or a cyano group, and X is an oxygen atom.

A compound in which $R^1$ is a methyl group, $R^3$ is a hydrogen atom or a methyl group, $R^2$ and $R^4$ are hydrogen atoms, $Z^1$ is a C1-C3 alkyl group, $Z^2$ is a C1-C3 alkoxy group, a C1-C3 alkylthio group, or a cyano group, $Z^3$ is a hydrogen atom, a C1 alkyl group optionally having a halogen atom, or a halogen atom, and X is an oxygen atom.

A compound in which $R^1$ is a methyl group, $R^3$ is a hydrogen atom or a methyl group, $R^2$ and $R^4$ are hydrogen atoms, $Z^1$ is a C1-C3 alkyl group, $Z^2$ is a C1-C3 alkoxy group, $Z^3$ is a hydrogen atom, a C1 alkyl group optionally having a halogen atom, or a halogen atom, and X is an oxygen atom.

A compound in which $R^1$ is a methyl group, $R^3$ is a hydrogen atom or a methyl group, $R^2$ and $R^4$ are hydrogen atoms, $Z^1$ is a C1-C3 alkyl group, $Z^2$ is a C1-C3 alkylthio group, $Z^3$ is a hydrogen atom, a C1 alkyl group optionally having a halogen atom, or a halogen atom, and X is an oxygen atom.

A compound in which $R^1$ is a methyl group, $R^3$ is a hydrogen atom or a methyl group, $R^2$ and $R^4$ are hydrogen atoms, $Z^1$ is a C1-C3 alkyl group, $Z^2$ is a cyano group, $Z^3$ is a hydrogen atom, a C1 alkyl group optionally having a halogen atom, or a halogen atom, and X is an oxygen atom.

Next, a process for producing the present compound will be described.

The present compound can be produced, for example, by the following Production Processes.

(Production Process A)

The present compound represented by formula (1) (hereinafter referred to as the compound (1)) can be produced by reacting a compound represented by formula (A1) (hereinafter referred to as the compound (A1)) with a compound represented by formula (A2) (hereinafter referred to as the compound (A2)) in the presence of a base:

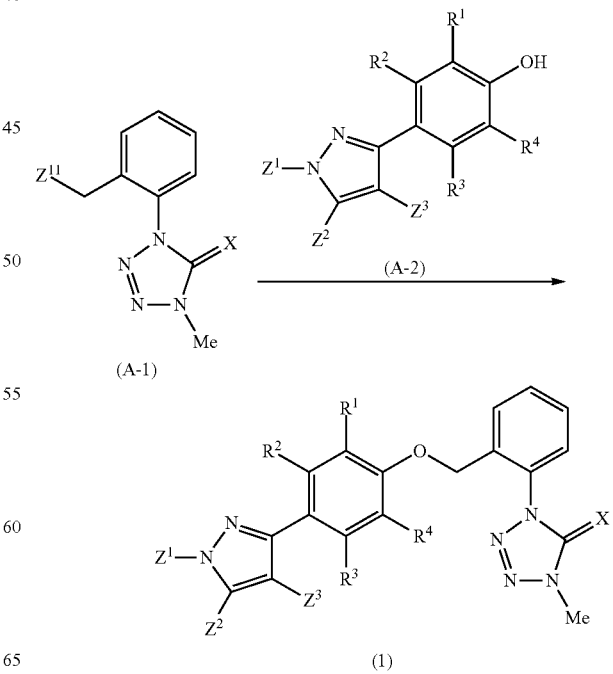

wherein $R^1$, $R^2$, $R^3$, $R^4$, X, $Z^1$, $Z^2$, and $Z^3$ are the same as defined above, and $Z^{11}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A-2) is usually used in the proportion within a range of 1 to 10 mols, and the base is usually used in the proportion within a range of 1 to 10 mols, based on 1 mol of the compound (A-1).

The reaction temperature of the reaction is usually within a range of −20 to 150° C. The reaction time of the reaction is usually within a range of 0.1 to 24 hours.

If necessary, sodium iodide, tetrabutylammonium iodide, and the like may be added in the reaction, and the amount to be added is usually within a range of 0.001 to 1.2 mols based on 1 mol of the compound (A-1).

After completion of the reaction, the compound (1) can be isolated by performing post-treatment operations such as extraction of the reaction mixture with an organic solvent, and drying and concentration of the organic layer. It is also possible to isolate the compound (1) by post-treatment operations such as filtration and concentration of the reaction mixture. The isolated present compound may be further purified by chromatography, recrystallization, and the like.

(Production Process B)

The compound (1) can be produced by reacting a compound represented by formula (B-1) (hereinafter referred to as the compound (B-1)) with a compound represented by formula (B-2) (hereinafter referred to as the compound (B-2)) in the presence of a base:

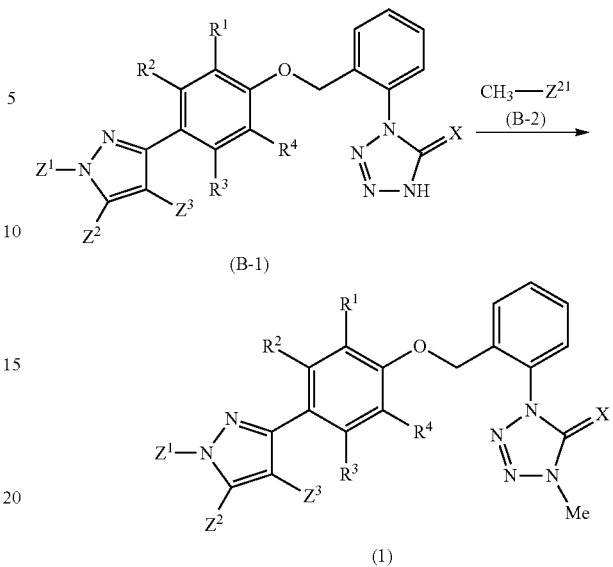

wherein $R^1$, $R^2$, $R^3$, $R^4$, X, $Z^1$, $Z^2$, and $Z^3$ are the same as defined above, and $Z^{21}$ represents a leaving group such as a chlorine atom, a bromine atom, an iodine atom, a methanesulfonyloxy group, a methoxysulfonyloxy group, a trifluoromethanesulfonyloxy group, or a p-toluenesulfonyloxy group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the compound (B-2) to be used in the reaction include methyl halides such as methyl bromide and methyl iodide; sulfuric acid esters such as dimethyl sulfate; and sulfonic acid esters such as methyl p-toluenesulfonate and methyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (B-2) is usually used in the proportion within a range of 1 to 10 mols, and the base is usually used in the proportion within a range of 1 to 10 mols, based on 1 mol of the compound (B-1).

The reaction temperature of the reaction is usually within a range of −20 to 150° C. The reaction time of the reaction is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound may be further purified by chromatography, recrystallization, and the like.

(Production Process C)

Among the compounds (1), a compound represented by formula (1-S) in which X is a sulfur atom (hereinafter referred to as the compound (1-S)) is produced from a compound in which X is an oxygen atom (hereinafter referred to as the compound (1-O)) of the compounds (1) by a known sulfidation reaction and produced, for example, by reacting the compound (1-O) with a sulfurizing agent:

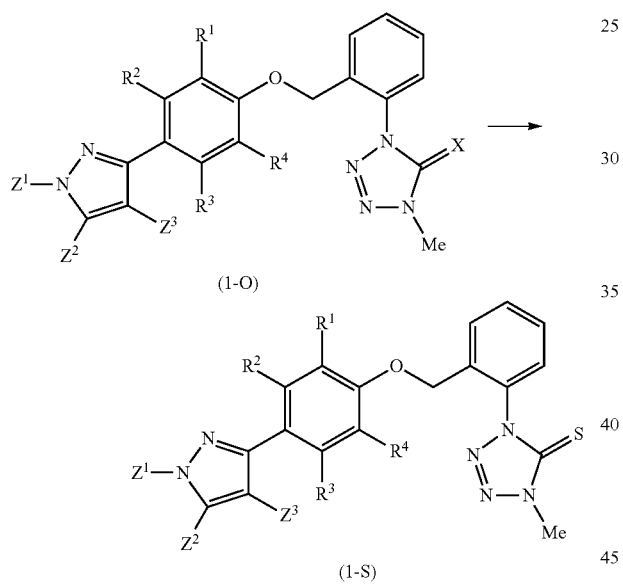

wherein $R^1$, $R^2$, $R^3$, $R^4$, $Z^1$, $Z^2$, and $Z^3$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile and propionitrile; and mixtures thereof.

Examples of the sulfurizing agent to be used in the reaction include phosphorous pentasulfide, Lawesson's reagent (2,4-Bis(4-methoxyphenyl)-1,3,2,4-dithiadiphosphetane 2,4-disulfide), and the like.

In the reaction, the sulfurizing agent is usually used in the proportion within a range of 0.5 to 10 mols based on 1 mol of the compound (1-O).

The reaction temperature of the reaction is usually within a range of −20 to 150° C. The reaction time of the reaction is usually within a range of 0.1 to 24 hours.

If necessary, organic bases such as pyridine and triethylamine, and inorganic bases such as alkali metal hydroxide and alkali metal carbonate may be added in the reaction, and the amount to be added is usually within a range of 0.5 to 10 mols based on 1 mol of the compound (1-O).

After completion of the reaction, the compound (1-S) can be isolated by performing post-treatment operations such as extraction of the reaction mixture with an organic solvent, and drying and concentration of the organic layer. The isolated present compound may be further purified by chromatography, recrystallization, and the like.

(Production Process D)

Among the compounds (1), a compound represented by formula (1-D) in which $R^1$ is $R^{41}$ (hereinafter referred to as the compound (1-D)) can be produced by reacting a compound represented by formula (D-1) (hereinafter referred to as the compound (D-1)) with a compound represented by formula (D-2) (hereinafter referred to as the compound (D-2)) in the presence of a base and a catalyst:

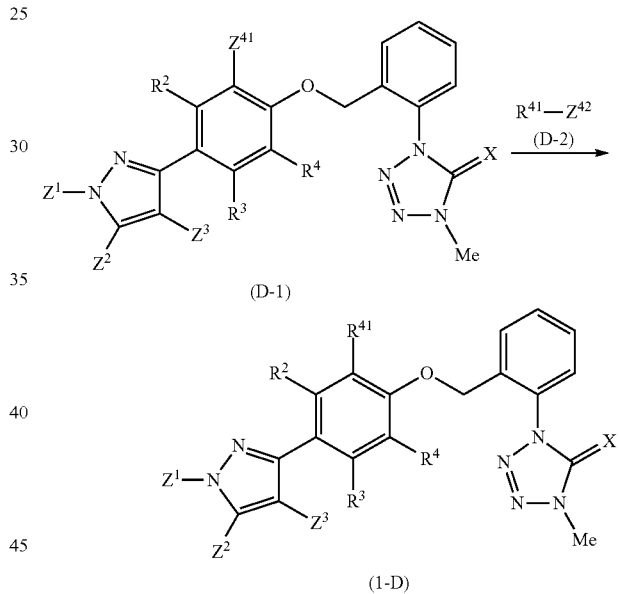

wherein $R^2$, $R^3$, $R^4$, X, $Z^1$, $Z^2$, and $Z^3$ are the same as defined above, $Z^{41}$ represents a chlorine atom, a bromine atom, an iodine atom, or a trifluoromethanesulfonyloxy group, $R^{41}$ represents a C1-C3 alkyl group optionally having a fluorine atom, and $Z^{42}$ represents $B(OH)_2$, an alkoxyboryl group, or trifluoroborate ($BF_3^-K^+$).

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and onitrile; alcohols such as methanol, ethanol, propanol, and butanol; water; and mixtures thereof.

It is possible to usually use, as the compound (D-2) to be used in the reaction, commercially available compounds, or compounds produced by a known method mentioned in N. Miyaura and A. Suzuki, Chem. Rev., 1995, 95, 2457. It is possible to produce a boric acid ester derivative, for example, by reacting an iodine compound ($R^{41}$—I) of $R^{41}$ or a bromo compound ($R^{41}$—Br) of $R^{41}$ with an alkyllithium such as butyllithium, followed by a reaction with a boric acid ester. It is possible to produce a boric acid ester derivative by optionally hydrolyzing the boric acid ester derivative thus obtained. It is also possible to produce trifluoroborate ($BF_3^-K^+$) by fluorinating a certain compound (B2) with potassium hydrogen fluoride in accordance with a known method mentioned in Molander et al. Acc. Chem. Res., 2007, 40, 275.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshineferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (D-2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (D-1).

The reaction temperature of the reaction is usually within a range of 0 to 150° C. The reaction time of the reaction is usually within a range of 0.1 to 24 hours.

After completion of the reaction, the compound (1-D) can be isolated by performing post-treatment operations such as extraction of the reaction mixture with an organic solvent, and drying and concentration of the organic layer. The isolated present compound may be further purified by chromatography, recrystallization, and the like.

Among the compounds (1), a compound represented by formula (1-D-2) in which $R^3$ is $R^{41}$ (hereinafter referred to as the compound (1-D-2)) can be produced in accordance with the method for producing the compound (1-D) by reacting a compound represented by formula (D-3) (hereinafter referred to as the compound (D-3)) with the compound (D-2) in the presence of a base and a catalyst:

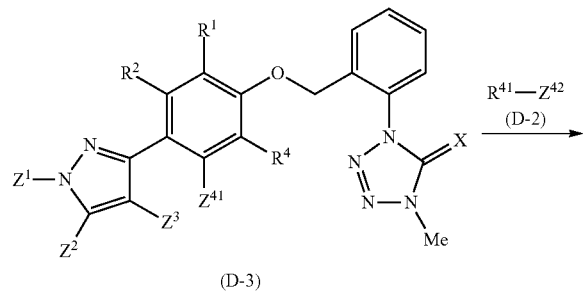

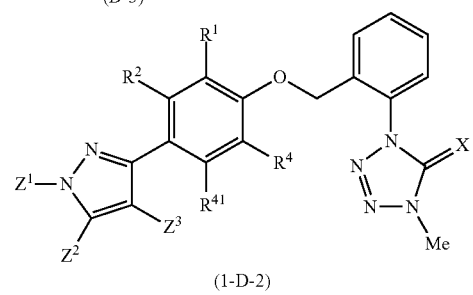

wherein $R^1$, $R^2$, $R^4$, $R^{41}$, X, $Z^1$, $Z^2$, $Z^3$, $Z^{41}$, and $Z^{42}$ are the same as defined above.

(Production Process E)

Among the compounds (1), a compound represented by formula (1-E) in which $Z^3$ is a methyl group (hereinafter referred to as the compound (1-E)) can be produced by reacting a compound represented by formula (E-1) (hereinafter referred to as the compound (E-1)) with a reducing agent in the presence of an acid:

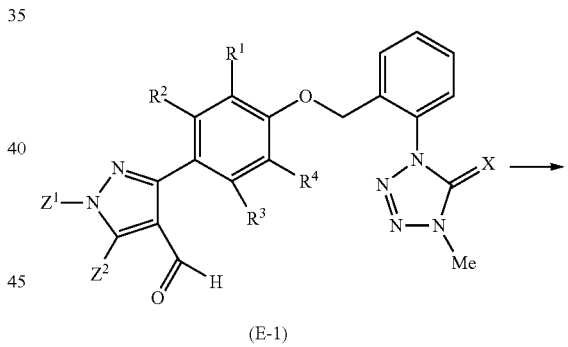

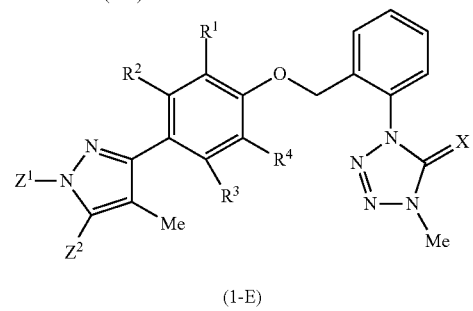

wherein $R^1$, $R^2$, $R^3$, $R^4$, X, $Z^1$, and $Z^2$ are the same as defined above.

The reaction is usually performed in a solvent, or in the absence of a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile and propionitrile; and mixtures thereof.

Examples of the acid to be used in the reaction include boron trifluoride, trifluoroacetic acid, and the like.

Examples of the reducing agent to be used in the reaction include metal boronate compounds such as lithium borohydride, sodium borohydride, and potassium borohydride; trialkylsilane compounds such as triethylsilane; and the like.

In the reaction, the reducing agent is usually used in the proportion within a range of 1 to 10 mols, and the acid is usually used in the proportion within a range of 1 to 10 mols or a large excess, based on 1 mol of the compound (E-1).

The reaction temperature of the reaction is usually within a range of −20 to 150° C. The reaction time of the reaction is usually within a range of 0.1 to 24 hours.

After completion of the reaction, the compound (1-E) can be isolated by performing post-treatment operations such as extraction of the reaction mixture with an organic solvent, and drying and concentration of the organic layer. It is also possible to isolate the compound (1-E) by post-treatment operations such as filtration and concentration of the reaction mixture. The isolated compound may be further purified by chromatography, recrystallization, and the like.

(Production Process F)

Among the compounds (1), a compound represented by formula (1-F) in which $Z^3$ is a difluoromethyl group (hereinafter referred to as the compound (1-F)) can be produced by reacting the compound (E-1) with a fluorinating agent:

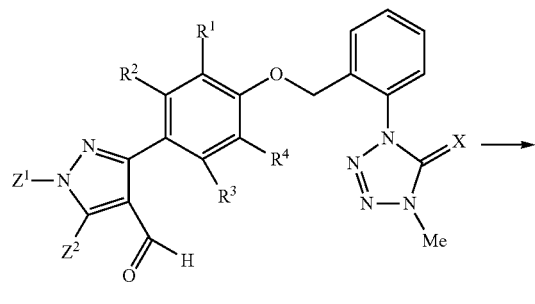

(E-1)

wherein $R^1$, $R^2$, $R^3$, $R^4$, X, $Z^1$, and $Z^2$ are the same as defined above.

The reaction is usually performed in a solvent.

Examples of the solvent to be used in the reaction include hydrocarbons such as heptane, hexane, cyclohexane, pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile and propionitrile; and mixtures thereof.

Examples of the fluorinating agent to be used in the reaction include (diethylamino)sulfur trifluoride, bis(methoxyethyl)aminosulfur trifluoride, 4-tert-butyl-2,6-dimethylphenylsulfur trifluoride, (diethylamino)difluorosulfonium tetrahydroborate, difluoro(morpholino)sulfonium tetrahydroborate, and the like.

In the reaction, it is also possible to add, as a reaction accelerator, diazabicycloundecene, triethylamine trihydroborate, and the like.

In the reaction, the fluorinating agent is usually used in the proportion within a range of 1 to 20 mols, and the reaction accelerator is usually used in the proportion within a range of 0 to 10 mols, based on 1 mol of the compound (E-1).

The reaction temperature of the reaction is usually within a range of −20 to 150° C. The reaction time of the reaction is usually within a range of 0.1 to 24 hours.

After completion of the reaction, the compound (1-F) can be isolated by performing post-treatment operations such as extraction of the reaction mixture with an organic solvent, and drying and concentration of the organic layer. The isolated present compound may be further purified by chromatography, recrystallization, and the like.

(Production Process G)

A compound represented by formula (1-G) (hereinafter referred to as the compound (1-G)) can be produced by reacting a compound represented by formula (G-1) (hereinafter referred to as the compound (G-1)) with a dehydrating agent:

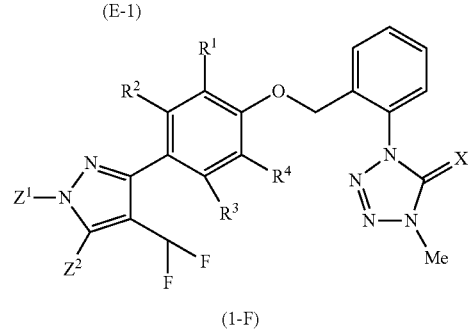

(1-F)

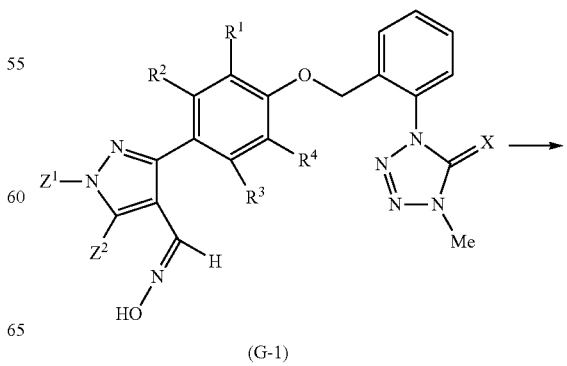

(G-1)

(1-G)

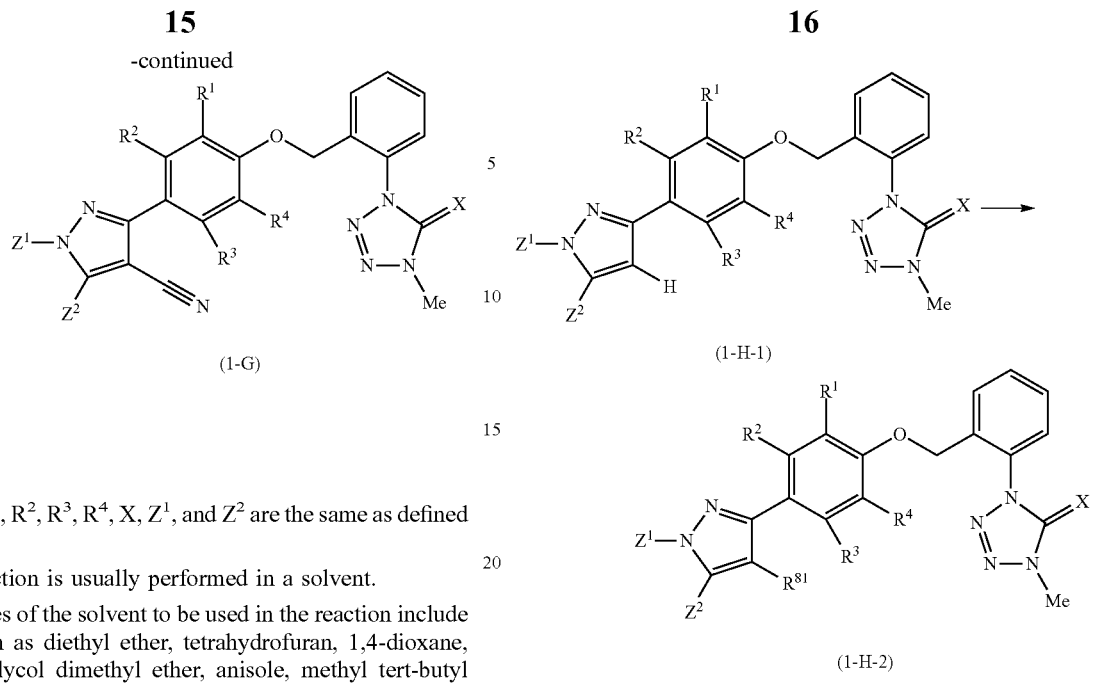

(1-H-1)

(1-H-2)

wherein $R^1$, $R^2$, $R^3$, $R^4$, X, $Z^1$, and $Z^2$ are the same as defined above.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as heptane, hexane, cyclohexane, pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; and mixtures thereof.

Examples of the dehydrating agent to be used in the reaction include phosphorus oxychloride, phosphorus pentachloride, phosphorus oxychloride, 2,4,6-trichloro-1,3,5-triazine, and acid anhydrides such as acetic anhydride.

The base may be used in the reaction, and examples of the base to be used include organic bases such as triethylamine, pyridine, N-methylmorpholine, N-methylpiperidine, 4-dimethylaminopyridine, diisopropylethylamine, lutidine, collidine, diazabicycloundecene, diazabicyclononene, and the like. It is also possible to use these bases as the solvent.

In the reaction, a cyanating agent is usually used in the proportion within a range of 1 to 20 mols, and the base is usually used in the proportion within a range of 0.1 to 20 mols, based on 1 mol of compound (G-1).

The reaction temperature of the reaction is usually within a range of −20 to 150° C. The reaction time of the reaction is usually within a range of 0.1 to 72 hours.

After completion of the reaction, the compound (1-G) can be isolated by performing post-treatment operations such as extraction of the reaction mixture with an organic solvent, and drying and concentration of the organic layer. When the precipitate is formed, the compound (1-G) can be isolated by collecting the precipitate through filtration. The isolated compound may be further purified by operations such as chromatography and recrystallization.

(Production Process H)

A compound represented by formula (1-H-2) (hereinafter referred to as the compound (1-H-2)) can be produced by reacting a compound represented by formula (1-H-1) (hereinafter referred to as the compound (1-H-1)) with a halogenating agent:

wherein $R^1$, $R^2$, $R^3$, $R^4$, X, $Z^1$, and $Z^2$ are the same as defined above, and R″ represents a chlorine atom, a bromine atom, or an iodine atom.

The reaction is usually performed in a solvent.

Examples of the solvent to be used in the reaction include hydrocarbons such as heptane, hexane, cyclohexane, pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile and propionitrile; water; and mixtures thereof.

Examples of the halogenating agent to be used in the reaction include N-chlorosuccinimide, N-bromosuccinimide, N-iodosuccinimide, fluorine, chlorine, bromine, iodine, 1-chloromethyl-4-fluoro-1,4-diazoniabicyclo[2,2,2]octane bis(tetrafluoroborate), sulfuryl chloride, and the like.

In the reaction, the halogenating agent is usually used in the proportion within a range of 1 to 10 mols based on 1 mol of the compound (1-H-1).

The reaction temperature of the reaction is usually within a range of −20 to 150° C. The reaction time of the reaction is usually within a range of 0.1 to 24 hours.

After completion of the reaction, the compound (1-H-2) can be isolated by performing post-treatment operations such as extraction of the reaction mixture with an organic solvent, and drying and concentration of the organic layer. The isolated present compound may be further purified by chromatography, recrystallization, and the like.

(Production Process I)

A compound represented by formula (1-I) (hereinafter referred to as the compound (1-I)) can be produced by reacting a compound represented by formula (I-1) (hereinafter referred to as the compound (I-1)) with a compound represented by formula (I-2) (hereinafter referred to as the compound (I-2)) in the presence of a base:

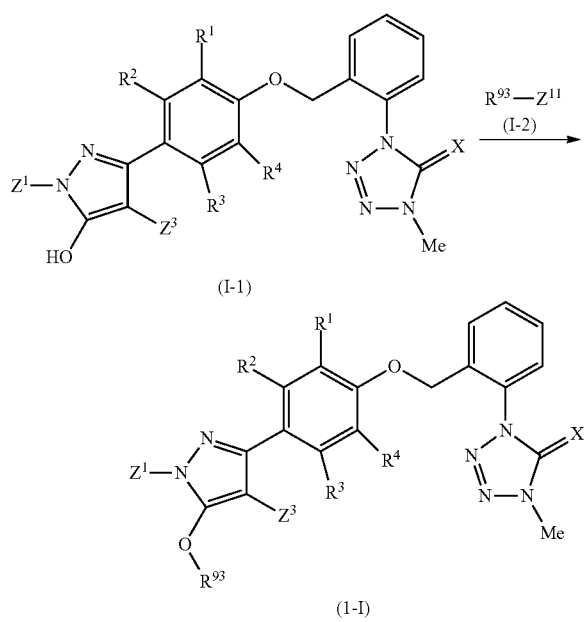

wherein $R^1$, $R^2$, $R^3$, $R^4$, X, $Z^1$, $Z^3$, and $Z^{11}$ are the same as defined above, and $R^{93}$ represents an alkyl group optionally having a halogen atom.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (I-2) is usually used in the proportion within a range of 1 to 10 mols, and the base is usually used in the proportion within a range of 1 to 10 mols, based on 1 mol of the compound (I-1).

The reaction temperature of the reaction is usually within a range of −20 to 150° C. The reaction time of the reaction is usually within a range of 0.1 to 24 hours.

If necessary, sodium iodide, tetrabutylammonium iodide, and the like may be added in the reaction, and these compounds are usually used in the proportion within a range of 0.001 to 1.2 mols based on 1 mol of the compound (I-1).

After completion of the reaction, the compound (1-I) can be isolated by performing post-treatment operations such as extraction of the reaction mixture with an organic solvent, and drying and concentration of the organic layer. It is also possible to isolate the compound (1-I) by post-treatment operations such as filtration and concentration of the reaction mixture. The isolated present compound may be further purified by chromatography, recrystallization, and the like.

The process for synthesizing an intermediate compound will be mentioned in detail below.

(Reference Production Process A)

A compound represented by formula (XA3) (hereinafter referred to as the compound (XA3)) can be produced by reacting a compound represented by formula (XA1) (hereinafter referred to as the compound (XA1)), or a compound (XA2) (hereinafter referred to as the compound (XA2)) with an azidation agent:

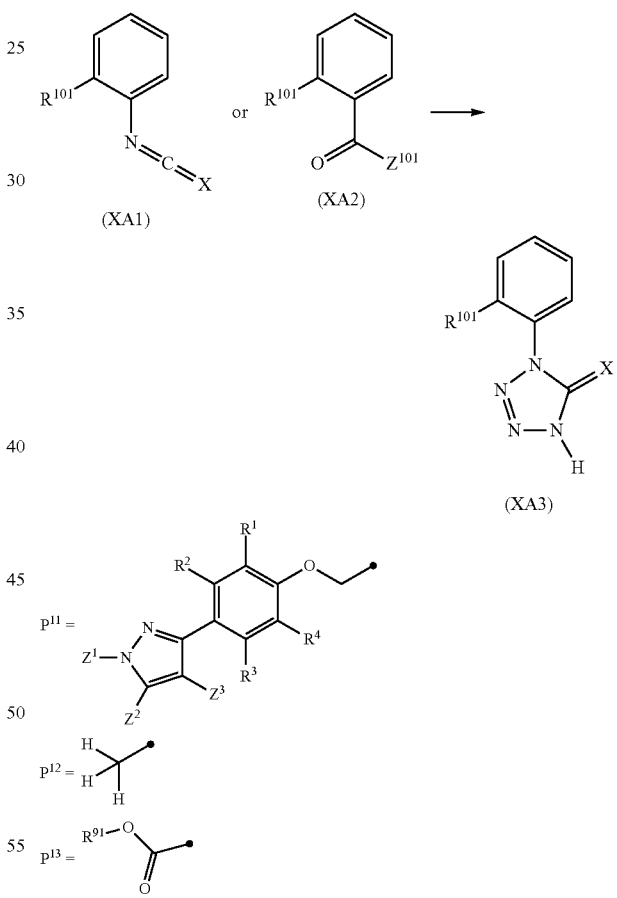

wherein $R^1$, $R^2$, $R^3$, $R^4$, X, $Z^1$, $Z^2$, and $Z^3$ are the same as defined above, $R^{101}$ represents $P^{11}$, $P^{12}$, or $P^{13}$, $R^{91}$ represents a C1-C12 alkyl group, $Z^{101}$ represents a chlorine atom or a bromine atom, and the symbol ● represents a binding site.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of –20 to 150° C. The reaction time of the reaction is usually within a range of 0.1 to 24 hours.

If necessary, Lewis acid such as aluminum chloride or zinc chloride may be added in the reaction, and these compounds are usually used in the proportion within a range of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) may be further purified by chromatography, recrystallization, and the like.

(Reference Production Process B)

The compound (XA1) can be produced by reacting a compound represented by the following formula (XB1) (hereinafter referred to as the compound (XB1)) with an isocyanating agent:

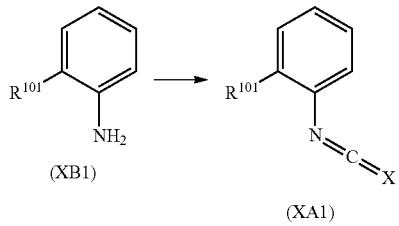

wherein $R^{101}$ and X are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, the isocyanating agent is usually used in the proportion within a range of 1 to 10 mols based on 1 mol of the compound (XB1).

The reaction temperature of the reaction is usually within a range of –20 to 150° C. The reaction time of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added in the reaction, and these compounds are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process C)

The compound (XA2) can be produced by reacting a compound represented by formula (XC1) (hereinafter referred to as the compound (XC1)) with a halogenating agent:

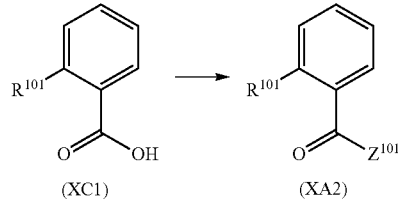

wherein $R^{101}$ and $Z^{101}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; and mixtures thereof.

Examples of the halogenating agent to be used in the reaction include phosphorus oxychloride, phosphorus trichloride, phosphorus pentachloride, thionyl chloride, phosphorus oxychloride, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (XC1).

The reaction temperature of the reaction is usually within a range of –20 to 150° C. The reaction time of the reaction is usually within a range of 0.1 to 24 hours.

The catalyst may be added in the reaction, and examples thereof include N,N-dimethylformamide, and the like.

The amount of the catalyst to be used is usually in the proportion within a range of 0.001 to 1 mol based on 1 mol of the compound (XC1).

If necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added in the reaction, and these compounds are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process D)

The compound (XA1) can be produced by reacting the compound (XB1) with a carbamating agent to obtain a compound represented by formula (XD1) (hereinafter referred to as the compound (XD1)), and reacting the compound (XD1) with an isocyanating agent:

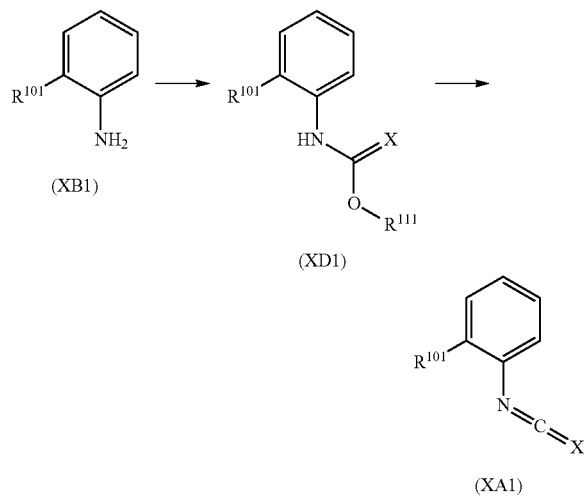

wherein $R^{101}$ and X are the same as defined above, and $R^{111}$ represents a C1-C12 alkyl group or a phenyl group.

The process for producing the compound (XD1) by reacting the compound (XB1) with a carbamating agent will be described below.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, phenyl chlorothioformate, methyl chlorothioformate, and ethyl chlorothioformate.

In the reaction, the carbamating agent is usually used in the proportion within a range of 1 to 10 mols based on 1 mol of the compound (XB1).

The reaction temperature of the reaction is usually within a range of −20 to 150° C. The reaction time of the reaction is usually within a range of 0.1 to 24 hours.

If necessary, bases, for example, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added in the reaction, and the base is usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) by reacting the compound (XD1) with an isocyanating agent will be described below.

The reaction is usually performed in a solvent.

Examples of the solvent to be used in the reaction include ethers such as tetrahydrofuran, dioxane, ethylene glycol dimethyl ether, and methyl tert-butyl ether; aromatic hydrocarbons such as toluene and xylene; carbon tetrachloride, halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the isocyanating agent to be used in the reaction include phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, and chlorotrimethylsilane.

In the reaction, the isocyanating agent is usually used in the proportion within a range of 1 to 10 mols based on 1 mol of the compound (XD1).

The reaction temperature of the reaction is usually within a range of −20 to 250° C. The reaction time of the reaction is usually within a range of 0.1 to 24 hours.

If necessary, bases, for example, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added in the reaction, and the base is usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

A compound represented by formula (XE2) (hereinafter referred to as the compound (XE2) can be produced by reacting a compound represented by formula (XE1) (hereinafter referred to as the compound (XE1)) with hydrogen in the presence of a catalyst:

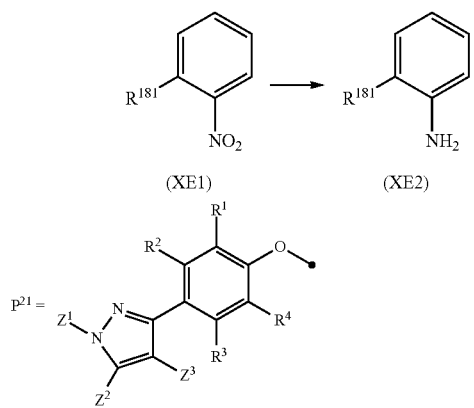

wherein $R^1$, $R^2$, $R^3$, $R^4$, $Z^1$, $Z^2$, and $Z^3$ are the same as defined above, $R^{181}$ represents a hydrogen atom or $P^{21}$, and the symbol ● represents a binding site.

The reaction is usually performed in a solvent.

Examples of the solvent to be used in the reaction include alcohols such as methanol, ethanol, propanol, and butanol; esters such as ethyl acetate, and butyl acetate; halogenated hydrocarbons such as carbon tetrachloride, chloroform, dichloromethane, 1,2-dichloroethane, tetrachloroethane, and chlorobenzene; ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; acetic acid, water; and mixtures thereof.

Examples of the catalyst to be used in the reaction include palladium-carbon (Pd/C), platinum-carbon (Pt/C), osmium-carbon (Os/C), ruthenium-carbon (Ru/C), rhodium-carbon (Rh/C), and Raney nickel.

In the reaction, the catalyst is usually used in the proportion within a range of 0.1 to 1 mol, and hydrogen is used in an excess amount, based on 1 mol of the compound (XE1).

The reaction temperature of the reaction is usually within a range of −20 to 150° C. The reaction time of the reaction is usually within a range of 0.1 to 24 hours.

After completion of the reaction, the compound (XE2) can be isolated by performing post-treatment operations such as filtration of the catalyst and concentration of the organic layer. The isolated compound may be further purified by operations such as distillation, chromatography, and recrystallization.

(Reference Production Process F)

The compound (XE2) can also be produced by reacting the compound (XE1) with a reducing agent in the presence of an acid:

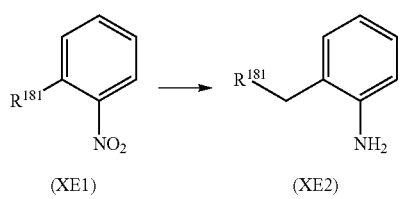

wherein $R^{181}$ is the same as defined above.

The reaction is usually performed in a solvent.

Examples of the solvent to be used in the reaction include aliphatic carboxylic acids such as acetic acid; alcohols such as methanol and ethanol; water; and mixtures thereof.

Examples of the acid to be used in the reaction include hydrochloric acid, sulfuric acid, acetic acid, and an aqueous ammonium chloride solution.

Examples of the reducing agent to be used in the reaction include iron, a tin compound such as tin chloride, and a zinc compound such as zinc chloride.

In the reaction, the reducing agent is usually used in the proportion within a range of 1 to 30 mols based on 1 mol of the compound (XE1).

The reaction temperature of the reaction is usually within a range of −20 to 150° C. The reaction time of the reaction is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by formula (XG2) (hereinafter referred to as the compound (XG2)) can be produced by reacting a compound represented by formula (XG1) (hereinafter referred to as the compound (XG1)) with the compound (B-2) in the presence of a base:

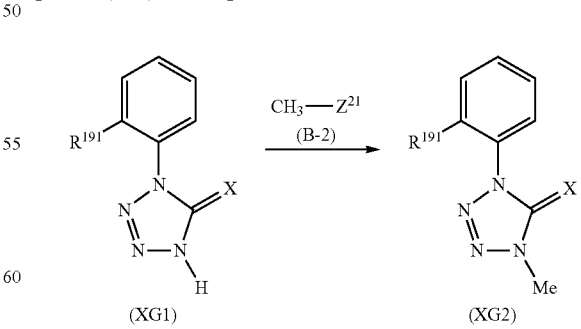

wherein $Z^{21}$ and X are the same as defined above, and $R^{191}$ represents $P^{12}$ or $P^{13}$.

The reaction can be carried out in accordance with the Production Process B.

(Reference Production Process H)

A compound represented by formula (XH2) (hereinafter referred to as the compound (XH2)) can be produced by reacting a compound represented by formula (XH1) (hereinafter referred to as the compound (XH1)) with a halogenating agent in the presence of a radical initiator:

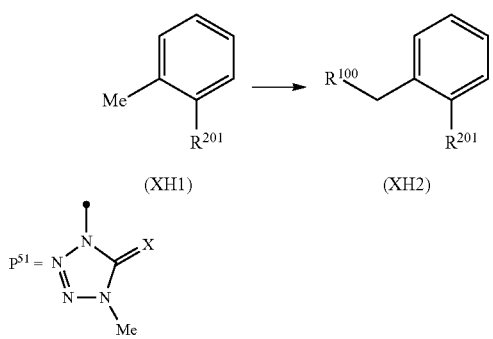

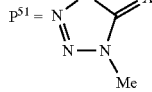

wherein X is the same as defined above, $R^{100}$ represents a chlorine atom, a bromine atom, or an iodine atom, and $R^{201}$ represents $P^{51}$ or a nitro group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, and α,α,α-trichlorotoluene; esters such as ethyl acetate and methyl acetate; ketones such as acetone, methyl ethyl ketone, and methyl isobutyl ketone; nitriles such as acetonitrile and propionitrile; and mixtures thereof.

Examples of the halogenating agent to be usable in the reaction include a chlorinating agent, a brominating agent, and an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, and N-bromophthalimide.

Examples of the radical initiator to be used in the reaction include benzoyl peroxide, azobisisobutyronitrile (AIBN), 1,1-azobis(cyanocyclohexane), diacyl peroxide, dialkyl peroxydicarbonate, tert-alkyl peroxyester, monoperoxycarbonate, di(tert-alkylperoxy)ketal and ketone peroxide, and tri-ethylborane.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by formula (XI2) (hereinafter referred to as the compound (XI2)) can be produced by reacting the compound (XH2) with a compound represented by formula (XI1) (hereinafter referred to as the compound (XI1)):

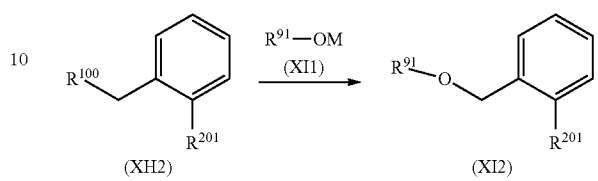

wherein $R^{91}$, $R^{100}$, and $R^{201}$ are the same as defined above, and

M represents sodium, potassium, or lithium.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XI1) include sodium methoxide, sodium ethoxide, sodium n-propoxide, sodium n-butoxide, sodium isopropoxide, sodium sec-butoxide, sodium tert-butoxide, potassium methoxide, potassium ethoxide, potassium n-propoxide, potassium n-butoxide, potassium isopropoxide, potassium sec-butoxide, potassium tert-butoxide, sodium phenoxide, and lithium ethoxide.

In the reaction, the compound (XI1) is usually used in the proportion within a range of 1 to 10 mols based on 1 mol of the compound (XH2).

The reaction temperature of the reaction is usually within a range of −20 to 150° C. The reaction time of the reaction is usually within a range of 0.1 to 24 hours.

After completion of the reaction, the compound (XI2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by formula (XJ1) (hereinafter referred to as the compound (XJ1)) can be produced by reacting the compound (XH2) with water in the presence of a base:

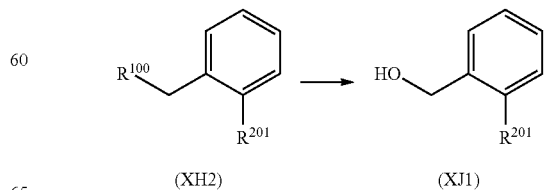

wherein $R^{100}$ and $R^{201}$ are the same as defined above.

The reaction is usually performed in water or a solvent containing water.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; metal organic acid salts such as lithium formate, lithium acetate, sodium formate, sodium acetate, potassium formate, and sodium nitrate; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to a large excess based on 1 mol of the compound (XH2).

The reaction temperature of the reaction is usually within a range of −20 to 150° C. The reaction time of the reaction is usually within a range of 0.1 to 24 hours.

After completion of the reaction, the compound (XJ1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XI2) with a halogenating agent:

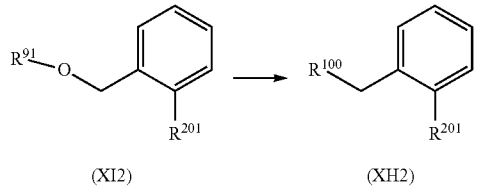

(XI2)        (XH2)

wherein $R^{91}$, $R^{100}$, and $R^{201}$ are the same as defined above:

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include hydrochloric acid, hydrobromic acid, and hydroiodic acid.

In the reaction, the amount of the halogenating agent is usually 1 mol or more based on 1 mol of the compound (XI2).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process L)

The compound (XH2) can also be produced by reacting the compound (XJ1) with a halogenating agent:

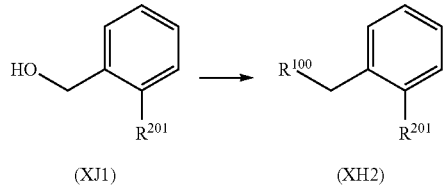

(XJ1)        (XH2)

wherein $R^{100}$ and $R^{201}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxychloride, phosphorus pentabromide, phosphorus triiodide, oxalyl dichloride, oxalyl dibromide, acetyl chloride, carbon tetrabromide, N-bromosuccinimide, lithium chloride, sodium iodide, and acetyl bromide.

In the reaction, the halogenating agent is usually used in the proportion within a range of 1 to 10 mols based on 1 mol of the compound (XJ1).

In order to accelerate the reaction, additives may be added according to the halogenating agent to be used, and specific examples thereof include zinc chloride for acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, and trimethylsilyl chloride for sodium iodide. Any additives are usually used in the proportion within a range of 0.01 to 5 mols based on 1 mol of the compound (XJ1).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by formula (XM2) (hereinafter referred to as the compound (XM2)) can be produced by reacting the compound (XJ1) with a compound represented by formula (XM1) (hereinafter referred to as the compound (XM1)) in the presence of a base:

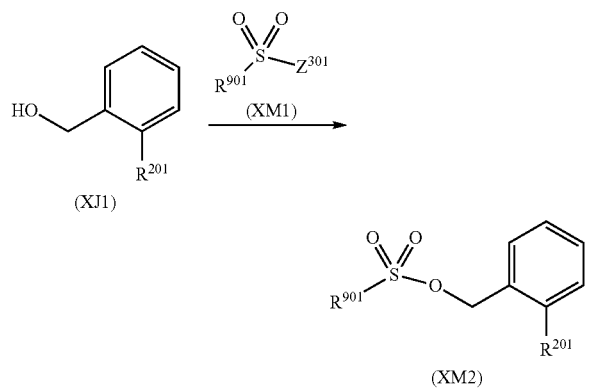

wherein $R^{201}$ is the same as defined above, $R^{901}$ represents a p-methylphenyl group, a methyl group, or a trifluoromethyl group, and $Z^{301}$ represents a fluorine atom, a chlorine atom, a bromine atom, an iodine atom, a methanesulfonyloxy group, or a trifluoromethanesulfonyloxy group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononenene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

In the reaction, the compound (XM1) is usually used in the proportion within a range of 1 to 10 mols, and the base is usually used in the proportion within a range of 1 to 5 mols, based on 1 mol of the compound (XJ1).

The reaction temperature of the reaction is usually within a range of −20 to 150° C. The reaction time of the reaction is usually within a range of 0.1 to 24 hours.

If necessary, additives may be added in the reaction, and examples thereof include sodium iodide and tetrabutylammonium iodide. These additives are usually used in the proportion within a range of 0.001 to 1.2 mols, based on 1 mol of the compound (XJ1).

After completion of the reaction, the compound (XM2) can be isolated by performing post-treatment operations such as extraction of the reaction mixture with an organic solvent, and drying and concentration of the organic layer. The isolated compound (XM2) may be further purified by distillation, chromatography, recrystallization, and the like.

(Reference Production Process O)

A compound represented by formula (XO3) (hereinafter referred to as the compound (XO3)) can be produced by reacting a compound represented by formula (XO1) (hereinafter referred to as the compound (XO1)) with a compound represented by formula (XO2) (hereinafter referred to as the compound (XO2)) in the presence of a reaction accelerator:

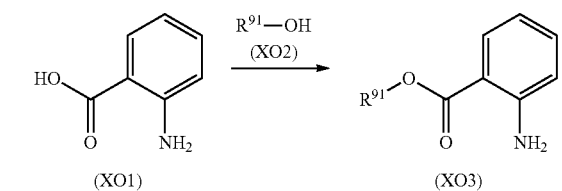

wherein $R^{91}$ is the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof, and the compound (XO2) may be used as the solvent.

Examples of the compound (XO2) to be usable in the reaction include methanol, ethanol, propanol, isopropanol, n-butanol, isobutanol, sec-butanol, t-butanol, and n-pentanol.

In the reaction, the compound (XO2) is used in an excess amount based on the compound (XO1).

Examples of the reaction accelerator to be used in the reaction include acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; reagents such as triphenylphosphine/diethyl azodicarboxylate; thionyl chloride, and boron trifluoride-ethyl ether complex.

In the reaction, the reaction accelerator is usually used in the proportion within a range of 0.01 to 10 mols based on 1 mol of the compound (XO1).

If necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added in the reaction, and these compounds are usually used in the proportion within a range of 0.001 to 5 mols based on 1 mol of the compound (XO1).

The reaction temperature of the reaction is usually within a range of −78 to 100° C. The reaction time of the reaction is usually within a range of 0.1 to 24 hours.

After completion of the reaction, the compound (XO3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XO3) can be produced by reacting the compound (XO1) with a halogenating agent to obtain a compound represented by formula (XP1) (hereinafter referred to as the compound (XP1)), and reacting the compound (XP1) with the compound (XO2):

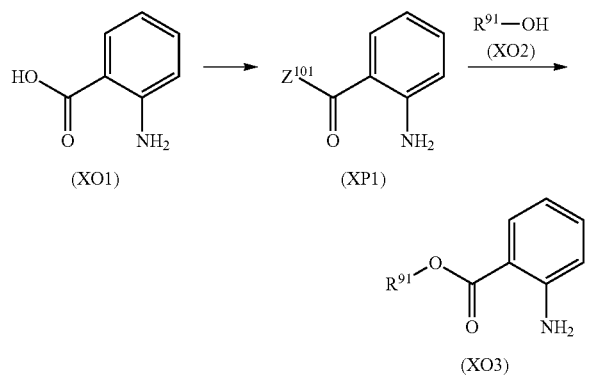

wherein $R^{91}$ and $Z^{101}$ are the same as defined above.

The process for producing the compound (XP1) by reacting the compound (XO1) with a halogenating agent can be carried out in accordance with the reaction mentioned in Reference Production Process C.

The process for producing the compound (XO3) by reacting the compound (XP1) with the compound (XO2) will be described below.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof. The compound (XO2) may also be used as the solvent.

Examples of the compound (XO2) to be usable in the reaction include methanol, ethanol, propanol, isopropanol, n-butanol, isobutanol, sec-butanol, t-butanol, and n-pentanol.

In the reaction, the compound (XO2) is usually used in the proportion within a range of 1 to 50 mols based on 1 mol of the compound (XP1).

The reaction temperature of the reaction is usually within a range of −78 to 100° C. The reaction time of the reaction is usually within a range of 0.1 to 24 hours.

After completion of the reaction, the compound (XO3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XO3) can be produced by reacting the compound (XO1) with an alkylating agent:

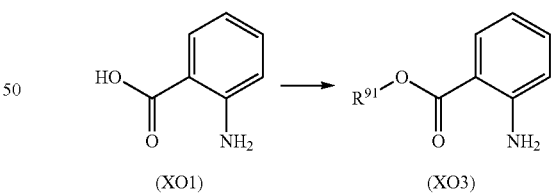

wherein $R^{91}$ is the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the alkylating agent to be usable in the reaction include diazo compounds such as diazomethane and trimethylsilyldiazomethane; alkyl halides such as methyl bromide, ethyl bromide, n-propyl bromide, methyl iodide, ethyl iodide, allyl bromide, cyclopropyl bromide, benzyl bromide, and 1,1-difluoro-2-iodoethane; sulfuric acid esters such as dimethyl sulfate, diethyl sulfate, and di-n-propyl sulfate; and sulfonic acid esters such as methyl p-toluenesulfonate, ethyl p-toluenesulfonate, n-propyl p-toluenesulfonate, methyl methanesulfonate, ethyl methanesulfonate, and n-propyl methanesulfonate.

In the reaction, the alkylating agent is usually used in the proportion within a range of 1 to 10 mols based on 1 mol of the compound (XO1).

If necessary, additives may be added in the reaction and examples thereof include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; and quaternary ammonium salts such as tetra(n-butyl)ammonium hydroxide. These additives are usually used in the proportion within a range of 0.01 to 5 mols based on 1 mol of the compound (XO1).

The reaction temperature of the reaction is usually within a range of −78 to 100° C. The reaction time of the reaction is usually within a range of 0.1 to 24 hours.

After completion of the reaction, the compound (XO3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process R)

A compound represented by formula (XR2) (hereinafter referred to as the compound (XR2)) can be produced by reacting a compound represented by formula (XR1) (hereinafter referred to as the compound (XR1)) with a reducing agent:

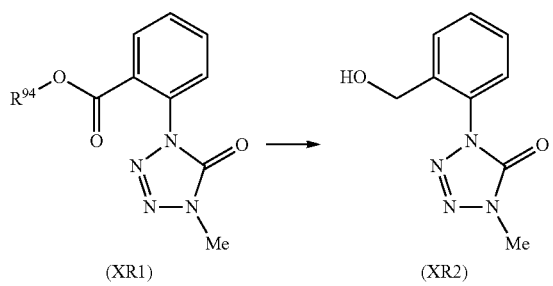

wherein $R^{94}$ represents a hydrogen atom or a C1-C3 alkyl group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; alcohols such as methanol, ethanol, propanol, and butanol; water; and mixtures thereof.

Examples of the reducing agent to be usable in the reaction include lithium triethylborohydride, aluminum diisobutylhydride, lithium aminoborohydride, lithium borohydride, sodium borohydride, borane, borane dimethyl sulfide complex, and borane tetrahydrofuran complex.

In the reaction, the reducing agent is usually used in the proportion within a range of 1 to 10 mols based on 1 mol of the compound (XR1).

The reaction temperature of the reaction is usually within a range of −78 to 100° C. The reaction time of the reaction is usually within a range of 0.1 to 24 hours.

After completion of the reaction, the compound (XR2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process S)

A compound represented by formula (XS2) (hereinafter referred to as the compound (XS2)) can be produced by reacting a compound represented by formula (XS1) (hereinafter referred to as the compound (XS1)) with a reducing agent:

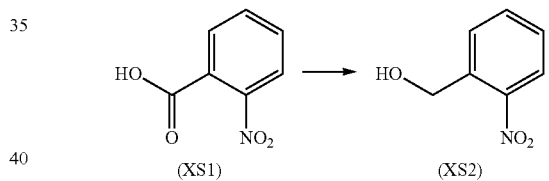

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; sulfoxides such as dimethyl sulfoxide; nitriles such as acetonitrile and propionitrile; alcohols such as methanol, ethanol, propanol, and butanol; water; and mixtures thereof.

Examples of the reducing agent to be usable in the reaction include borane, borane tetrahydrofuran complex, and borane dimethyl sulfide complex. It is also possible to use borane to be generated by mixing borohydrides such as sodium borohydride and potassium borohydride with acids such as sulfuric acid, hydrochloric acid, methanesulfonic acid, boron trifluoride diethyl ether complex, and dimethylsulfuric acid.

In the reaction, the reducing agent is usually used in the proportion within a range of 1 to 10 mols based on 1 mol of the compound (XS1).

The reaction temperature of the reaction is usually within a range of −20 to 100° C. The reaction time of the reaction is usually within a range of 0.1 to 72 hours.

After completion of the reaction, the compound (XS2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process T)

The compound (E-1) can be produced by reacting the compound (A-1) with a compound represented by formula (XT1) (hereinafter referred to as the compound (XT1)):

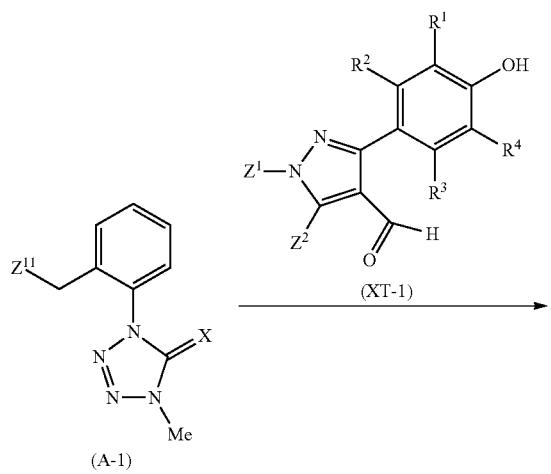

(A-1)

(XT-1)

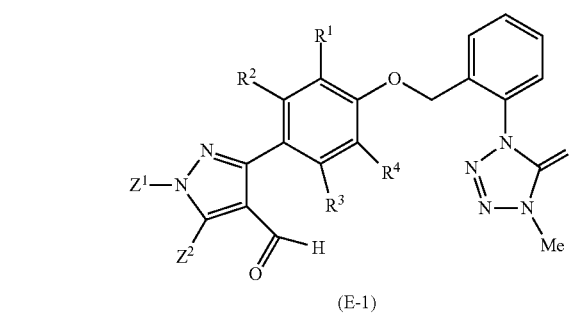

(E-1)

wherein $R^1$, $R^2$, $R^3$, $R^4$, X, $Z^1$, $Z^2$, and $Z^{11}$ are the same as defined above.

The reaction can be carried out in accordance with Production Process A.

(Reference Production Process U)

Among the compounds represented by formula (E-1), a compound represented by formula (U-3) in which $Z^2$ is $Z^{2H}$ (hereinafter referred to as the compound (U-3)) can be produced by reacting a compound represented by formula (U-1) in which $Z^2$ is a chlorine atom (hereinafter referred to as the compound (U-1)) with a compound represented by formula (U-2) (hereinafter referred to as the compound (U-2)) in the presence of a base:

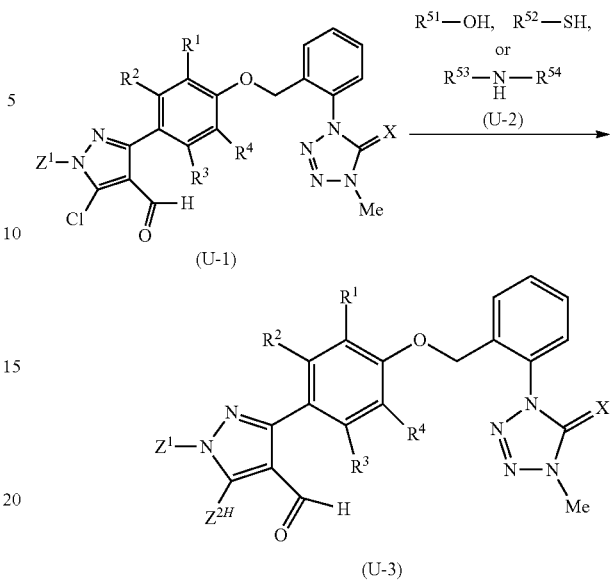

(U-1)

(U-3)

wherein $R^1$, $R^2$, $R^3$, $R^4$, X, and $Z^1$ are the same as defined above, $R^{51}$ represents an alkyl group optionally having a halogen atom, or a C3-C4 alkynyl group, $R^{52}$ represents an alkyl group optionally having a halogen atom, $R^{53}$ and $R^{54}$ each represents a C1-C3 alkyl group, and $Z^{2H}$ represents $OR^{51}$, $SR^{52}$, or $NR^{53}(R^{54})$.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof. It is also possible to use the compound (U-2) as the solvent.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (U-2) is usually used in the proportion within a range of 1 to 10 mols, and the base is usually used in the proportion within a range of 1 to 10 mols based on 1 mol of the compound (U-1).

The reaction temperature of the reaction is usually within a range of −20 to 150° C. The reaction time of the reaction is usually within a range of 0.1 to 24 hours.

A metal salt formed by the compound (U-2) and the base is prepared in advance, and the metal salt can also be used in the reaction. Examples of the metal salt to be usable include sodium methoxide, sodium ethoxide, sodium, sodium isopropoxide, potassium methoxide, potassium ethoxide, sodium thiomethoxide, and sodium propoxide thioethoxide.

In the reaction, the metal salt formed by the compound (U-2) and the base is usually used in the proportion within a range of 1 to 10 mols based on 1 mol of the compound (U-1).

After completion of the reaction, the compound (U-3) can be isolated by performing post-treatment operations such as extraction of the reaction mixture with an organic solvent, and drying and concentration of the organic layer. It is also possible to isolate the compound (U-3) by post-treatment operations such as filtration and concentration of the reaction mixture. The isolated compound can be further purified by chromatography, recrystallization, and the like.

(Reference Production Process V)

The compound (U-1) can be produced by reacting the compound (A-1) with a compound represented by formula (XV-1) (hereinafter referred to as the compound (XV-1)):

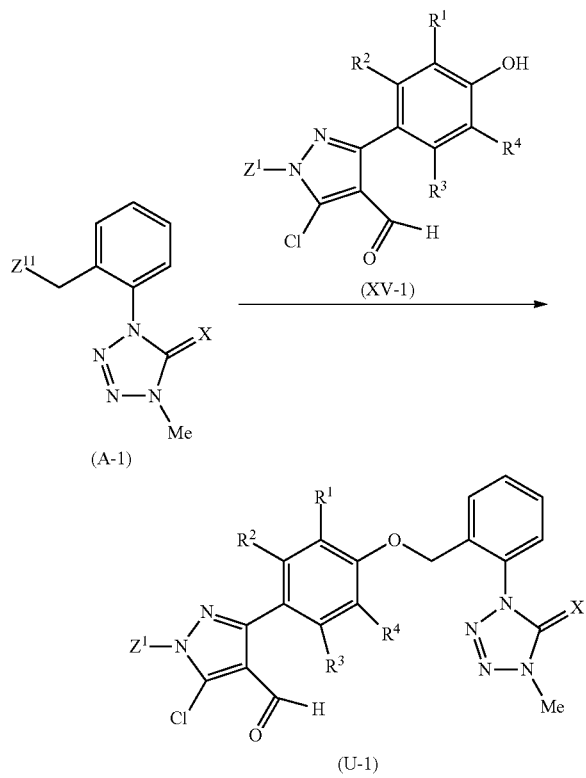

wherein $R^1$, $R^2$, $R^3$, $R^4$, X, $Z^1$, and $Z^{11}$ are the same as defined above.

The reaction can be carried out in accordance with Production Process A.

(Reference Production Process W)

A compound represented by formula (W-1) (hereinafter referred to as the compound (W-1)) can be produced by the compound (U-3) with hydroxylamines:

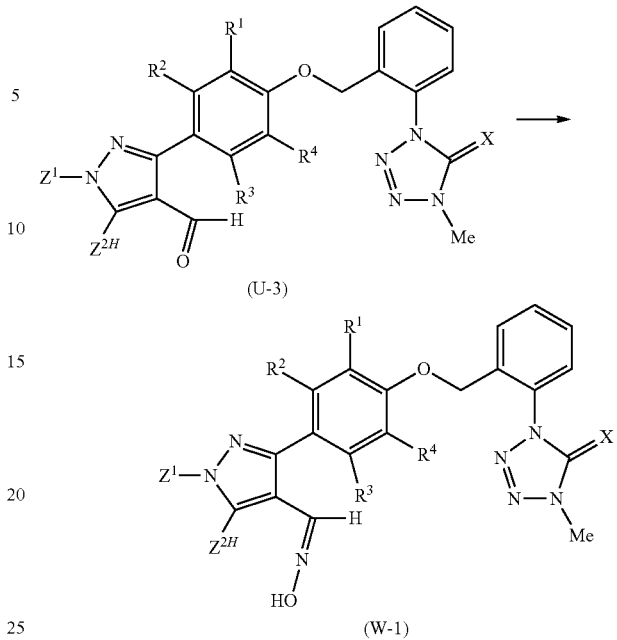

wherein $R^1$, $R^2$, $R^3$, $R^4$, X, $Z^1$, and $Z^{2H}$ are the same as defined above.

The reaction is usually performed in a solvent.

Examples of the solvent to be used in the reaction include hydrocarbons such as heptane, hexane, cyclohexane, pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of hydroxylamines include hydroxylamine hydrochloride, hydroxylamine sulfate, and aqueous hydroxylamine solution.

An acid may be used in the reaction, and examples of the acid to be used include acetic acid, hydrochloric acid, sulfuric acid, hydrobromic acid, hydrofluoric acid, and formic acid.

A base may be used in the reaction, and examples of the based to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium methoxide, sodium ethoxide, sodium tert-butoxide and potassium tert-butoxide.

In the reaction, hydroxylamines are usually used in the proportion within a range of 1 to 10 mols, and the acid and the base are usually used in the proportion within a range of 0.1 to 10 mols, based on 1 mol of the compound (U-3).

The reaction temperature of the reaction is usually within a range of −20 to 150° C. The reaction time of the reaction is usually within a range of 0.1 to 24 hours.

After completion of the reaction, the compound (W-1) can be isolated by performing post-treatment operations such as extraction of the reaction mixture with an organic solvent, and drying and concentration of the organic layer. The isolated compound can be further purified by chromatography, recrystallization, and the like.

(Reference Production Process AA)

The compound (A-2) can be produced by reacting a compound represented by formula (YA1) (hereinafter referred to as the compound (YA1)) with an acid:

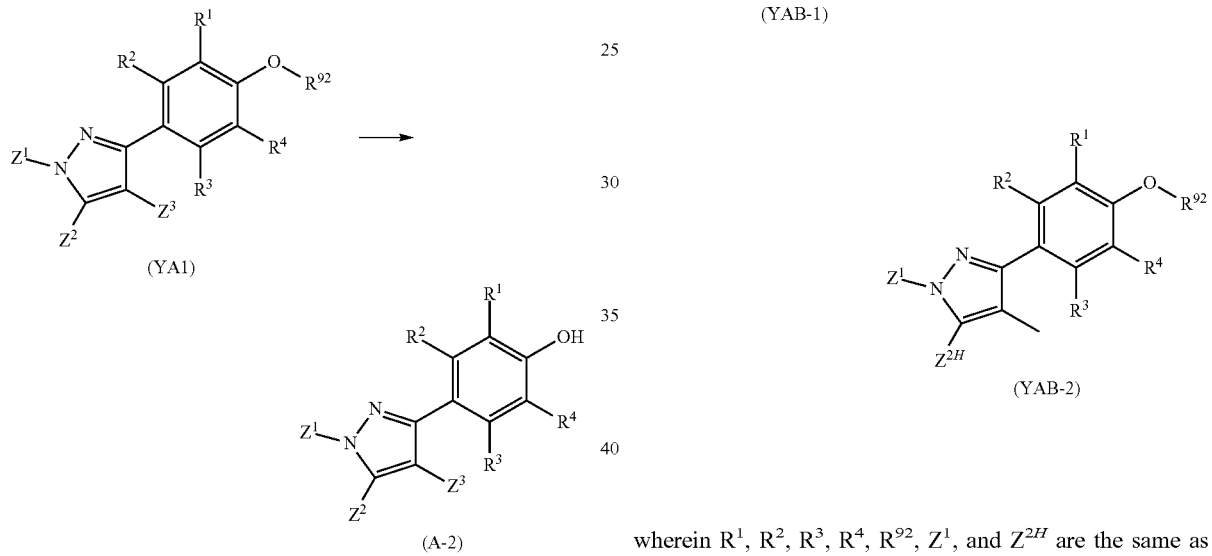

(YA1)

(A-2)

wherein $R^1$, $R^2$, $R^3$, $R^4$, $Z^1$, $Z^2$, and $Z^3$ are the same as defined above, and $R^{92}$ represents a C1-C5 alkyl group.

The reaction is usually performed in a solvent.

Examples of the solvent to be used in the reaction include alcohols such as methanol, ethanol, propanol, and butanol; water, acetic acid; and mixtures thereof.

Examples of the acid to be used in the reaction include acetic acid, hydrochloric acid, and hydrobromic acid. It is also possible to use aqueous solutions of thereof as the solvent.

In the reaction, the acid is usually used in a large excess amount based on 1 mol of the compound (YA1).

The reaction temperature of the reaction is usually within a range of −20 to 150° C. The reaction time of the reaction is usually within a range of 0.1 to 100 hours.

After completion of the reaction, the compound (A-2) can be isolated by performing post-treatment operations such as extraction of the reaction mixture with an organic solvent, and drying and concentration of the organic layer. It is also possible to isolate the compound (A-2) by performing post-treatment operations such as concentration of the reaction mixture. The isolated compound can be further purified by chromatography, recrystallization, and the like.

(Reference Production Process AB)

Among the compounds represented by formula (YA1), a compound represented by formula (YAB-2) in which $Z^2$ is $Z^{2H}$ and $Z^3$ is a methyl group (hereinafter referred to as the compound (YAB-2)) can be produced by reacting a compound represented by formula (YAB-1) (hereinafter referred to as the compound (YAB-1)) with a reducing agent in the presence of an acid:

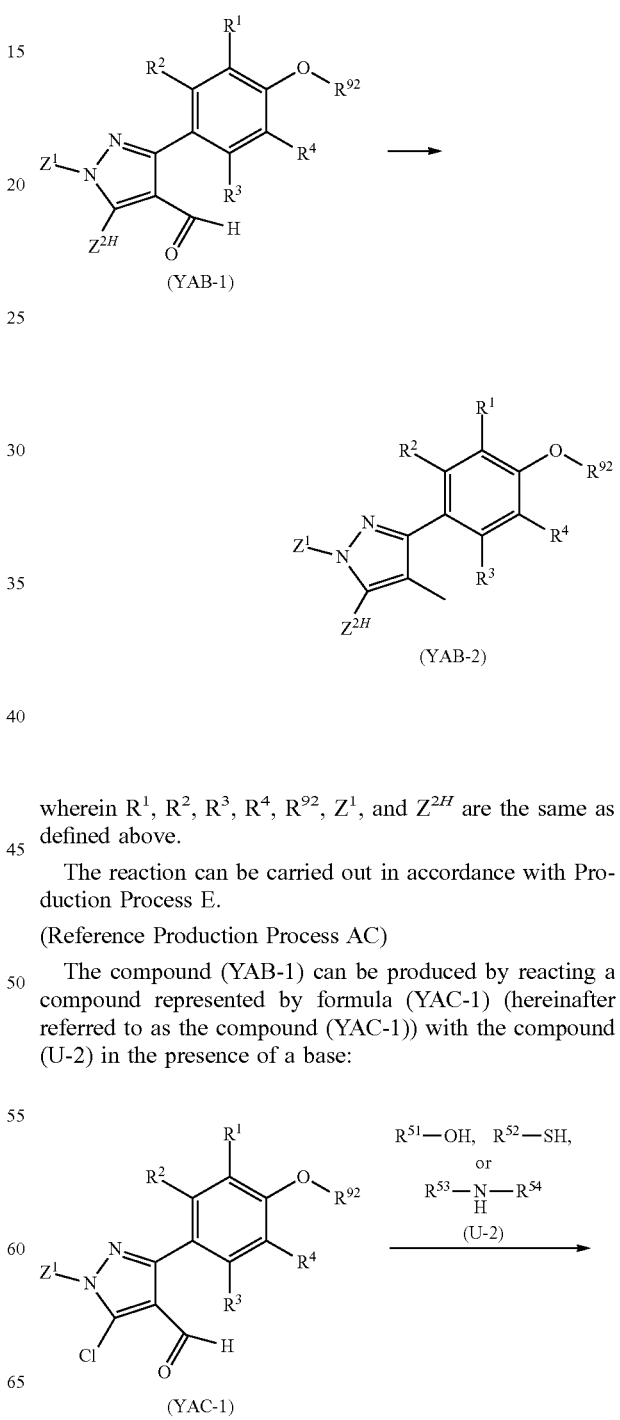

(YAB-1)

(YAB-2)

wherein $R^1$, $R^2$, $R^3$, $R^4$, $R^{92}$, $Z^1$, and $Z^{2H}$ are the same as defined above.

The reaction can be carried out in accordance with Production Process E.

(Reference Production Process AC)

The compound (YAB-1) can be produced by reacting a compound represented by formula (YAC-1) (hereinafter referred to as the compound (YAC-1)) with the compound (U-2) in the presence of a base:

(YAC-1)

-continued

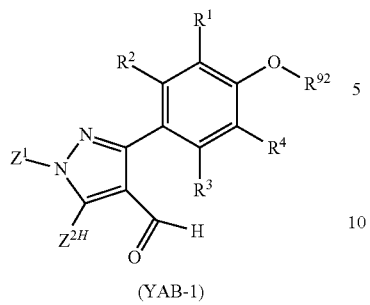

(YAB-1)

wherein $R^1$, $R^2$, $R^3$, $R^4$, $R^{51}$, $R^{52}$, $R^{53}$, $R^{54}$, $R^{92}$, $Z^1$, and $Z^{2H}$ are the same as defined above.

The reaction can be carried out in accordance with Production Process U.

(Reference Production Process AD)

Among the compounds (YAC-1), a compound represented by formula (YAC-1-1) in which $R^{92}$ is an isopropyl group (hereinafter referred to as the compound (YAC-1-1)), a compound represented by formula (YAD-2) (hereinafter referred to as the compound (YAD-2)), and a compound represented by formula (XV-1) (hereinafter referred to as the compound (XV-1)) can be produced by reacting a compound represented by formula (YAD-1) (hereinafter referred to as the compound (YAD-1)) with a formylating agent prepared from N,N-dimethylformamide and phosphorus oxychloride, and reacting the reaction product with water:

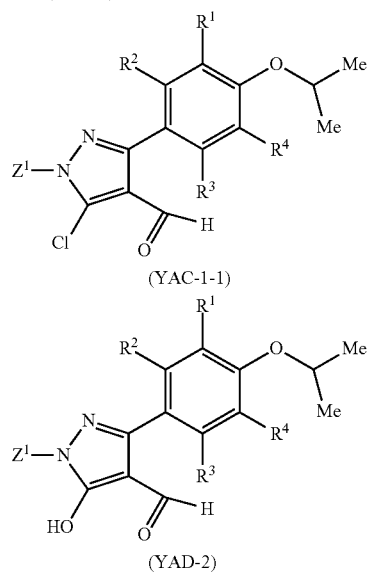

(YAD-1)

(YAC-1-1)

(YAD-2)

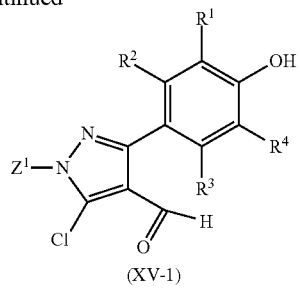

(XV-1)

wherein $R^1$, $R^2$, $R^3$, $R^4$, and $Z^1$ are the same as defined above.

The reaction is usually performed in a solvent.

Examples of the solvent to be used in the reaction include hydrocarbons such as n-heptane, n-hexane, cyclohexane, and n-pentane; ethers such as diethyl ether, tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof.

In the reaction, a mixture of 1 to 10 mols of N,N-dimethylformamide and 1 to 10 mols of phosphorus oxychloride is used as the formylating agent, and water is used in the proportion within a range of 1 to 10 mols, based on 1 mol of the compound (YAD-1).

The reaction temperature of the reaction is usually within a range of −20 to 150° C. The reaction time of the reaction is usually within a range of 0.1 to 24 hours.

After completion of the reaction, the compound (YAC-1-1), the compound (YAD-2), and the compound (XV-1) can be usually obtained by performing post-treatment operations such as addition of 1 mol or more of water, extraction of the reaction mixture with an organic solvent, and drying and concentration of the organic layer. The isolated present compound may be further purified by chromatography, recrystallization, and the like.

(Reference Production Process AE)

A compound represented by formula (YAE-2) (hereinafter referred to as the compound (YAE-2)) can be produced by reacting a compound represented by formula (YAE-1) (hereinafter referred to as the compound (YAE-1)) with the compound (AE1):

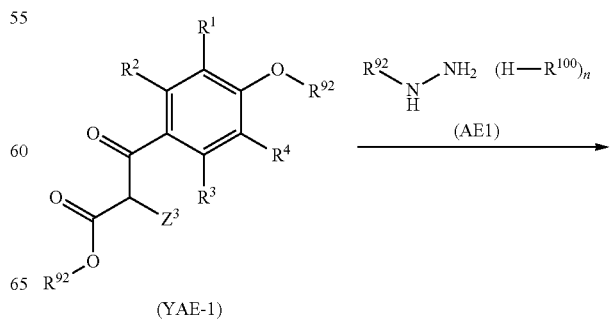

(YAE-1)

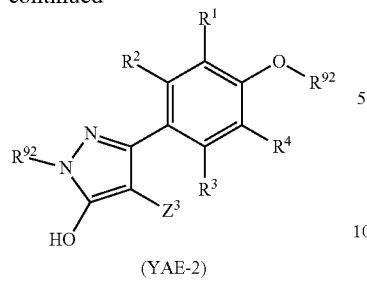

(YAE-2)

wherein $R^1$, $R^2$, $R^3$, $R^4$, $R^{92}$, $R^{100}$, and $Z^3$ are the same as defined above, and n represents 0 or 1.

The reaction is performed in a solvent, or in the absence of a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile and propionitrile; water; and mixtures thereof.

If necessary, an acid may be added in the reaction, and examples of the acid to be used in the reaction include hydrochloric acid, sulfuric acid, acetic acid, hydrobromic acid, and p-toluenesulfonic acid.

In the reaction, the compound (AE1) is usually used in the proportion within a range of 1 to 100 mols, and the acid is usually used in the proportion within a range of 1 to 100 mols, based on 1 mol of the compound (YAE-1).

The reaction temperature of the reaction is usually within a range of −20 to 150° C. The reaction time of the reaction is usually within a range of 0.1 to 24 hours.

After completion of the reaction, the compound (YAE-2) can be isolated by performing post-treatment operations such as concentration of the reaction mixture under reduced pressure, extraction of the reaction mixture with an organic solvent, and drying and concentration of the organic layer. The isolated present compound may be further purified by chromatography, recrystallization, and the like.

(Reference Production Process AF)

The compound (YAE-1) can be produced by reacting a compound represented by formula (YAF-1) (hereinafter referred to as the compound (YAF-1)) with a compound represented by formula (AF1) (hereinafter referred to as the compound (AF1)) in the presence of a base:

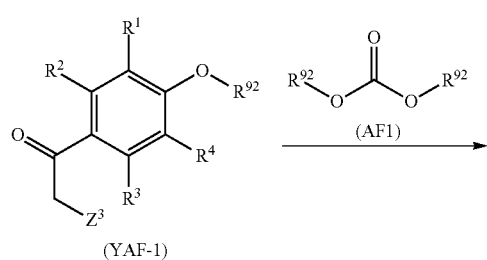

(YAF-1)

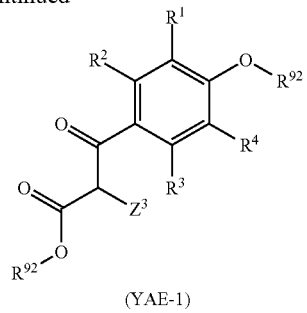

(YAE-1)

wherein $R^1$, $R^2$, $R^3$, $R^4$, $R^{92}$, and $Z^3$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (AF1) is usually used in the proportion within a range of 1 to 10 mols, and the base is usually used in the proportion within a range of 1 to 10 mols, based on 1 mol of the compound (YAF-1).

The reaction temperature of the reaction is usually within a range of −20 to 150° C. The reaction time of the reaction is usually within a range of 0.1 to 24 hours.

If necessary, additives may be added in the reaction, and examples thereof include 18-crown-6-ether and dibenzo-18-crown-6-ether. These additives are usually used in the proportion within a range of 0.001 to 1.2 mols based on 1 mol of the compound (YAF-1).

After completion of the reaction, the compound (YAE-1) can be isolated by performing post-treatment operations such as extraction of the reaction mixture with an organic solvent, and drying and concentration of the organic layer. The isolated present compound can be further purified by chromatography, recrystallization, and the like.

(Reference Production Process AG)

The compound (YAF-1) can be produced by reacting a compound represented by formula (YAG-1) (hereinafter referred to as the compound (YAG-1)) with a compound represented by formula (AG1) (hereinafter referred to as the compound (AG1)) in the presence of a base:

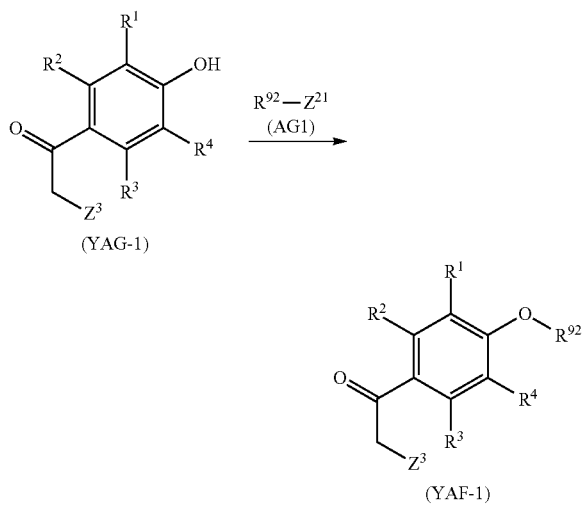

wherein $R^1$, $R^2$, $R^3$, $R^4$, $R^{92}$, $Z^3$, and $Z^{21}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (AG1) is usually used in the proportion within a range of 1 to 10 mols, and the base is usually used in the proportion within a range of 1 to 10 mols, based on 1 mol of the compound (YAG-1).

The reaction temperature of the reaction is usually within a range of −20 to 150° C. The reaction time of the reaction is usually within a range of 0.1 to 24 hours.

After completion of the reaction, the compound (YAF-1) can be isolated by performing post-treatment operations such as extraction of the reaction mixture with an organic solvent, and drying and concentration of the organic layer. The isolated present compound can be further purified by chromatography, recrystallization, and the like.

(Reference Production Process AH)

The compound (YAG-1) can be produced by reacting a compound represented by formula (YAH-1) (hereinafter referred to as the compound (YAH-1)) in the presence of an acid catalyst:

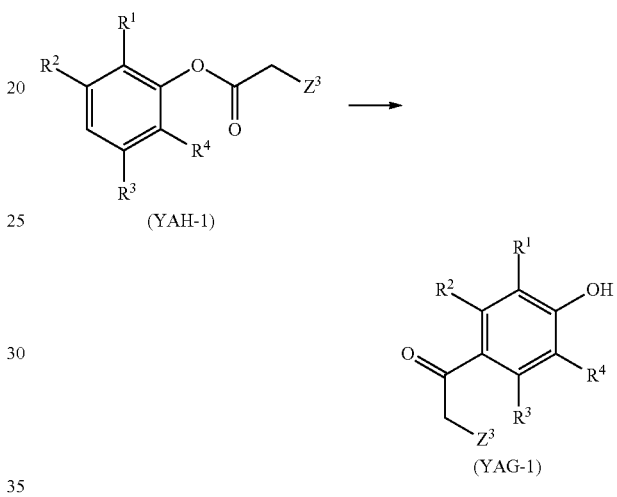

wherein $R^1$, $R^2$, $R^3$, $R^4$, and $Z^3$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitromethane, nitriles such as acetonitrile and propionitrile; and mixtures thereof.

Examples of the acid catalyst to be used in the reaction include aluminum trichloride, titanium tetrachloride, iron trichloride, hydrogen fluoride, hypochlorous acid, and polyphosphoric acid.

In the reaction, a rearrangement reaction agent is usually used in the proportion within a range of 1 to 10 mols based on 1 mol of the compound (YAH-1).

The reaction temperature of the reaction is usually within a range of −20 to 150° C. The reaction time of the reaction is usually within a range of 0.1 to 72 hours.

After completion of the reaction, the compound (YAG-1) can be isolated by performing post-treatment operations such as extraction of the reaction mixture with an organic solvent, and drying and concentration of the organic layer. The isolated present compound can be further purified by chromatography, recrystallization, and the like.

(Reference Production Process AI)

The compound (YAH-1) can be produced by reacting a compound represented by formula (YAI-1) (hereinafter referred to as the compound (YAI-1)) with a compound represented by formula (AI1) (hereinafter referred to as the compound (AI1)) in the presence of a base:

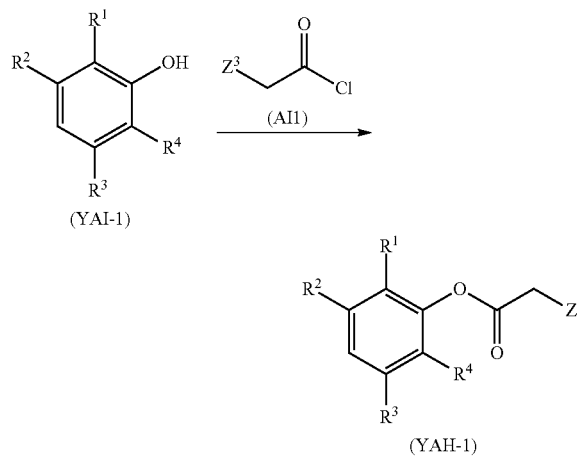

wherein $R^1$, $R^2$, $R^3$, $R^4$, and $Z^3$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile and propionitrile; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (AI1) is usually used in the proportion within a range of 1 to 10 mols, and the base is usually used in the proportion within a range of 1 to 10 mols, based on 1 mol of the compound (YAI-1).

The reaction temperature of the reaction is usually within a range of −78 to 150° C. The reaction time of the reaction is usually within a range of 0.1 to 72 hours.

After completion of the reaction, the compound (YAH-1) can be isolated by performing post-treatment operations such as extraction of the reaction mixture with an organic solvent, and drying and concentration of the organic layer. The isolated present compound can be further purified by chromatography, recrystallization, and the like.

(Reference Production Process AJ)

A compound represented by formula (YAJ-2) (hereinafter referred to as the compound (YAJ-2)) can be produced by reacting a compound represented by formula (YAJ-1) (hereinafter referred to as the compound (YAJ-1)) with a halogenating agent:

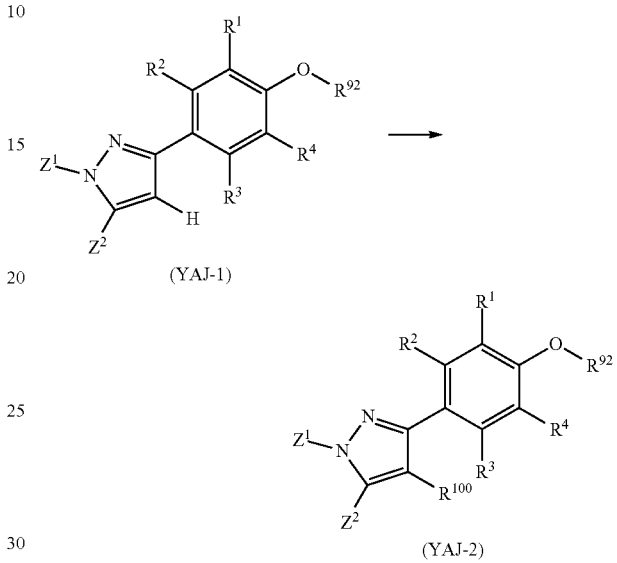

wherein $R^1$, $R^2$, $R^3$, $R^4$, $R^{92}$, $R^{100}$, $Z^1$, and $Z^2$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; and mixtures thereof.

Examples of the halogenating agent to be used in the reaction include fluorine, chlorine, bromine, iodine, 1-chloromethyl-4-fluoro-1,4-diazoniabicyclo[2,2,2]octane-bis(tetrafluoroborate), N-chlorosuccinimide, N-bromosuccinimide, N-iodosuccinimide, and sulfuryl chloride.

In the reaction, the halogenating agent is usually used in the proportion within a range of 1 to 10 mols based on 1 mol of the compound (YAJ-1).

The reaction temperature of the reaction is usually within a range of −20 to 150° C. The reaction time of the reaction is usually within a range of 0.1 to 24 hours.

After completion of the reaction, the compound (YAJ-2) can be isolated by performing post-treatment operations such as extraction of the reaction mixture with an organic solvent, and drying and concentration of the organic layer. The isolated compound (YAJ-2) may be further purified by operations such as chromatography and recrystallization.

(Reference Production Process AK)

A compound represented by formula (YAK-1) (hereinafter referred to as the compound (YAK-1)) can be produced by reacting the compound (YE-2) with an alkylating agent in the presence of a base:

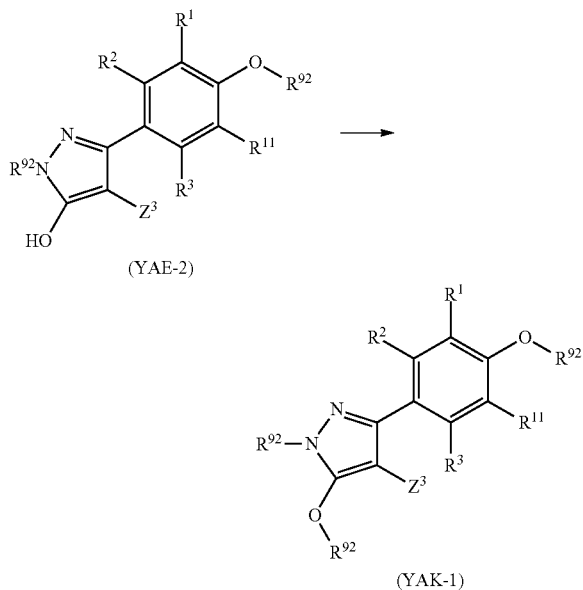

(YAE-2)

(YAK-1)

wherein $R^1$, $R^2$, $R^3$, $R^{11}$, $R^{92}$, and $Z^3$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

The alkylating agent to be used in the reaction can be usually commercially available alkylating agents. Examples thereof include alkyl halides such as methyl bromide, ethyl bromide, n-propyl bromide, n-butyl bromide, n-pentyl bromide, methyl iodide, ethyl iodide, n-propyl iodide, isopropyl iodide, and isobutyl iodide; sulfuric acid esters such as dimethyl sulfate; and sulfonic acid esters such as methyl p-toluenesulfonate, ethyl p-toluenesulfonate, n-propyl p-toluenesulfonate, methyl methanesulfonate, ethyl methanesulfonate, and n-propyl methanesulfonate. Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the alkylating agent is usually used in the proportion within a range of 1 to 10 mols, and the base is usually used in the proportion within a range of 1 to 10 mols, based on 1 mol of the compound (YE-2).

The reaction temperature of the reaction is usually within a range of −20 to 150° C. The reaction time of the reaction is usually within a range of 0.1 to 24 hours.

After completion of the reaction, the compound (YAK-1) can be isolated by performing post-treatment operations such as extraction of the reaction mixture with an organic solvent, and drying and concentration of the organic layer. The isolated present compound may be further purified by chromatography, recrystallization, and the like.

Although a form used for the present compound may be the present compound as itself, the present compound is usually prepared by mixing the present compound with solid carriers, liquid carriers, gas carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carrier include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexane, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyethylene glycol ethers, polyol esters, and sugar alcohol derivatives.

Examples of other auxiliary agents for formulation include stickers, dispersers, and stabilizers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof, and the like.

The present compound may be used in admixture with various oils or surfactants such as mineral oils or vegetable oils. Specific examples of oils or surfactants, which can be used as a mixture, include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANGLE (registered trademark), and the like.

The present control agent can also be used as a mixture with or together with other fungicides, insecticides, acaricides, nematicides, and plant growth regulators.

Examples of these other fungicides include the followings:

(1) Azole fungicides
such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, simeconazole, and ipconazole;
(2) Amine fungicides
such as fenpropimorph, tridemorph, fenpropidin, and spiroxamine;
(3) Benzimidazole fungicides
such as carbendazim, benomyl, thiabendazole, and thiophanate-methyl;
(4) Dicarboximide fungicides
such as procymidone, iprodione, and vinclozolin;
(5) Anilinopyridine fungicides
such as cyprodinil, pyrimethanil, and mepanipyrim;
(6) Phenylpyrrole fungicides
such as fenpiclonil and fludioxonil;
(7) Strobilurin fungicides
such as kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin, pyrametostrobin, flufenoxystrobin, fenaminstrobin, enoxastrobin, coumoxystrobin, pyriminostrobin, triclopyricarb, and mandestrobin;
(8) Phenylamide fungicides
such as metalaxyl, metalaxyl-M or mefenoxam, benalaxyl, and benalaxyl-M or kiralaxyl;
(9) Carboxylic acid amide fungicides
such as dimethomorph, iprovalicarb, benthivalicarb-isopropyl, mandipropamid, and valiphenal;
(10) Carboxamide fungicides
such as carboxin, mepronil, flutolanil, thifluzamide, furametpyr, boscalid, penthiopyrad, fluopyram, bixafen, penflufen, sedaxane, fluxapyroxad, isopyrazam, benzovindiflupyr, isofetamid, N-[2-(3,4-difluorophenyl)phenyl]-3-trifluoromethylpyrazine-2-carboxylic acid amide, N-(1,1,3-trimethylindan-4-yl)-1-methyl-3-difluoromethylpyrazole-4-carboxylic acid amide (including racemate or enantiomer, a mixture of enantiomer of R form and enantiomer of S form at an optional ratio); and
(11) Other fungicides
such as diethofencarb, thiuram, fluazinam, mancozeb, chlorothalonil, captan, dichlofluanid, folpet, quinoxyfen, fenhexanid, fanoxadon, fenamidon, zoxamide, thaboxam, amisulbrom, cyazofamid, metrafenone, pyriofenone, cyflufenamid, proquinazid, flusulfamide, fluopicolide, fosetyl, cymoxanil, pencycuron, tolclofos-methyl, carpropamid, diclocymet, fenoxanil, tricyclazole, pyroquilon, probenazole, isotianil, tiadinil, tebufloquin, clomezine, kasugamycin, ferimzone, fthalide, validamycin, hydroxyisoxazole, iminoctadine acetate, isoprothiolane, oxolinic acid, oxytetracycline, streptomycin, copper oxychloride, copper hydroxide, opper hydroxide sulfate, organocopper, sulfur, ametoctradin, fenpyrazamine, oxathiapiprolin, 3-chloro-4-(2,6-difluorophenyl)-6-methyl-5-phenylpyridazine, and 3-cyano-4-(2,6-difluorophenyl)-6-methyl-5-phenylpyridazine.

Examples of these other insecticides include:
(1) Organophosphorus compounds
such as acephate, aluminium phosphide, butathiofos, cadusafos, chlorethoxyfos, chlorfenvinphos, chlorpyrifos, chlorpyrifos-methyl, cyanophos:CYAP, diazinon, dichlorodiisopropyl ether (DCIP), dichlofenthion:ECP, dichlorvos:DDVP, dimethoate, dimethylvinphos, disulfoton, EPN, ethion, ethoprophos, etrimfos, fenthion:MPP, fenitrothion:MEP, fosthiazate, formothion, hydrogen phosphide, isofenphos, isoxathion, malathion, mesulfenfos, methidathion:D-MTP, monocrotophos, naled:BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, vamidothion, phorate, and cadusafos;
(2) Carbamate compounds
such as alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, xylylcarb, and aldicarb;
(3) Synthetic pyrethroid compounds
such as acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, beta-cypermethrin, theta-cypermethrin, zeta-cypermethrin, lambda-cyhalothrin, gamma-cyhalothrin, furamethrin, tau-fluvalinate, halfenprox, protrifenbute, 2,3,5,6-tetrafluoro-4-(methoxymethyl)benzyl(EZ)-(1RS,3RS;1RS,3SR)-2,2-dimethyl-3-prop-1-enylcyclopropanecarboxylate, 2,3,5,6-tetrafluoro-4-methylbenzyl(EZ)-(1RS,3RS;1RS,3SR)-2,2-dimethyl-3-prop-1-enylcyclopropanecarboxylate, and 2,3,5,6-tetrafluoro-4-(methoxymethyl)benzyl(1RS,3RS;1RS,3SR)-2,2-dimethyl-3-(2-methyl-1-propenyl)cyclopropanecarboxylate;
(4) Nereistoxin compounds
such as cartap, bensultap, thiocyclam, monosultap, and bisultap;
(5) Neonicotinoid compounds
such as imidacloprid, nitenpyram, acetamiprid, thiamethoxam, thiacloprid, dinotefuran, and clothianidin;
(6) Benzoylurea compounds
such as chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron;
(7) Phenylpyrazole compounds
such as acetoprole, ethiprole, fipronil, vaniliprole, pyriprole, and pyrafluprole;
(8) Bt toxin insecticides
such as live spores derived from and crystal toxins produced from *Bacillus thuringiesis*, and a mixture thereof;

(9) Hydrazine compounds
such as chromafenozide, halofenozide, methoxyfenozide, and tebufenozide;
(10) Organochlorine compounds
such as aldrin, dieldrin, dienochlor, endosulfan, and methoxychlor;
(11) Natural insecticides
such as machine oil and nicotine-sulfate; and
(12) Other insecticides
such as avermectin-B, bromopropylate, buprofezin, chlorphenapyr, cyromazine, 1,3-dichloropropene (D-D), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, doramectin, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, spiromesifen, sulfur, metaflumizone, spirotetramat, pyrifluquinazone, spinetoram, chlorantraniliprole, cyantraniliprole, cyclaniliprole, sulfoxaflor, and flupyradifurone.

Examples of these other acaricides (acaricidally active ingredients) include acequinocyl, amitraz, benzoximate, bifenaate, bromopropylate, chinomethionat, chlorobenzilate, chlorfenson (CPCBS), clofentezine, cyflumetofen, dicofol (kelthane), etoxazole, fenbutatin oxide, fenothiocarb, fenpyroximate, fluacrypyrim, fluproxyfen, hexythiazox, propargite:BPPS, polynactins, pyridaben, pyrimidifen, tebufenpyrad, tetradifon, spirodiclofen, spiromesifen, spirotetramat, amidoflumet, and cyenopyrafen.

Examples of these other nematicides (nematicidally active ingredients) include DCIP, fosthiazate, levamisole hydrochloride, methyisothiocyanate, morantel tartarate, imicyafos, fluensulfone, and the like.

Examples of these other plant growth regulators include: ethephon, chlormequat-chloride, mepiquat-chloride, gibberellin A typified by gibberellin A3, abscisic acid, kinetin, benzyladenine, 1,3-diphenylurea, forchlorfenuron, thidiazuron, 4-oxo-4-(2-phenylethyl)aminobutyric acid, methyl 5-(trifluoromethyl)benzo[b]thiophene-2-carboxylate, 5-(trifluoromethyl)benzo[b]thiophene-2-carboxylic acid, and the like.

More specifically, the present compound can be used in the following aspects including:
a pest control composition comprising any one of the present compounds 1 to 10, and prothioconazole at a ratio of 0.1:1;
a pest control composition comprising any one of the present compounds 1 to 10, and prothioconazole at a ratio of 1:1;
a pest control composition comprising any one of the present compounds 1 to 10, and prothioconazole at a ratio of 10:1;
a pest control composition comprising any one of the present compounds 1 to 10, and bromuconazole at a ratio of 0.1:1;
a pest control composition comprising any one of the present compounds 1 to 10, and bromuconazole at a ratio of 1:1;
a pest control composition comprising any one of the present compounds 1 to 10, and bromuconazole at a ratio of 10:1;
a pest control composition comprising any one of the present compounds 1 to 10, and metconazole at a ratio of 0.1:1;
a pest control composition comprising any one of the present compounds 1 to 10, and metconazole at a ratio of 1:1;
a pest control composition comprising any one of the present compounds 1 to 10, and metconazole at a ratio of 10:1;
a pest control composition comprising any one of the present compounds 1 to 10, and tebuconazole at a ratio of 0.1:1;
a pest control composition comprising any one of the present compounds 1 to 10, and tebuconazole at a ratio of 1:1;
a pest control composition comprising any one of the present compounds 1 to 10, and tebuconazole at a ratio of 10:1;
a pest control composition comprising any one of the present compounds 1 to 10, and tetraconazole at a ratio of 0.1:1;
a pest control composition comprising any one of the present compounds 1 to 10, and tetraconazole at a ratio of 1:1;
a pest control composition comprising any one of the present compounds 1 to 10, and tetraconazole at a ratio of 10:1;
a pest control composition comprising any one of the present compounds 1 to 10, and cyproconazole at a ratio of 0.1:1;
a pest control composition comprising any one of the present compounds 1 to 10, and cyproconazole at a ratio of 1:1;
a pest control composition comprising any one of the present compounds 1 to 10, and cyproconazole at a ratio of 10:1;
a pest control composition comprising any one of the present compounds 1 to 10, and flusilazole at a ratio of 0.1:1;
a pest control composition comprising any one of the present compounds 1 to 10, and flusilazole at a ratio of 1:1;
a pest control composition comprising any one of the present compounds 1 to 10, and flusilazole at a ratio of 10:1;
a pest control composition comprising any one of the present compounds 1 to 10, and prochloraz at a ratio of 0.1:1;
a pest control composition comprising any one of the present compounds 1 to 10, and prochloraz at a ratio of 1:1;
a pest control composition comprising any one of the present compounds 1 to 10, and prochloraz at a ratio of 10:1;
a pest control composition comprising any one of the present compounds 1 to 10, and azoxystrobin at a ratio of 0.1:1;
a pest control composition comprising any one of the present compounds 1 to 10, and azoxystrobin at a ratio of 1:1;
a pest control composition comprising any one of the present compounds 1 to 10, and azoxystrobin at a ratio of 10:1;
a pest control composition comprising any one of the present compounds 1 to 10, and pyraclostrobin at a ratio of 0.1:1;
a pest control composition comprising any one of the present compounds 1 to 10, and pyraclostrobin at a ratio of 1:1;
a pest control composition comprising any one of the present compounds 1 to 10, and pyraclostrobin at a ratio of 10:1;
a pest control composition comprising any one of the present compounds 1 to 10, and picoxystrobin at a ratio of 0.1:1;
a pest control composition comprising any one of the present compounds 1 to 10, and picoxystrobin at a ratio of 1:1;
a pest control composition comprising any one of the present compounds 1 to 10, and picoxystrobin at a ratio of 10:1;
a pest control composition comprising any one of the present compounds 1 to 10, and fluoxastrobin at a ratio of 0.1:1;
a pest control composition comprising any one of the present compounds 1 to 10, and fluoxastrobin at a ratio of 1:1;
a pest control composition comprising any one of the present compounds 1 to 10, and fluoxastrobin at a ratio of 10:1;
a pest control composition comprising any one of the present compounds 1 to 10, and trifloxystrobin at a ratio of 0.1:1;
a pest control composition comprising any one of the present compounds 1 to 10, and trifloxystrobin at a ratio of 1:1;
a pest control composition comprising any one of the present compounds 1 to 10, and trifloxystrobin at a ratio of 10:1;
a pest control composition comprising any one of the present compounds 1 to 10, and mandestrobin at a ratio of 0.1:1;
a pest control composition comprising any one of the present compounds 1 to 10, and mandestrobin at a ratio of 1:1;
a pest control composition comprising any one of the present compounds 1 to 10, and mandestrobin at a ratio of 10:1;
a pest control composition comprising any one of the present compounds 1 to 10, and fluoxastrobin at a ratio of 0.1:1;
a pest control composition comprising any one of the present compounds 1 to 10, and fluoxastrobin at a ratio of 1:1;

a pest control composition comprising any one of the present compounds 1 to 10, and fluoxastrobin at a ratio of 10:1;
a pest control composition comprising any one of the present compounds 1 to 10, and bixafen at a ratio of 0.1:1;
a pest control composition comprising any one of the present compounds 1 to 10, and bixafen at a ratio of 1:1;
a pest control composition comprising any one of the present compounds 1 to 10, and bixafen at a ratio of 10:1;
a pest control composition comprising any one of the present compounds 1 to 10, and isopyrazam at a ratio of 0.1:1;
a pest control composition comprising any one of the present compounds 1 to 10, and isopyrazam at a ratio of 1:1;
a pest control composition comprising any one of the present compounds 1 to 10, and isopyrazam at a ratio of 10:1;
a pest control composition comprising any one of the present compounds 1 to 10, and fluopyram at a ratio of 0.1:1;
a pest control composition comprising any one of the present compounds 1 to 10, and fluopyram at a ratio of 1:1;
a pest control composition comprising any one of the present compounds 1 to 10, and fluopyram at a ratio of 10:1;
a pest control composition comprising any one of the present compounds 1 to 10, and penthiopyrad at a ratio of 0.1:1;
a pest control composition comprising any one of the present compounds 1 to 10, and penthiopyrad at a ratio of 1:1;
a pest control composition comprising any one of the present compounds 1 to 10, and penthiopyrad at a ratio of 10:1;
a pest control composition comprising any one of the present compounds 1 to 10, and benzovindiflupyr at a ratio of 0.1:1;
a pest control composition comprising any one of the present compounds 1 to 10, and benzovindiflupyr at a ratio of 1:1;
a pest control composition comprising any one of the present compounds 1 to 10, and benzovindiflupyr at a ratio of 10:1;
a pest control composition comprising any one of the present compounds 1 to 10, and fluxapyroxad at a ratio of 0.1:1;
a pest control composition comprising any one of the present compounds 1 to 10, and fluxapyroxad at a ratio of 1:1;
a pest control composition comprising any one of the present compounds 1 to 10, and fluxapyroxad at a ratio of 10:1;
a pest control composition comprising any one of the present compounds 1 to 10, and boscalid at a ratio of 0.1:1;
a pest control composition comprising any one of the present compounds 1 to 10, and boscalid at a ratio of 1:1;
a pest control composition comprising any one of the present compounds 1 to 10, and boscalid at a ratio of 10:1;
a pest control composition comprising any one of the present compounds 1 to 10, and N-[2-(3,4-difluorophenyl)phenyl]-3-trifluoromethylpyrazine-2-carboxylic acid amide at a ratio of 0.1:1;
a pest control composition comprising any one of the present compounds 1 to 10, and N-[2-(3,4-difluorophenyl)phenyl]-3-trifluoromethylpyrazine-2-carboxylic acid amide at a ratio of 1:1;
a pest control composition comprising any one of the present compounds 1 to 10, and N-[2-(3,4-difluorophenyl)phenyl]-3-trifluoromethylpyrazine-2-carboxylic acid amide at a ratio of 10:1;
a pest control composition comprising any one of the present compounds 1 to 10, and (R)-(−)-N-(1,1,3-trimethylindan-4-yl)-1-methyl-3-difluoromethylpyrazole-4-carboxylic acid amide at a ratio of 0.1:1;
a pest control composition comprising any one of the present compounds 1 to 10, and (R)-(−)-N-(1,1,3-trimethylindan-4-yl)-1-methyl-3-difluoromethylpyrazole-4-carboxylic acid amide at a ratio of 1:1;
a pest control composition comprising any one of the present compounds 1 to 10, and (R)-(−)-N-(1,1,3-trimethylindan-4-yl)-1-methyl-3-difluoromethylpyrazole-4-carboxylic acid amide at a ratio of 10:1;
a pest control composition comprising any one of the present compounds 1 to 10, and 3-chloro-4-(2,6-difluorophenyl)-6-methyl-5-phenylpyridazine at a ratio of 0.1:1;
a pest control composition comprising any one of the present compounds 1 to 10, and 3-chloro-4-(2,6-difluorophenyl)-6-methyl-5-phenylpyridazine at a ratio of 1:1;
a pest control composition comprising any one of the present compounds 1 to 10, and 3-chloro-4-(2,6-difluorophenyl)-6-methyl-5-phenylpyridazine at a ratio of 10:1;
a pest control composition comprising any one of the present compounds 1 to 10, and 3-cyano-4-(2,6-difluorophenyl)-6-methyl-5-phenylpyridazine at a ratio of 0.1:1;
a pest control composition comprising any one of the present compounds 1 to 10, and 3-cyano-4-(2,6-difluorophenyl)-6-methyl-5-phenylpyridazine at a ratio of 1:1;
a pest control composition comprising any one of the present compounds 1 to 10, and 3-cyano-4-(2,6-difluorophenyl)-6-methyl-5-phenylpyridazine at a ratio of 10:1;
a pest control composition comprising any one of the present compounds 1 to 10, and fenpropimorph at a ratio of 0.1:1;
a pest control composition comprising any one of the present compounds 1 to 10, and fenpropimorph at a ratio of 1:1;
a pest control composition comprising any one of the present compounds 1 to 10, and fenpropimorph at a ratio of 10:1;
a pest control composition comprising any one of the present compounds 1 to 10, and fenpropidin at a ratio of 0.1:1;
a pest control composition comprising any one of the present compounds 1 to 10, and fenpropidin at a ratio of 1:1;
a pest control composition comprising any one of the present compounds 1 to 10, and fenpropidin at a ratio of 10:1;
a pest control composition comprising any one of the present compounds 1 to 10, and spiroxamine at a ratio of 0.1:1;
a pest control composition comprising any one of the present compounds 1 to 10, and spiroxamine at a ratio of 1:1;
a pest control composition comprising any one of the present compounds 1 to 10, and spiroxamine at a ratio of 10:1;
a pest control composition comprising any one of the present compounds 1 to 10, and cyprodinil at a ratio of 0.1:1;
a pest control composition comprising any one of the present compounds 1 to 10, and cyprodinil at a ratio of 1:1;
a pest control composition comprising any one of the present compounds 1 to 10, and cyprodinil at a ratio of 10:1;
a pest control composition comprising any one of the present compounds 1 to 10, and pyrimethanil at a ratio of 0.1:1;
a pest control composition comprising any one of the present compounds 1 to 10, and pyrimethanil at a ratio of 1:1;
a pest control composition comprising any one of the present compounds 1 to 10, and pyrimethanil at a ratio of 10:1;
a pest control composition comprising any one of the present compounds 1 to 10, and fludioxonil at a ratio of 0.1:1;
a pest control composition comprising any one of the present compounds 1 to 10, and fludioxonil at a ratio of 1:1;
a pest control composition comprising any one of the present compounds 1 to 10, and fludioxonil at a ratio of 10:1;
a pest control composition comprising any one of the present compounds 1 to 10, and procymidone at a ratio of 0.1:1;
a pest control composition comprising any one of the present compounds 1 to 10, and procymidone at a ratio of 1:1;
a pest control composition comprising any one of the present compounds 1 to 10, and procymidone at a ratio of 10:1;
a pest control composition comprising any one of the present compounds 1 to 10, and iprodione at a ratio of 0.1:1;

a pest control composition comprising any one of the present compounds 1 to 10, and iprodione at a ratio of 1:1;
a pest control composition comprising any one of the present compounds 1 to 10, and iprodione at a ratio of 10:1;
a pest control composition comprising any one of the present compounds 1 to 10, and thiophanate-methyl at a ratio of 0.1:1;
a pest control composition comprising any one of the present compounds 1 to 10, and thiophanate-methyl at a ratio of 1:1;
a pest control composition comprising any one of the present compounds 1 to 10, and thiophanate-methyl at a ratio of 10:1;
a pest control composition comprising any one of the present compounds 1 to 10, and carbendazim at a ratio of 0.1:1;
a pest control composition comprising any one of the present compounds 1 to 10, and carbendazim at a ratio of 1:1;
a pest control composition comprising any one of the present compounds 1 to 10, and carbendazim at a ratio of 10:1;
a pest control composition comprising any one of the present compounds 1 to 10, and diethofencarb at a ratio of 0.1:1;
a pest control composition comprising any one of the present compounds 1 to 10, and diethofencarb at a ratio of 1:1;
a pest control composition comprising any one of the present compounds 1 to 10, and diethofencarb at a ratio of 10:1;
a pest control composition comprising any one of the present compounds 1 to 10, and fenpyrazamine at a ratio of 0.1:1;
a pest control composition comprising any one of the present compounds 1 to 10, and fenpyrazamine at a ratio of 1:1;
a pest control composition comprising any one of the present compounds 1 to 10, and fenpyrazamine at a ratio of 10:1;
a pest control composition comprising any one of the present compounds 1 to 10, and chlorothalonil at a ratio of 0.1:1;
a pest control composition comprising any one of the present compounds 1 to 10, and chlorothalonil at a ratio of 1:1;
a pest control composition comprising any one of the present compounds 1 to 10, and chlorothalonil at a ratio of 10:1;
a pest control composition comprising any one of the present compounds 1 to 10, and manzeb at a ratio of 0.1:1;
a pest control composition comprising any one of the present compounds 1 to 10, and manzeb at a ratio of 1:1;
a pest control composition comprising any one of the present compounds 1 to 10, and manzeb at a ratio of 10:1;
a pest control composition comprising any one of the present compounds 1 to 10, and folpet at a ratio of 0.1:1;
a pest control composition comprising any one of the present compounds 1 to 10, and folpet at a ratio of 1:1;
a pest control composition comprising any one of the present compounds 1 to 10, and folpet at a ratio of 10:1;
a pest control composition comprising any one of the present compounds 1 to 10, and metiram at a ratio of 0.1:1;
a pest control composition comprising any one of the present compounds 1 to 10, and metiram at a ratio of 1:1;
a pest control composition comprising any one of the present compounds 1 to 10, and metiram at a ratio of 10:1;
a pest control composition comprising any one of the present compounds 1 to 10, and clothianidin at a ratio of 1:1;
a pest control composition comprising any one of the present compounds 1 to 10, and clothianidin at a ratio of 1:10;
a pest control composition comprising any one of the present compounds 1 to 10, and clothianidin at a ratio of 1:50;
a pest control composition comprising any one of the present compounds 1 to 10, and imidacloprid at a ratio of 1:1;
a pest control composition comprising any one of the present compounds 1 to 10, and imidacloprid at a ratio of 1:10;
a pest control composition comprising any one of the present compounds 1 to 10, and imidacloprid at a ratio of 1:50;
a pest control composition comprising any one of the present compounds 1 to 10, and thiametoxam at a ratio of 1:1;
a pest control composition comprising any one of the present compounds 1 to 10, and thiametoxam at a ratio of 1:10;
a pest control composition comprising any one of the present compounds 1 to 10, and thiametoxam at a ratio of 1:50;
a pest control composition comprising any one of the present compounds 1 to 10, and dinotefuran at a ratio of 1:1;
a pest control composition comprising any one of the present compounds 1 to 10, and dinotefuran at a ratio of 1:10;
a pest control composition comprising any one of the present compounds 1 to 10, and dinotefuran at a ratio of 1:50;
a pest control composition comprising any one of the present compounds 1 to 10, and sulfoxaflor at a ratio of 1:1;
a pest control composition comprising any one of the present compounds 1 to 10, and sulfoxaflor at a ratio of 1:10;
a pest control composition comprising any one of the present compounds 1 to 10, and sulfoxaflor at a ratio of 1:50;
a pest control composition comprising any one of the present compounds 1 to 10, and chlorantraniliprole at a ratio of 1:1;
a pest control composition comprising any one of the present compounds 1 to 10, and chlorantraniliprole at a ratio of 1:10;
a pest control composition comprising any one of the present compounds 1 to 10, and chlorantraniliprole at a ratio of 1:50;
a pest control composition comprising any one of the present compounds 1 to 10, and cyantraniliprole at a ratio of 1:1;
a pest control composition comprising any one of the present compounds 1 to 10, and cyantraniliprole at a ratio of 1:10;
a pest control composition comprising any one of the present compounds 1 to 10, and cyantraniliprole at a ratio of 1:50;
a pest control composition comprising any one of the present compounds 1 to 10, and cyclaniliprole at a ratio of 1:1;
a pest control composition comprising any one of the present compounds 1 to 10, and cyclaniliprole at a ratio of 1:10;
a pest control composition comprising any one of the present compounds 1 to 10, and cyclaniliprole at a ratio of 1:50;
a pest control composition comprising any one of the present compounds 1 to 10, and abamectin at a ratio of 1:1;
a pest control composition comprising any one of the present compounds 1 to 10, and abamectin at a ratio of 1:10;
a pest control composition comprising any one of the present compounds 1 to 10, and abamectin at a ratio of 1:50;
a pest control composition comprising any one of the present compounds 1 to 10, and 4-oxo-4-(2-phenylethyl)aminobutyric acid at a ratio of 5:1;
a pest control composition comprising any one of the present compounds 1 to 10, and 4-oxo-4-(2-phenylethyl)aminobutyric acid at a ratio of 1:10;
a pest control composition comprising any one of the present compounds 1 to 10, and 4-oxo-4-(2-phenylethyl)aminobutyric acid at a ratio of 1:50;
a pest control composition comprising any one of the present compounds 1 to 10, and methyl 5-(trifluoromethyl)benzo[b]thiophene-2-carbonate at a ratio of 5:1;
a pest control composition comprising any one of the present compounds 1 to 10, and methyl 5-(trifluoromethyl)benzo[b]thiophene-2-carbonate at a ratio of 1:10;
a pest control composition comprising any one of the present compounds 1 to 10, and methyl 5-(trifluoromethyl)benzo[b]thiophene-2-carbonate at a ratio of 1:50;
a pest control composition comprising any one of the present compounds 1 to 10, and 5-(trifluoromethyl)benzo[b]thiophene-2-carboxylic acid at a ratio of 5:1;
a pest control composition comprising any one of the present compounds 1 to 10, and 5-(trifluoromethyl)benzo[b]thiophene-2-carboxylic acid at a ratio of 1:10; and a pest control composition comprising any one of the present compounds 1 to 10, and 5-(trifluoromethyl)benzo[b]thiophene-2-carboxylic acid at a ratio of 1:50.

The method for applying the present control agent is not particularly limited, as long as the applying form is a form by which the present control agent may be applied substantially, and includes, for example, an application to plants such as a foliage application; an application to area for cultivating plants such as a submerged treatment; and an application to soil such as seed disinfection.

The application dose of the present control agent varies depending on weather conditions, dosage forms, timing of application, methods of application, areas to be applied, target diseases, target crops, and the like, and is usually within a range of 1 to 500 g, and preferably 2 to 200 g, per 1,000 $m^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound is usually within a range of 0.001 to 100 g, and preferably 0.01 to 50 g, per 1 kg of the seeds.

In the present invention, examples of the place where the pests live include paddy fields, fields, tea gardens, orchards, non-agricultural lands, houses, nursery trays, nursery boxes, nursery soils, and nursery bed.

Also, in another embodiment, for example, the present control agent can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, administration via injection subcutaneously, intramuscularly or intravenously. Examples of a method of the external administration include transdermal administration. Also, the present control agent can be ingested to a livestock animal so as to exterminate sanitary insects which occur in the excrement of the animal.

When the present control agent is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present control agent can be used as an agent for controlling plant diseases in agricultural lands such as fields, paddy fields, lawns, and orchards. The present control agent can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: olanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like;

Flowers:

Ornamental foliage plants:

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus cuspidate*); and the like.

The above-mentioned "plants" include genetically modified crops.

The pests which can be controlled by the present control agent include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), seeding blight caused by bacteria of the genus (*Rhizoctonia solani*), and take all disease (*Gaeumannomyces graminis*); Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and seeding blight caused by bacteria of the genus (*Rhizoctonia solani*); Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum gfaminicola*), gray leaf spot (*Cercospora zeaemaydis*), eyespot (*Kabatiella zeae*), and *phaeosphaeria* leaf spot (*Phaeosphaeria maydis*); Cotton diseases: anthracnose (*Colletotrichum gossypii*), grey mildew (*Ramuraria areola*), and *alternaria* leaf spot (*Alternaria macrospora, A. gossypii*); Coffee diseases: rust (*Hemileia vastatrix*); Rape seed diseases: sclerotinia rot (*Sclerotinia sclerotiorum*), black spot (*Alternaria brassicae*), and black leg (*Phoma lingam*); Citrus diseases: melanose (*Diaporthe citri*), scab (*Elsinoe fawcetti*), and fruit rot (*Penicillium digitatum, P. italicum*);

Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), *fusarium* wilt (*Fusarium oxysporum*), downy mildew (*Pseudoperonospora cubensis*), *phytophthora* rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora parasitica*), and downy mildew (*Peronospora parasitica*); Welsh onion diseases: rust (*Puccinia allii*); Soybean diseases: purple stain (*Cercospora kikuchii*), *sphaceloma* scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), *Rhizoctonia* aerial blight (*Rhizoctonia solani*), septoria brown spot (*Septoria glycines*), and frog eye leaf spot (*Cercospora sojina*); Kidney bean diseases: anthracnose (*Colletotrichum lindemthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and verticillium wilt (*verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces sochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: botrytis leaf blight (*Botrytis cinerea, B. byssoidea, B. squamosa*), gray-mold neck rot (*Botrytis slli*), and small sclerotial rot (*Botrytis squamosa*); various crops diseases: gray mold (*Botrytis cinerea*) and sclerotinia rot (*Sclerotinia sclerotiorum*); Japanese radish diseases: alternaria leaf spot (*Alternaria brassicicola*); Turfgrass diseases: dollar spot (*Sclerotinia homeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), and cottonycushion scale (*Icerya purchasi*); lace bugs (Tingidae); and jumping plant lices (Homoptera, Psylloidea).

Lepidoptera: pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes* orana *fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); leaf miners (Gracillariidae) such as tea leafroller (*Caloptilia theivora*) and apple leafminer (*Phyllonorycter ringoneella*); codling moths (Carposimidae) such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (*Plutella xylostella*); gelechild moths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

Thysanoptera: thrips such as yellow citrus thrip (*Frankliniella occidentalis*), melon thrip (*Thrips palmi*), yellow tea thrip (*Scirtothrips dorsalis*), onion thrips (*Thrips tabaci*), flower thrip (*Frankliniella intonsa*), and tobacco thrip (*Frankliniella fusca*).

Diptera: houseflies (*Musca domestica*), common mosquito (*Culex pipiens pallens*), horsefly (*Tabanus trigonus*), onion maggot (*Hylemya antigua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Meditterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leafcutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta America*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (*Aculops pelekassi*)); Tarsonemidae (for example, broad mite (*Polyphagotarsonemus latus*)); Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides ptrenyssnus*)); Cheyletidae (for example, cheyletid mite (*Cheyletus eruditus*), *Cheyletus malaccensis*, and *Cheyletus moorei*; and Dermanyssidae.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), dermacentor spp., *Ornithodoros* spp. (for example, *Ornithodoros moubata*), red mite (*Dermahyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Ades* spp. (for example, Asian tiger mosquito (*Aedes albopictus*)), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp.), *Linognathus* spp., *Haematopinus* spp., *Ctenocephalides* spp. (for example, cat flea (*Ctenocephalides felis*)) *Xenosylla* spp., Pharaoh's ant (*monomorium pharaonic*) and nematodes [for example, hairworm (for example, *Nippostrongylus brasiliensis, Trichostrongylus axei, Trichostrongylus colubriformis*), *Trichinella* spp. (for example, *Trichinella spiriralis*), barber pole worm (*Haemonchus contortus*), *Nematodirus* spp. (for example, *Nematodirus battus*), *Ostertagia circumcincta, Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be shown.

Production Example 1

A mixture of 0.30 g of 1-(2-bromomethylphenyl)-4-methyl-1,4-dihydrotetrazol-5-one mentioned in Reference Production Example 1, 0.3 g of 2-chloro-4-(5-methoxy-1,4-dimethyl-1H-pyrazol-3-yl)phenol mentioned in Reference Production Example 18, 0.2 g of potassium carbonate, and 10 mL of acetonitrile was stirred with heating under reflux for 4 hours. After cooling to room temperature, the reaction mixture was filtered and the filtrate was concentrated. The residue thus obtained was subjected to silica gel column chromatography to obtain 0.31 g of 1-{2-[2-chloro-4-(5-methoxy-1,4-dimethyl-1H-pyrazol-3-yl)phenoxymethyl]phenyl}-4-methyl-1,4-dihydrotetrazol-5-one (hereinafter referred to as the present compound 1).

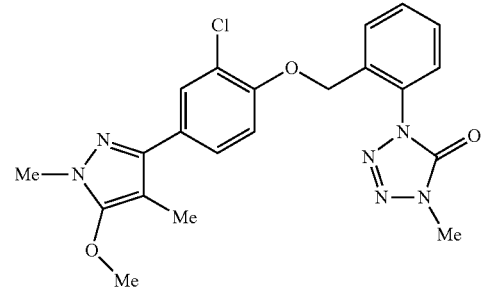 [SMILES: COc1c(C)c(-c2ccc(OCc3ccccc3-n3nnn(C)c3=O)c(Cl)c2)nn1C]

$^1$H-NMR (CDCl$_3$) δ: 7.75 (1H, d, J=7.0 Hz), 7.66 (1H, d, J=2.2 Hz), 7.56-7.49 (3H, m), 7.41 (1H, dd, J=8.8, 1.8 Hz), 6.92 (1H, d, J=8.7 Hz), 5.29 (2H, s), 3.93 (3H, s), 3.70 (3H, s), 3.70 (3H, s), 2.12 (3H, s).

Production Example 2

A mixture of 0.6 g of 1-(2-bromomethylphenyl)-4-methyl-1,4-dihydrotetrazol-5-one mentioned in Reference Production Example 1, 0.5 g of 2-methyl-4-(5-methoxy-1,4-dimethyl-1H-pyrazol-3-yl)phenol mentioned in Reference Production Example 11, 0.39 g of potassium carbonate, and 20 mL of acetonitrile was stirred with heating under reflux for 4 hours. After cooling to room temperature, the reaction mixture was filtered and the filtrate was concentrated. The residue thus obtained was subjected to silica gel column chromatography to obtain 0.4 g of 1-{2-[2-methyl-4-(5-methoxy-1,4-dimethyl-1H-pyrazol-3-yl)phenoxymethyl]phenyl}-4-methyl-1,4-dihydrotetrazol-5-one (hereinafter referred to as the present compound 2).

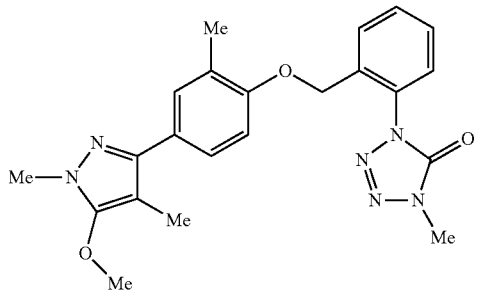 [SMILES: COc1c(C)c(-c2ccc(OCc3ccccc3-n3nnn(C)c3=O)c(C)c2)nn1C]

$^1$H-NMR (CDCl$_3$) δ: 7.72 (1H, d, J=7.2 Hz), 7.55-7.48 (3H, m), 7.44-7.43 (1H, m), 7.33 (1H, dd, J=8.5, 1.9 Hz), 6.82 (1H, d, J=8.5 Hz), 5.18 (2H, s), 3.93 (3H, s), 3.70 (3H, s), 3.67 (3H, s), 2.22 (3H, s), 2.12 (3H, s).

Production Example 3

At 0° C., 0.41 g of triethylsilane was added to a mixture of 0.64 g of 1-{2-[2-methyl-4-(5-ethoxy-4-formyl-1-methyl-1H-pyrazol-3-yl)phenoxymethyl]phenyl}-4-methyl-1,4-dihydrotetrazol-5-one mentioned in Reference Production Example 3 and 10 mL of trifluoroacetic acid. After stirring at room temperature for 10 hours, the solvent was distilled off and 10 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 0.6 g of 1-{2-[2-methyl-4-(5-ethoxy-1,4-dimethyl-1H-pyrazol-3-yl)phenoxymethyl]phenyl}-4-methyl-1,4-dihydrotetrazol-5-one (hereinafter referred to as the present compound 3).

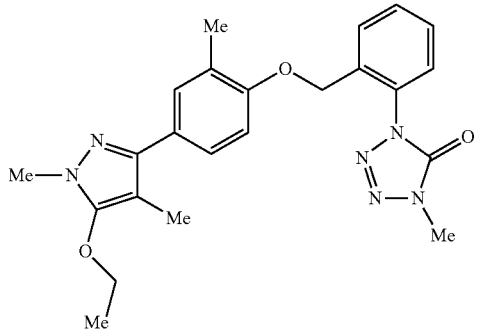 [SMILES: CCOc1c(C)c(-c2ccc(OCc3ccccc3-n3nnn(C)c3=O)c(C)c2)nn1C]

$^1$H-NMR (CDCl$_3$) δ: 7.72 (1H, d, J=7.3 Hz), 7.55-7.51 (1H, m), 7.50-7.48 (2H, m), 7.45 (1H, dd, J=2.1, 0.7 Hz), 7.34 (1H, dd, J=8.4, 1.9 Hz), 6.83 (1H, d, J=8.5 Hz), 5.18 (2H, s), 4.14 (2H, q, J=7.1 Hz), 3.71 (3H, s), 3.67 (3H, s), 2.23 (3H, s), 2.10 (3H, s), 1.41 (3H, t, J=7.1 Hz).

Production Example 4

At 0° C., 0.31 g of triethylsilane was added to a mixture of 0.5 g of 1-{2-[2-methyl-4-(4-formyl-1-methyl-5-propoxy-1H-pyrazol-3-yl)phenoxymethyl]phenyl}-4-methyl-1,4-dihydrotetrazol-5-one mentioned in Reference Production Example 4 and 10 mL of trifluoroacetic acid. After stirring at room temperature for 10 hours, the solvent was distilled off and 10 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 0.48 g of 1-{2-[2-methyl-4-(1,4-dimethyl-5-propoxy-1H-pyrazol-3-yl)phenoxymethyl]phenyl}-4-methyl-1,4-dihydrotetrazol-5-one (hereinafter referred to as the present compound 4).

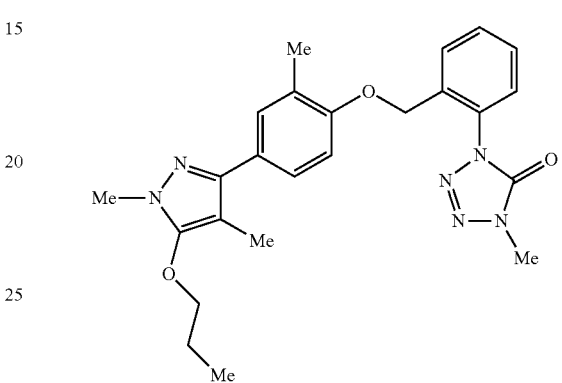

$^1$H-NMR (CDCl$_3$) δ: 7.72 (1H, d, J=7.3 Hz), 7.55-7.50 (1H, m), 7.49-7.45 (3H, m), 7.34 (1H, dd, J=8.2, 2.1 Hz), 6.83 (1H, d, J=8.5 Hz), 5.18 (2H, s), 4.02 (2H, t, J=6.6 Hz), 3.70 (3H, s), 3.67 (3H, s), 2.22 (3H, s), 2.10 (3H, s), 1.85-1.76 (2H, m), 1.06 (3H, t, J=7.4 Hz).

Production Example 5

A similar reaction was performed as in Production Example 1 using 4-(1,4-dimethyl-5-methylthio-1H-pyrazol-3-yl)-2-methyl-phenol mentioned in Reference Production Example 21 in place of 2-chloro-4-(5-methoxy-1,4-dimethyl-1H-pyrazol-3-yl)phenol to obtain 1-{2-[2-methyl-4-(1,4-dimethyl-5-methylthio-1H-pyrazol-3-yl)phenoxymethyl]phenyl}-4-methyl-1,4-dihydrotetrazol-5-one (hereinafter referred to as the present compound 5).

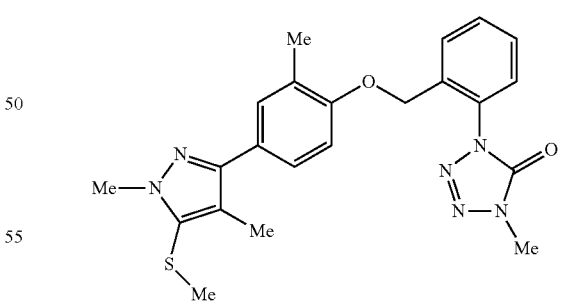

$^1$H-NMR (CDCl$_3$) δ: 7.74-7.72 (1H, m), 7.56-7.52 (1H, m), 7.50-7.46 (3H, m), 7.39-7.36 (1H, m), 6.84 (1H, d, J=8.5 Hz), 5.19 (2H, s), 3.99 (3H, s), 3.68 (3H, s), 2.26 (3H, s), 2.26 (3H, s), 2.23 (3H, s).

Production Example 6

At 0° C., 0.68 g of phosphorus oxychloride was added to a mixture of 1.0 g of 1-{2-[2-methyl-4-(5-aminocarbonyl- 1,4-dimethyl-1H-pyrazol-3-yl)phenoxymethyl]phenyl}-4-methyl-1,4-dihydrotetrazol-5-one mentioned in Reference Production Example 30 and 20 mL of pyridine. After stirring at room temperature for 2 hours, 30 mL of water was added. The precipitate was collected by filtration, washed with 10 mL of water and 10 mL of hexane, and then dried under reduced pressure to obtain 0.91 g of 1-{2-[2-methyl-4-(5-cyano-1,4-dimethyl-1H-pyrazol-3-yl)phenoxymethyl]phenyl}-4-methyl-1,4-dihydrotetrazol-5-one (hereinafter referred to as the present compound 6).

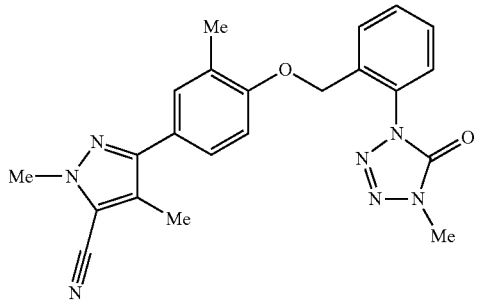 [SMILES: Cc1cc(-c2nn(C)c(C#N)c2C)ccc1OCc1ccccc1-n1nnn(C)c1=O]

$^1$H-NMR (CDCl$_3$) δ: 7.71 (1H, d, J=7.1 Hz), 7.56-7.52 (1H, m), 7.51-7.48 (2H, m), 7.43-7.43 (1H, m), 7.34 (1H, dd, J=8.4, 1.9 Hz), 6.85 (1H, d, J=8.5 Hz), 5.20 (2H, s), 4.02 (3H, s), 3.68 (3H, s), 2.32 (3H, s), 2.24 (3H, s).

Production Example 7

A similar reaction was performed as in Production Example 6 using 1-{2-[2-methyl-4-(5-aminocarbonyl-1-ethyl-4-methyl-1H-pyrazol-3-yl)phenoxymethyl]phenyl}-4-methyl-1,4-dihydrotetrazol-5-one mentioned in Reference Production Example 34 in place of 1-{2-[2-methyl-4-(5-aminocarbonyl-1,4-dimethyl-1H-pyrazol-3-yl)phenoxymethyl]phenyl}-4-methyl-1,4-dihydrotetrazol-5-one to obtain 1-{2-[2-methyl-4-(5-cyano-1-ethyl-4-methyl-1H-pyrazol-3-yl)phenoxymethyl]phenyl}-4-methyl-1,4-dihydrotetrazol-5-one (hereinafter referred to as the present compound 7).

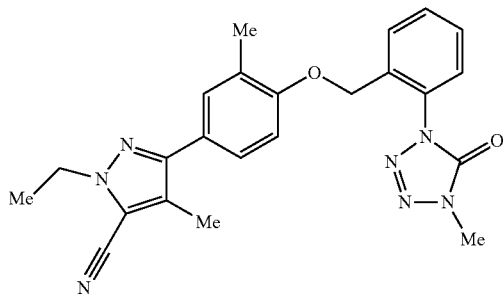 [SMILES: CCn1nc(-c2ccc(OCc3ccccc3-n3nnn(C)c3=O)c(C)c2)c(C)c1C#N]

$^1$H-NMR (CDCl$_3$) δ: 7.72-7.70 (1H, m), 7.56-7.52 (1H, m), 7.51-7.48 (2H, m), 7.44 (1H, dd, J=2.2, 0.8 Hz), 7.35 (1H, dd, J=8.3, 2.2 Hz), 6.85 (1H, d, J=8.4 Hz), 5.20 (2H, s), 4.33 (2H, q, J=7.2 Hz), 3.69 (3H, s), 2.32 (3H, s), 2.24 (3H, s), 1.54 (3H, t, J=7.2 Hz).

Production Example 8

A similar reaction was performed as in Production Example 1 using 2-methyl-4-(4-chloro-5-methoxy-1-methyl-1H-pyrazol-3-yl)phenol mentioned in Reference Production Example 37 in place of 2-chloro-4-(5-methoxy-1,4-dimethyl-1H-pyrazol-3-yl)phenol to obtain 1-{2-[2-methyl-4-(4-chloro-5-methoxy-1-methyl-1H-pyrazol-3-yl)phenoxymethyl]phenyl}-4-methyl-1,4-dihydrotetrazol-5-one (hereinafter referred to as the present compound 8).

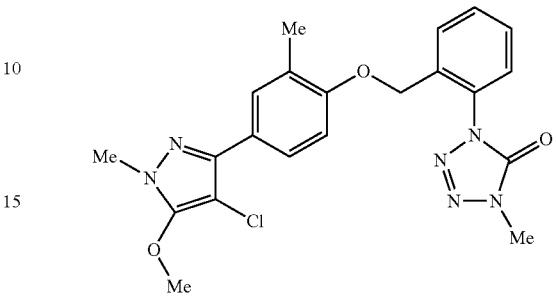

$^1$H-NMR (CDCl$_3$) δ: 7.72 (1H, d, J=7.2 Hz), 7.61-7.58 (2H, m), 7.56-7.52 (1H, m), 7.51-7.47 (2H, m), 6.84 (1H, d, J=9.1 Hz), 5.19 (2H, s), 4.11 (3H, s), 3.70 (3H, s), 3.67 (3H, s), 2.23 (3H, s).

Production Example 9

At room temperature, 0.7 mL of N,N-diethylaminosulfur trifluoride was added to a mixture of 0.86 g of 1-{2-[2-methyl-4-(4-formyl-5-methoxy-1-methyl-1H-pyrazol-3-yl)phenoxymethyl]phenyl}-4-methyl-1,4-dihydrotetrazol-5-one mentioned in Reference Production Example 38 and 10 mL of chloroform, followed by stirring at 40° C. for 3 hours. At room temperature, water was poured into the reaction mixture and the mixture was extracted with chloroform. The organic layer was washed with water, dried over anhydrous magnesium sulfate, and then concentrated under reduced pressure. The residue thus obtained was subjected to silica gel column chromatography to obtain 0.15 g of 1-{2-[2-methyl-4-(4-difluoromethyl-5-methoxy-1-methyl-1H-pyrazol-3-yl)phenoxymethyl]phenyl}-4-methyl-1,4-dihydrotetrazol-5-one (hereinafter referred to as the present compound 9).

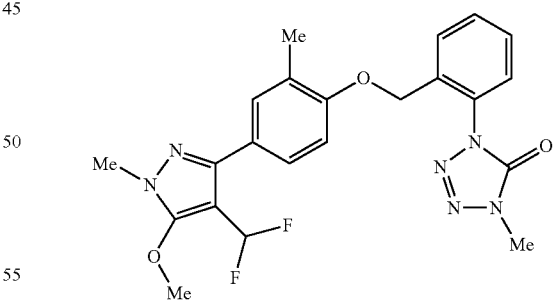

$^1$H-NMR (CDCl$_3$) δ: 7.71 (1H, d, J=7.2 Hz), 7.56-7.49 (3H, m), 7.35 (1H, dd, J=2.0, 0.7 Hz), 7.25 (1H, dd, J=8.3, 2.2 Hz), 6.85 (1H, d, J=8.6 Hz), 6.58 (1H, t, J=54.6 Hz), 5.20 (2H, s), 4.12 (3H, s), 3.71 (3H, s), 3.68 (3H, s), 2.23 (3H, s).

Production Example 10

At room temperature, 0.2 g of 2,4,6-trichloro-1,3,5-triazine was added and to a mixture of 0.96 g of 1-{2-[2-methyl-4-(4-carboaldehyde oxime-5-methoxy-1-methyl-1H-pyrazol-3-yl)phenoxymethyl]phenyl}-4-methyl-1,4-dihydrotetrazol-5-one mentioned in Reference Production Example 39 and 10 mL of N,N-dimethylformamide, followed by stirring for 7 hours. After adding 30 mL of water, the precipitate was collected by filtration and dried under reduced pressure. The residue thus obtained was subjected to silica gel column chromatography to obtain 0.35 g of 1-{2-[2-methyl-4-(4-cyano-5-methoxy-1-methyl-1H-pyrazol-3-yl)phenoxymethyl]phenyl}-4-methyl-1,4-dihydrotetrazol-5-one (hereinafter referred to as the present compound 10).

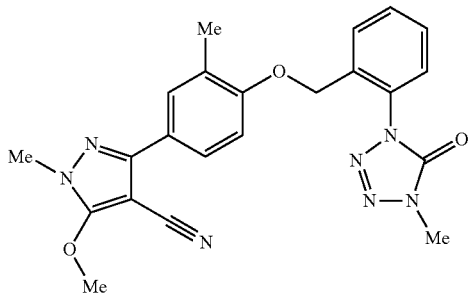 [SMILES: COc1c(C#N)c(-c2ccc(OCc3ccccc3-n3nnn(C)c3=O)c(C)c2)nn1C]

$^1$H-NMR (CDCl$_3$) δ: 7.71 (1H, d, J=7.3 Hz), 7.67-7.65 (2H, m), 7.56-7.49 (3H, m), 6.86 (1H, d, J=8.9 Hz), 5.21 (2H, d, J=4.8 Hz), 4.33 (3H, s), 3.68 (3H, s), 3.65 (3H, s), 2.23 (3H, s).

Production Example 11

A similar reaction was performed as in Reference Production Example 35 using 1-{2-[4-(5-hydroxy-1-methyl-1H-pyrazol-3-yl)-2-methylphenoxymethyl]phenyl}-4-methyl-1,4-dihydrotetrazol-5-one mentioned in Reference Production Example 40 in place of 5-hydroxy-3-(4-isopropoxy-3-methylphenyl)-1-methyl-1H-pyrazole to obtain 0.31 g of 1-{2-[4-(5-methoxy-1-methyl-1H-pyrazol-3-yl)-2-methylphenoxymethyl]phenyl}-4-methyl-1,4-dihydrotetrazol-5-one (hereinafter referred to as the present compound 11).

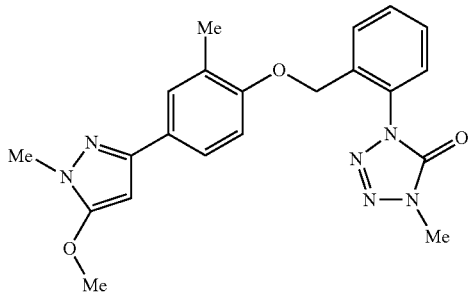 [SMILES: COc1cc(-c2ccc(OCc3ccccc3-n3nnn(C)c3=O)c(C)c2)nn1C]

$^1$H-NMR (CDCl$_3$) δ: 7.72 (1H, d, J=7.7 Hz), 7.57-7.44 (5H, m), 6.80 (1H, d, J=8.4 Hz), 5.75 (1H, s), 5.18 (2H, s), 3.92 (3H, s), 3.67 (3H, s), 3.67 (3H, s), 2.21 (3H, s).

Production Example 12

At room temperature, N-bromosuccinimide was added to a mixture of the present compound 11 and chloroform, followed by stirring for 5 hours. The residue thus obtained was subjected to silica gel column chromatography to obtain 0.27 g of 1-{2-[4-(4-bromo-5-methoxy-1-methyl-1H-pyrazol-3-yl)-2-methylphenoxymethyl]phenyl}-4-methyl-1,4-dihydrotetrazol-5-one (hereinafter referred to as the present compound 12).

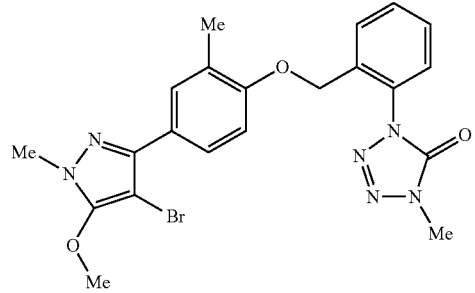 [SMILES: COc1c(Br)c(-c2ccc(OCc3ccccc3-n3nnn(C)c3=O)c(C)c2)nn1C]

$^1$H-NMR (CDCl$_3$) δ: 7.72 (1H, d, J=7.1 Hz), 7.59 (2H, m), 7.52 (3H, m), 6.84 (1H, d, J=9.2 Hz), 5.19 (2H, s), 4.08 (3H, s), 3.73 (3H, s), 3.67 (3H, s), 2.23 (3H, s).

Production Example 13

A similar reaction was performed as in Reference Production Example 12 using 1-chloromethyl-4-fluoro-1,4-diazoniabicyclo[2,2,2]octanebis(tetrafluoroborate) in place of N-bromosuccinimide to obtain 1-{2-[4-(4-fluoro-5-methoxy-1-methyl-1H-pyrazol-3-yl)-2-methylphenoxymethyl]phenyl}-4-methyl-1,4-dihydrotetrazol-5-one (hereinafter referred to as the present compound 13).

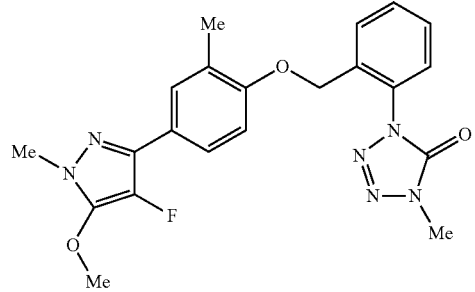 [SMILES: COc1c(F)c(-c2ccc(OCc3ccccc3-n3nnn(C)c3=O)c(C)c2)nn1C]

$^1$H-NMR (CDCl$_3$) δ: 7.72 (1H, d, J=7.6 Hz), 7.59-7.48 (5H, m), 6.83 (1H, d, J=8.5 Hz), 5.19 (2H, s), 4.10 (3H, d, J=2.3 Hz), 3.67 (3H, s), 3.63 (3H, s), 2.22 (3H, s).

Production Example 14

A similar reaction was performed as in Production Example 1 using 4-(5-methoxy-1-methyl-1H-pyrazol-3-yl)-2,5-dimethylphenol mentioned in Reference Production Example 43 in place of 2-chloro-4-(5-methoxy-1,4-dimethyl-1H-pyrazol-3-yl)phenol to obtain 0.55 g of 1-{2-[4-(5-methoxy-1-methyl-1H-pyrazol-3-yl)-2,5-dimethylphenoxymethyl]phenyl}-4-methyl-1,4-dihydrotetrazol-5-one (hereinafter referred to as the present compound 14).

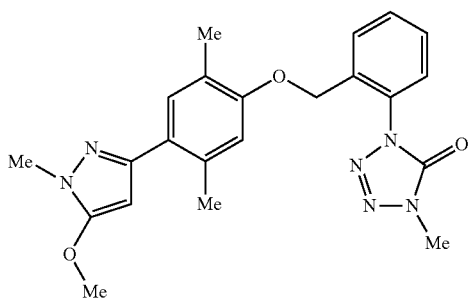 [SMILES: COc1cc(-c2cc(C)c(OCc3ccccc3-n3nnn(C)c3=O)cc2C)nn1C]

¹H-NMR (CDCl₃) δ: 7.74 (1H, d, J=7.2 Hz), 7.58-7.49 (3H, m), 6.96 (1H, s), 6.70 (1H, s), 5.56 (1H, s), 5.18 (2H, s), 3.91 (3H, s), 3.70 (3H, s), 3.48 (3H, s), 2.16 (3H, s), 2.13 (3H, s).

Regarding the production of intermediates for producing the above-mentioned present compounds, Reference Production Examples will be shown below.

Reference Production Example 1

In accordance with the following steps (1) to (3), 1-(2-bromomethylphenyl)-4-methyl-1,4-dihydrotetrazol-5-one was produced.

<Step (1)>

Anhydrous aluminum chloride (55.1 g) was added to 500 mL of N,N-dimethylformamide under ice cooling, followed by stirring for 15 minutes. To this was added 26.9 g of sodium azide and the mixture was stirred for 15 minutes, followed by the addition of 50.6 g of 1-isocyanato-2-methylbenzene and further heating at 70° C. for 4 hours. After cooling, the reaction solution was added in a mixture of 51.8 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 69.8 g of 1-(2-methylphenyl)-1,4-dihydrotetrazol-5-one.

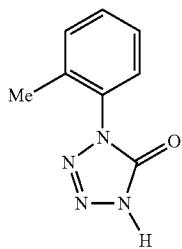

¹H-NMR (CDCl₃) δ: 2.32 (3H, s), 7.37-7.47 (4H, m), 13.55 (1H, s).

<Step (2)>

To a mixture of 69.8 g of the above-mentioned 1-(2-methylphenyl)-1,4-dihydrotetrazol-5-one 69.8 g and 380 mL of N,N-dimethylformamide, 18.2 g of 55% sodium hydride was added under ice cooling. After stirring for 20 minutes, 59.4 g of methyl iodide was added. The temperature of the mixture was raised to room temperature, followed by stirring for 2.5 hours. Water was poured into the reaction mixture and the mixture was extracted with methyl tert-butyl ether. The organic layer were washed with 10% hydrochloric acid, water, and a saturated saline solution, dried over anhydrous magnesium sulfate, and then concentrated under reduced pressure. The residue thus obtained was subjected to silica gel column chromatography to obtain 52.5 g of 1-(2-methylphenyl)-4-methyl-1,4-dihydrotetrazol-5-one.

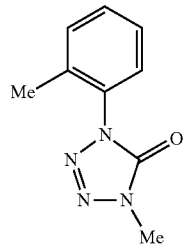

¹H-NMR (CDCl₃) δ: 2.29 (3H, s), 3.72 (3H, s), 7.32-7.44 (4H, m).

<Step (3)>

A mixture of 1.5 g of the above-mentioned 1-(2-methylphenyl)-4-methyl-1,4-dihydrotetrazol-5-one, 1.5 g of N-bromosuccinimide, 20 mL of carbon tetrachloride, and 0.01 g of azoisobutyronitrile was stirred with heating under reflux for 8 hours. After cooling to room temperature, the mixture was filtered and the filtrate was concentrated under reduced pressure. The residue thus obtained was subjected to silica gel chromatography to obtain 2.1 g of 1-(2-bromomethylphenyl)-4-methyl-1,4-dihydrotetrazol-5-one.

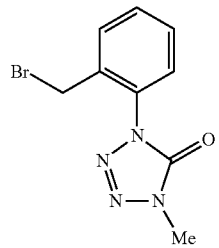

¹H-NMR (CDCl₃) δ: 3.75 (3H, s), 4.59 (2H, s), 7.43-7.51 (3H, m), 7.53-7.56 (1H, m).

Reference Production Example 2

A mixture of 2.2 g of 1-(2-bromomethylphenyl)-4-methyl-1,4-dihydrotetrazol-5-one mentioned in Reference Production Example 1, 2.1 g of 2-methyl-4-(5-chloro-4-formyl-1-methyl-1H-pyrazol-3-yl)phenol mentioned in Reference Production Example 8, 1.5 g of potassium carbonate, and 100 mL of acetonitrile was stirred with heating under reflux followed by stirring for 4 hours. After cooling to room temperature, the reaction mixture was filtered and the filtrate was concentrated. The residue thus obtained was subjected to silica gel column chromatography to obtain 2.8 g of 1-{2-[2-methyl-4-(5-chloro-4-formyl-1-methyl-1H-pyrazol-3-yl)phenoxymethyl]phenyl}-4-methyl-1,4-dihydrotetrazol-5-one.

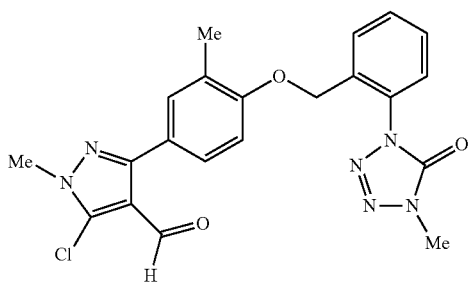 [SMILES: Cc1cc(-c2nn(C)c(Cl)c2C=O)ccc1OCc1ccccc1-n1nnn(C)c1=O]

¹H-NMR (CDCl₃) δ: 9.91 (1H, s), 7.73-7.70 (1H, m), 7.57-7.48 (5H, m), 6.89-6.86 (1H, m), 5.21 (2H, s), 3.92 (3H, s), 3.69 (3H, s), 2.24 (3H, s).

Reference Production Example 3

At room temperature, 0.93 g of a 20%-sodium ethoxide-ethanol solution was added to a mixture of 0.8 g of 1-{2-[2-methyl-4-(5-chloro-4-formyl-1-methyl-1H-pyrazol-3-yl)phenoxymethyl]phenyl}-4-methyl-1,4-dihydrotetrazol-5-one mentioned in Reference Production Example 2, and 10 mL of tetrahydrofuran. After stirring at room temperature for 2.5 hours, 5 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 0.71 g of 1-{2-[2-methyl-4-(5-ethoxy-4-formyl-1-methyl-1H-pyrazol-3-yl)phenoxymethyl]phenyl}-4-methyl-1,4-dihydrotetrazol-5-one.

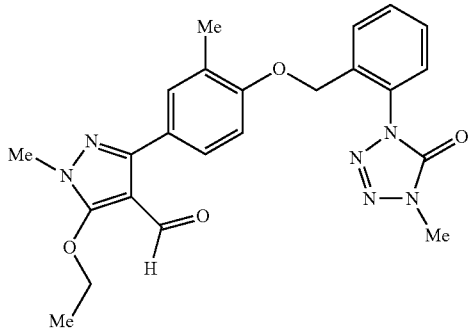 [SMILES: CCOc1c(C=O)c(-c2ccc(OCc3ccccc3-n3nnn(C)c3=O)c(C)c2)nn1C]

¹H-NMR (CDCl₃) δ: 9.71 (1H, s), 7.72 (1H, d, J=6.9 Hz), 7.57-7.48 (3H, m), 7.40 (1H, d, J=1.6 Hz), 7.34 (1H, dd, J=8.4, 2.2 Hz), 6.87 (1H, d, J=8.5 Hz), 5.21 (2H, s), 4.63 (2H, q, J=7.0 Hz), 3.72 (3H, s), 3.69 (3H, s), 2.23 (3H, s), 1.44 (3H, t, J=7.1 Hz).

Reference Production Example 4

At room temperature, 0.12 g of propanol and 0.89 g of 55%-sodium hydride were added to a mixture of 0.6 g of 1-{2-[2-methyl-4-(5-chloro-4-formyl-1-methyl-1H-pyrazol-3-yl)phenoxymethyl]phenyl}-4-methyl-1,4-dihydrotetrazol-5-one mentioned in Reference Production Example 2 and 10 mL of tetrahydrofuran. After stirring at room temperature for 5 hours, 5 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 0.71 g of 1-{2-[2-methyl-4-(4-formyl-1-methyl-5-propoxy-1H-pyrazol-3-yl)phenoxymethyl]phenyl}-4-methyl-1,4-dihydrotetrazol-5-one.

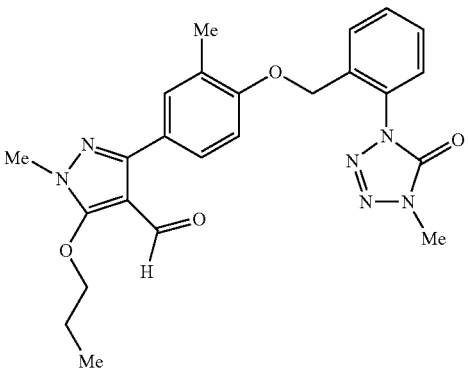 [SMILES: CCCOc1c(C=O)c(-c2ccc(OCc3ccccc3-n3nnn(C)c3=O)c(C)c2)nn1C]

¹H-NMR (CDCl₃) δ: 9.71 (1H, s), 7.71 (1H, d, J=6.9 Hz), 7.57-7.51 (1H, m), 7.51-7.48 (2H, m), 7.40-7.40 (1H, m), 7.34 (1H, dd, J=8.2, 2.3 Hz), 6.86 (1H, d, J=8.5 Hz), 5.21 (2H, s), 4.52 (2H, t, J=6.6 Hz), 3.72 (3H, s), 3.69 (3H, s), 2.23 (3H, s), 1.83 (2H, td, J=14.0, 7.4 Hz), 1.06 (3H, t, J=7.3 Hz).

Reference Production Example 5

A mixture of 10 g of 1-(4-hydroxy-3-methylphenyl)ethanone, 13.6 g of isopropyl iodide, 18.4 g of potassium carbonate, and 250 mL of acetone was stirred with heating under reflux for 12 hours. The reaction mixture was filtered and then the filtrate was concentrated under reduced pressure. The residue thus obtained was subjected to silica gel column chromatography to obtain 9.5 g of 1-(4-isopropoxy-3-methylphenyl)ethanone.

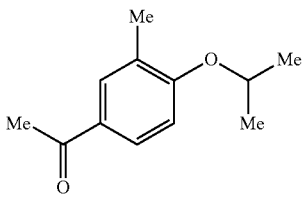 [SMILES: CC(=O)c1ccc(OC(C)C)c(C)c1]

¹H-NMR (CDCl₃) δ: 7.80-7.78 (2H, m), 6.84 (1H, d, J=8.2 Hz), 4.69-4.60 (1H, m), 2.54 (3H, s), 2.23 (3H, s), 1.37 (6H, d, J=6.0 Hz).

Reference Production Example 6

At room temperature, 11.6 g of diethyl carbonate, 4.5 g of 55% sodium hydride, 0.04 g of dibenzo-18-crown-6, and 3 mL of ethanol were added to a mixture of 9.4 g of 1-(4-isopropoxy-3-methylphenyl)ethanone mentioned in Reference Production Example 5 and 150 mL of tetrahydrofuran, followed by stirring with heating under reflux for 9 hours. After water was poured into the reaction mixture, the mixture was acidified by adding 10% hydrochloric acid and then extracted with ethyl acetate. The organic layer was washed with water, dried over anhydrous magnesium sulfate, and then concentrated under reduced pressure. The residue thus obtained was subjected to silica gel column chromatography to obtain 12.1 g of 3-(4-isopropoxy-3-methylphenyl)-3-oxo-propionic acid ethyl ester.

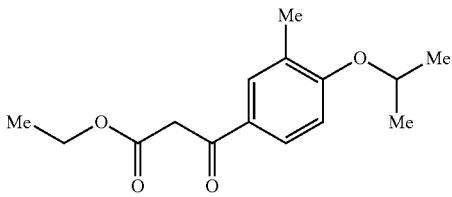 [SMILES: CCOC(=O)CC(=O)c1ccc(OC(C)C)c(C)c1]

$^1$H-NMR (CDCl$_3$) δ: 7.79-7.76 (2H, m), 6.85-6.83 (1H, m), 4.68-4.62 (1H, m), 4.21 (2H, q, J=7.2 Hz), 3.93 (2H, s), 2.22 (3H, s), 1.37 (6H, d, J=6.0 Hz), 1.26 (3H, t, J=7.1 Hz).

Reference Production Example 7

At room temperature, 21 g of N-methylhydrazine was added to a mixture of 12.1 g of 3-(4-isopropoxy-3-methylphenyl)-3-oxopropionic acid ethyl ester mentioned in Reference Production Example 6 and 100 mL of toluene, followed by stirring for 12 hours. Toluene was distilled off under reduced pressure and 100 mL of water was poured into the reaction mixture at room temperature. The mixture was acidified by adding 10% hydrochloric acid, followed by stirring for 3 hours. The precipitate was filtered, washed with 400 mL of water and 500 mL of ethyl acetate, and then dried under reduced pressure to obtain 9.5 g of 5-hydroxy-3-(4-isopropoxy-3-methylphenyl)-1-methyl-1H-pyrazole.

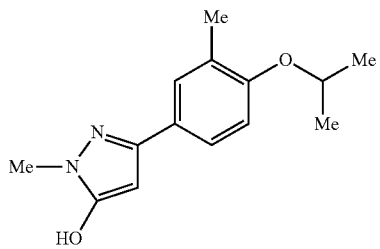 [SMILES: Cc1cc(-c2cc(O)n(C)n2)ccc1OC(C)C]

$^1$H-NMR (DMSO-D$_6$) δ: 7.58-7.54 (2H, m), 7.01-6.98 (1H, m), 5.95 (1H, s), 4.66-4.60 (1H, m), 3.62 (3H, s), 2.16 (3H, s), 1.28 (6H, d, J=5.1 Hz).

Reference Production Example 8

At 0° C., 10.9 g of N,N-dimethylformamide was added to 150 g of phosphorus oxychloride. After stirring for 0.5 hour, 28 g of 5-hydroxy-3-(4-isopropoxy-3-methylphenyl)-1-methyl-1H-pyrazole mentioned in Reference Production Example 7 was added. After stirring at 100° C. for 10 hours, the reaction solvent was distilled off. To the reaction mixture, 100 mL of ice water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 21 g of 5-chloro-4-formyl-3-(4-isopropoxy-3-methylphenyl)-1-methyl-1H-pyrazole, 1 g of 2-methyl-4-(5-chloro-4-formyl-1-methyl-1H-pyrazol-3-yl)phenol, and 1 g of 4-formyl-5-hydroxy-3-(4-isopropoxy-3-methylphenyl)-1-methyl-1H-pyrazole.

5-Chloro-4-formyl-3-(4-isopropoxy-3-methylphenyl)-1-methyl-1H-pyrazole

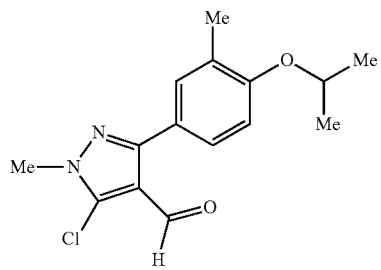 [SMILES: Cc1cc(-c2nn(C)c(Cl)c2C=O)ccc1OC(C)C]

$^1$H-NMR (CDCl$_3$) δ: 9.93 (1H, s), 7.52-7.50 (2H, m), 6.91-6.89 (1H, m), 4.63-4.54 (1H, m), 3.92 (3H, s), 2.25 (3H, s), 1.36 (6H, d, J=6.0 Hz).

2-Methyl-4-(5-chloro-4-formyl-1-methyl-1H-pyrazol-3-yl)phenol

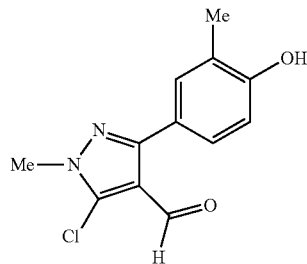 [SMILES: Cc1cc(-c2nn(C)c(Cl)c2C=O)ccc1O]

$^1$H-NMR (CDCl$_3$) δ: 9.92 (1H, s), 7.52-7.51 (1H, m), 7.47 (1H, dd, J=8.2, 2.3 Hz), 6.85 (1H, d, J=8.2 Hz), 4.95 (1H, s), 3.93 (3H, s), 2.30 (3H, s).

4-Formyl-5-hydroxy-3-(4-isopropoxy-3-methylphenyl)-1-methyl-1H-pyrazole

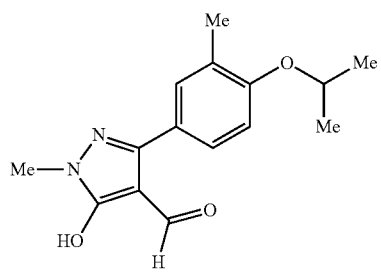 [SMILES: Cc1cc(-c2nn(C)c(O)c2C=O)ccc1OC(C)C]

$^1$H-NMR (DMSO-D$_6$) δ: 10.79 (1H, s), 9.45 (1H, s), 7.31-7.29 (2H, m), 7.08 (1H, d, J=8.8 Hz), 4.74-4.65 (1H, m), 3.55 (3H, s), 2.18 (3H, s), 1.32 (6H, d, J=5.9 Hz)

Reference Production Example 9

At room temperature, 0.6 g of methanol and 0.8 g of 55% sodium hydride were added to a mixture of 4.8 g of 5-chloro-4-formyl-3-(4-isopropoxy-3-methylphenyl)-1-methyl-1H-pyrazole mentioned in Reference Production Example 8 and 100 mL of tetrahydrofuran, followed by stirring for 3 hours. To the reaction mixture, 50 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 4.5 g of 4-formyl-3-(4-isopropoxy-3-methylphenyl)-5-methoxy-1-methyl-1H-pyrazole.

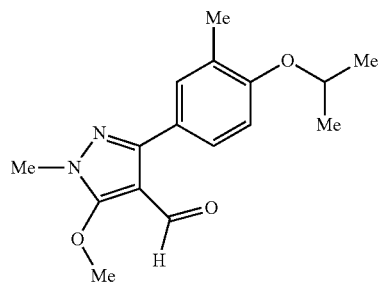 [SMILES: COc1c(C=O)c(-c2ccc(OC(C)C)c(C)c2)nn1C]

$^1$H-NMR (CDCl$_3$) δ: 9.75 (1H, s), 7.39 (1H, d, J=1.9 Hz), 7.35 (1H, dd, J=8.3, 2.3 Hz), 6.90 (1H, d, J=8.5 Hz), 4.63-4.54 (1H, m), 4.30 (3H, s), 3.71 (3H, s), 2.24 (3H, s), 1.36 (6H, d, J=6.0 Hz).

Reference Production Example 10

At 0° C., 4.2 g of triethylsilane was added to a mixture of 4.2 g of 4-formyl-3-(4-isopropoxy-3-methylphenyl)-5-methoxy-1-methyl-1H-pyrazole mentioned in Reference Production Example 9 and 20 mL of trifluoroacetic acid. After stirring at room temperature for 6 hours, the solvent was distilled off and 10 mL of water was added, and then the mixture was extracted with ethyl acetate. The organic layer was washed with water, dried over anhydrous magnesium sulfate, and then concentrated under reduced pressure. The residue thus obtained was subjected to silica gel column chromatography to obtain 3.8 g of 1,4-dimethyl-3-(4-isopropoxy-3-methylphenyl)-5-methoxy-1H-pyrazole.

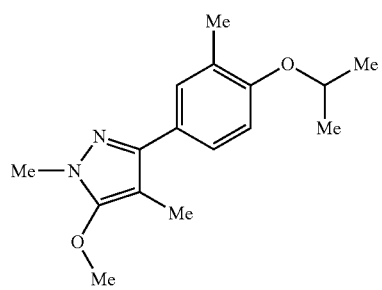

$^1$H-NMR (CDCl$_3$) δ: 7.43 (1H, dd, J=2.1, 0.7 Hz), 7.37-7.34 (1H, m), 6.86 (1H, d, J=8.5 Hz), 4.57-4.51 (1H, m), 3.93 (3H, s), 3.71 (3H, s), 2.24 (3H, s), 2.14 (3H, s), 1.35 (6H, d, J=6.0 Hz).

Reference Production Example 11

A mixture of 7.4 g of 1,4-dimethyl-3-(4-isopropoxy-3-methylphenyl)-5-methoxy-1H-pyrazole mentioned in Reference Production Example 10 and 100 mL of an aqueous 30% sulfuric acid solution 100 mL was stirred with heating under reflux for 15 hours. After cooling to 0° C., the precipitate thus produced was filtered and the precipitate was washed with ice water to obtain a solid. Again, the filtrate was concentrated under reduced pressure down to a half its volume. After cooling to 0° C., the precipitate thus produced was filtered and the precipitate was washed with ice water to obtain a solid. This operation was performed four times and the entired solid thus obtained was dried under reduced pressure to obtain 6.4 g of 4-(1,4-dimethyl-5-methoxy-1H-pyrazol-3-yl)-2-methylphenol.

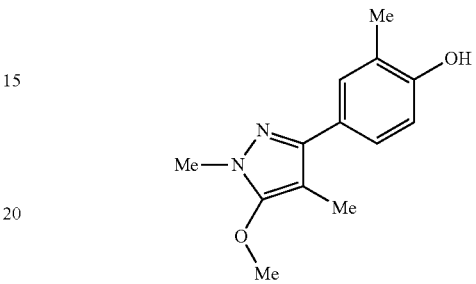

$^1$H-NMR (DMSO-D$_6$) δ: 9.33 (1H, s), 7.29 (1H, s), 7.20 (1H, d, J=8.2 Hz), 6.79 (1H, d, J=8.2 Hz), 3.87 (3H, s), 3.60 (3H, s), 2.14 (3H, s), 2.04 (3H, s).

Reference Production Example 12

A similar reaction was performed as in Reference Production Example 5 using 1-(3-chloro-4-hydroxyphenyl)ethanone in place of 1-(4-hydroxy-3-methylphenyl)ethanone to obtain 1-(3-chloro-4-isopropoxyphenyl)ethanone.

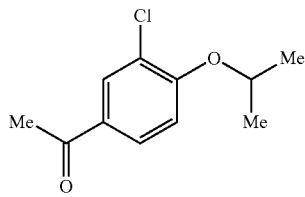

$^1$H-NMR (CDCl$_3$) δ: 7.99 (1H, d, J=2.2 Hz), 7.83 (1H, dd, J=8.7, 2.2 Hz), 6.96 (1H, d, J=8.7 Hz), 4.73-4.64 (1H, m), 2.55 (3H, s), 1.42 (6H, d, J=6.3 Hz).

Reference Production Example 13

A similar reaction was performed as in Reference Production Example 6 using 1-(3-chloro-4-isopropoxyphenyl)ethanone mentioned in Reference Production Example 12 in place of 1-(4-isopropoxy-3-methylphenyl)ethanone to obtain 3-(3-chloro-4-isopropoxyphenyl)-3-oxo-propionic acid ethyl ester.

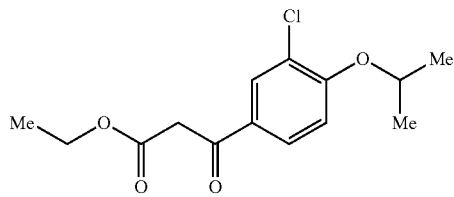 [SMILES: CCOC(=O)CC(=O)c1ccc(OC(C)C)c(Cl)c1]

$^1$H-NMR (CDCl$_3$) δ: 7.98 (1H, d, J=2.4 Hz), 7.83 (1H, dd, J=8.7, 2.2 Hz), 6.96 (1H, d, J=8.7 Hz), 4.72-4.62 (1H, m), 4.22 (2H, q, J=7.1 Hz), 3.92 (2H, s), 1.42 (6H, d, J=6.0 Hz), 1.27 (3H, t, J=7.1 Hz).

Reference Production Example 14

A similar reaction was performed as in Reference Production Example 7 using 3-(3-chloro-4-isopropoxyphenyl)-3-oxopropionic acid ethyl ester mentioned in Reference Production Example 13 in place of 3-(4-isopropoxy-3-methylphenyl)-3-oxo-propionic acid ethyl ester to obtain 5-hydroxy-3-(3-chloro-4-isopropoxyphenyl)-1-methyl-1H-pyrazole.

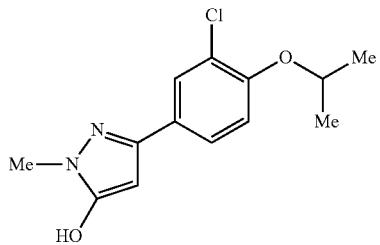 [SMILES: CC(C)Oc1ccc(-c2cc(O)n(C)n2)cc1Cl]

$^1$H-NMR (DMSO-D$_6$) δ: 7.77 (1H, d, J=1.9 Hz), 7.65-7.62 (1H, m), 7.18 (1H, d, J=8.7 Hz), 5.90 (1H, s), 4.72-4.66 (1H, m), 3.58 (3H, s), 1.30 (6H, d, J=6.0 Hz).

Reference Production Example 15

A similar reaction was performed as in Reference Production Example 8 using 5-hydroxy-3-(3-chloro-4-isopropoxyphenyl)-1-methyl-1H-pyrazole mentioned in Reference Production Example 14 in place of 5-hydroxy-3-(4-isopropoxy-3-methylphenyl)-1-methyl-1H-pyrazole to obtain 5-chloro-4-formyl-3-(3-chloro-4-isopropoxyphenyl)-1-methyl-1H-pyrazole.

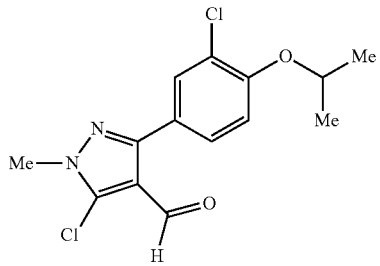 [SMILES: CC(C)Oc1ccc(-c2nn(C)c(Cl)c2C=O)cc1Cl]

$^1$H-NMR (CDCl$_3$) δ: 9.93 (1H, s), 7.84-7.83 (1H, m), 7.69-7.66 (1H, m), 7.00 (1H, d, J=8.7 Hz), 4.66-4.60 (1H, m), 3.93 (3H, s), 1.41 (6H, d, J=6.2 Hz).

Reference Production Example 16

A similar reaction was performed as in Reference Production Example 9 using 5-chloro-4-formyl-3-(3-chloro-4-isopropoxyphenyl)-1-methyl-1H-pyrazole mentioned in Reference Production Example 15 in place of 5-chloro-4-formyl-3-(4-isopropoxy-3-methylphenyl)-1-methyl-1H-pyrazole to obtain 4-formyl-3-(3-chloro-4-isopropoxyphenyl)-5-methoxy-1-methyl-1H-pyrazole.

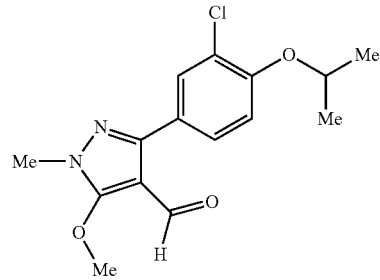 [SMILES: COc1c(C=O)c(-c2ccc(OC(C)C)c(Cl)c2)nn1C]

$^1$H-NMR (CDCl$_3$) δ: 9.75 (1H, s), 7.65 (1H, d, J=2.2 Hz), 7.44 (1H, dd, J=8.5, 2.2 Hz), 7.01 (1H, d, J=8.7 Hz), 4.65-4.59 (1H, m), 4.30 (3H, s), 3.72 (3H, s), 1.42-1.39 (6H, m).

Reference Production Example 17

A similar reaction was performed as in Reference Production Example 10 using 4-formyl-3-(3-chloro-4-isopropoxyphenyl)-5-methoxy-1-methyl-1H-pyrazole mentioned in Reference Production Example 16 in place of 4-formyl-3-(4-isopropoxy-3-methylphenyl)-5-methoxy-1-methyl-1H-pyrazole to obtain 1,4-dimethyl-3-(3-chloro-4-isopropoxyphenyl)-5-methoxy-1H-pyrazole.

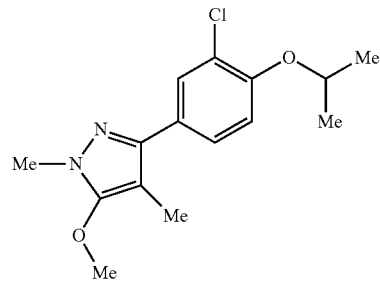 [SMILES: COc1c(C)c(-c2ccc(OC(C)C)c(Cl)c2)nn1C]

$^1$H-NMR (CDCl$_3$) δ: 7.60 (1H, d, J=2.2 Hz), 7.44 (1H, dd, J=8.5, 2.2 Hz), 6.99 (1H, d, J=8.7 Hz), 4.62-4.56 (1H, m), 3.99 (3H, s), 3.75 (3H, s), 2.15 (3H, s), 1.40 (6H, d, J=6.0 Hz).

Reference Production Example 18

A similar reaction was performed as in Reference Production Example 11 using 1,4-dimethyl-3-(3-chloro-4-isopropoxyphenyl)-5-methoxy-1H-pyrazole mentioned in Reference Production Example 17 in place of 1,4-dimethyl-3-(4-isopropoxy-3-methylphenyl)-5-methoxy-1H-pyrazole to obtain 2-chloro-4-(1,4-dimethyl-5-methoxy-1H-pyrazol-3-yl)phenol.

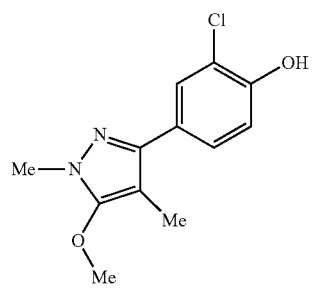 [SMILES: COc1c(C)c(-c2ccc(O)c(Cl)c2)nn1C]

¹H-NMR (DMSO-D₆) δ: 7.50 (1H, d, J=1.9 Hz), 7.37 (1H, dd, J=8.5, 2.2 Hz), 7.00 (1H, d, J=8.5 Hz), 3.89 (3H, s), 3.62 (3H, s), 2.06 (3H, s).

Reference Production Example 19

At room temperature, 2.9 g of sodium thiomethoxide was added to a mixture of 10 g of 5-chloro-4-formyl-3-(4-isopropoxy-3-methylphenyl)-1-methyl-1H-pyrazole mentioned in Reference Production Example 8 and 100 mL of tetrahydrofuran, followed by stirring for 8 hours. To the reaction mixture, 50 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 10.4 g of 4-formyl-3-(4-isopropoxy-3-methylphenyl)-5-methylthio-1-methyl-1H-pyrazole.

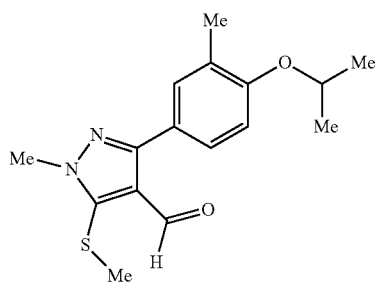 [SMILES: CSc1c(C=O)c(-c2ccc(OC(C)C)c(C)c2)nn1C]

¹H-NMR (CDCl₃) δ: 10.02 (1H, s), 7.50-7.48 (2H, m), 6.91-6.89 (1H, m), 4.62-4.56 (1H, m), 4.02 (3H, s), 2.54 (3H, s), 2.25 (3H, s), 1.36 (6H, d, J=6.0 Hz).

Reference Production Example 20

A similar reaction was performed as in Reference Production Example 10 using 4-formyl-3-(4-isopropoxy-3-methylphenyl)-5-methylthio-1-methyl-1H-pyrazole mentioned in Reference Production Example 19 in place of 4-formyl-3-(4-isopropoxy-3-methylphenyl)-5-methoxy-1-methyl-1H-pyrazole to obtain 1,4-dimethyl-3-(4-isopropoxy-3-methylphenyl)-5-methylthio-1H-pyrazole.

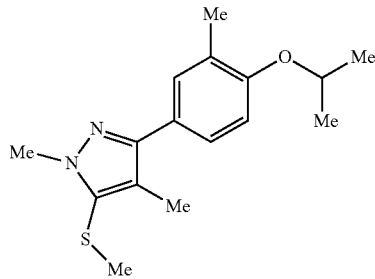 [SMILES: CSc1c(C)c(-c2ccc(OC(C)C)c(C)c2)nn1C]

¹H-NMR (CDCl₃) δ: 7.45 (1H, dd, J=2.2, 0.6 Hz), 7.39 (1H, dd, J=8.5, 2.3 Hz), 6.87 (1H, d, J=8.5 Hz), 4.58-4.52 (1H, m), 3.99 (3H, s), 2.27 (3H, s), 2.26 (3H, s), 2.24 (3H, s), 1.35 (6H, d, J=6.2 Hz).

Reference Production Example 21

A mixture of 8.9 g of 1,4-dimethyl-3-(4-isopropoxy-3-methylphenyl)-5-methylthio-1H-pyrazole mentioned in Reference Production Example 20 and 120 mL of an aqueous 30% sulfuric acid solution was stirred with heating under reflux for 20 hours. After cooling to 0° C., 50 mL of ice water was added and the precipitate thus produced was filtered. The precipitate was washed with ice water and hexane, and then dried under reduced pressure to obtain 7.3 g of 4-(1,4-dimethyl-5-methylthio-1H-pyrazol-3-yl)-2-methylphenol.

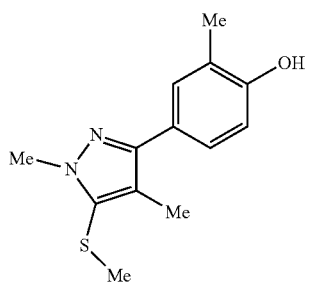 [SMILES: CSc1c(C)c(-c2ccc(O)c(C)c2)nn1C]

¹H-NMR (CDCl₃) δ: 7.44 (1H, d, J=1.6 Hz), 7.33 (1H, dd, J=8.3, 2.2 Hz), 6.80 (1H, d, J=8.2 Hz), 3.99 (3H, s), 2.28 (3H, s), 2.27 (3H, s), 2.26 (3H, s).

Reference Production Example 22

At 0° C., 10 g of propionylchloride and 28 g of triethylamine were added to a mixture of 10 g of o-cresol and 100 mL of chloroform. The temperature of the mixture was raised to room temperature, followed by stirring for 2 hours. After extracting with chloroform, the organic layer was washed with water, dried over anhydrous magnesium, and then concentrated under reduced pressure. The residue thus obtained was subjected to silica gel column chromatography to obtain 14 g of propionic acid-o-toluyl ester.

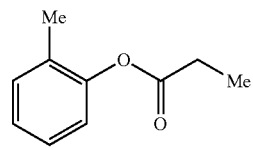 [SMILES: CCC(=O)Oc1ccccc1C]

¹H-NMR (CDCl₃) δ: 7.24-7.18 (2H, m), 7.15-7.11 (1H, m), 7.01-6.99 (1H, m), 2.61 (2H, q, J=7.6 Hz), 2.17 (3H, s), 1.29 (3H, t, J=7.6 Hz).

Reference Production Example 23

At 0° C., 30 g of aluminum trichloride was added to a mixture of 150 mL of nitromethane and 14 g of propionic acid-o-toluyl ester mentioned in Reference Production Example 22. The temperature of the mixture was raised to 50° C., followed by stirring for 12 hours. Ice water (200 mL) was poured into the mixture, followed by extraction with ethyl acetate. The organic layer was washed with water, dried over anhydrous magnesium, and then concentrated under reduced pressure. The residue thus obtained was subjected to silica gel column chromatography to obtain 8.8 g of 1-(4-hydroxy-3-methylphenyl)propan-1-one.

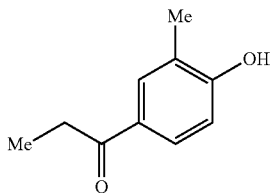 [SMILES: CCC(=O)c1ccc(O)c(C)c1]

¹H-NMR (CDCl₃) δ: 7.80 (1H, d, J=1.9 Hz), 7.75 (1H, dd, J=8.5, 2.2 Hz), 6.86 (1H, d, J=8.5 Hz), 6.65 (1H, s), 2.96 (2H, q, J=7.2 Hz), 2.30 (3H, s), 1.22 (3H, td, J=7.3, 1.3 Hz).

Reference Production Example 24

A mixture of 6.4 g of 1-(2-bromomethylphenyl)-4-methyl-1,4-dihydrotetrazol-5-one mentioned in Reference Production Example 1, 4.1 g of 1-(4-hydroxy-3-methylphenyl)propan-1-one mentioned in Reference Production Example 23, 4.9 g of potassium carbonate, and 100 mL of acetonitrile was stirred with heating under reflux for 11 hours. The reaction mixture was filtered and the filtrate was concentrated, followed by subjecting to silica gel column chromatography to obtain 4.1 g of 1-methyl-4-[2-(2-methyl-4-propionylphenoxymethyl)phenyl]-1,4-dihydrotetrazol-5-one.

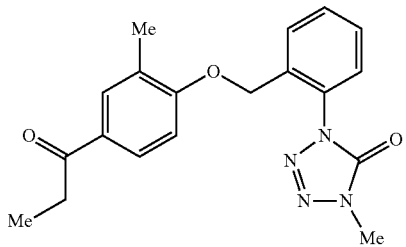 [SMILES: CCC(=O)c1ccc(OCc2ccccc2-n2nnn(C)c2=O)c(C)c1]

¹H-NMR (CDCl₃) δ: 7.78-7.76 (2H, m), 7.69-7.67 (1H, m), 7.56-7.49 (3H, m), 6.84-6.81 (1H, m), 5.23 (2H, s), 3.67 (3H, s), 2.93 (2H, q, J=7.2 Hz), 2.22 (3H, s), 1.19 (3H, t, J=7.2 Hz).

Reference Production Example 25

At room temperature, 2.6 g of potassium tert-butoxide was added to a mixture of 4.1 g of 1-methyl-4-[2-(2-methyl-4-propionylphenoxymethyl)phenyl]-1,4-dihydrotetrazol-5-one mentioned in Reference Production Example 24, 3.4 g of diethyl oxalate, and 100 mL of N,N-dimethylformamide, followed by stirring for 12 hours. After adding 70 mL of water, the mixture was acidified by adding 10% hydrochloric acid and extracted with ethyl acetate. The organic layer was washed with water, dried over anhydrous magnesium sulfate, and then concentrated under reduced pressure. The residue thus obtained was subjected to silica gel chromatography to obtain 2.8 g of 3-methyl-4-{3-methyl-4-[2-(4-methyl-5-oxo-4,5-dihydrotetrazol-1-yl)benzyloxy]phenyl}-2,4-dioxobutyric acid ethyl ester.

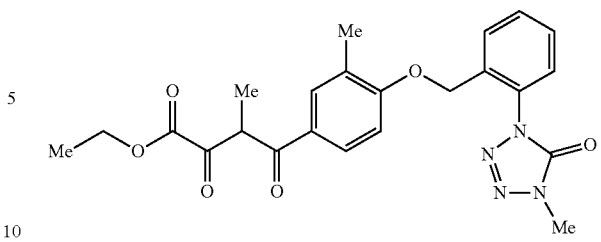

¹H-NMR (CDCl₃) δ: 7.82-7.79 (2H, m), 7.69-7.67 (1H, m), 7.58-7.50 (3H, m), 6.90-6.87 (1H, m), 5.27 (2H, s), 5.00 (1H, q, J=7.1 Hz), 4.27 (2H, q, J=7.2 Hz), 3.69 (3H, s), 2.23 (3H, s), 1.44 (3H, d, J=7.0 Hz), 1.29 (3H, t, J=7.2 Hz).

Reference Production Example 26

At room temperature, 0.31 g of hydrazine monohydrate was added to a mixture of 2.8 g of 3-methyl-4-{3-methyl-4-[2-(4-methyl-5-oxo-4,5-dihydrotetrazol-1-yl)benzyloxy]phenyl}-2,4-dioxobutyric acid butyl ethyl ester mentioned in Reference Production Example 25 and 70 mL of tetrahydrofuran, followed by stirring for 9 hours. The solvent was distilled off and 100 mL of water was charged, followed by stirring for 0.5 hour. The precipitate was collected by filtration, washed with 50 mL of water and 50 mL of hexane, and then dried under reduced pressure to obtain 2.5 g of 1-{2-[2-methyl-4-(5-ethoxycarbonyl-4-methyl-1H-pyrazol-3-yl)phenoxymethyl]phenyl}-4-methyl-1,4-dihydrotetrazol-5-one.

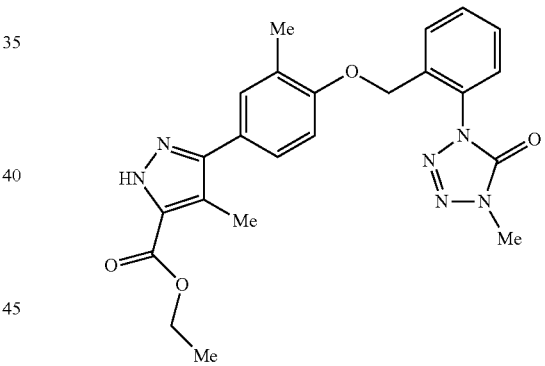

¹H-NMR (CDCl₃) δ: 7.72 (1H, d, J=7.6 Hz), 7.57-7.48 (3H, m), 7.36-7.35 (1H, m), 7.30 (1H, dd, J=8.4, 2.2 Hz), 6.88 (1H, d, J=8.5 Hz), 5.21 (2H, s), 4.41 (2H, q, J=7.2 Hz), 3.69 (3H, s), 2.40 (3H, s), 2.25 (3H, s), 1.42 (3H, t, J=7.1 Hz).

Reference Production Example 27

A mixture of 2.5 g of 1-{2-[2-methyl-4-(5-ethoxycarbonyl-4-methyl-1H-pyrazol-3-yl)phenoxymethyl]phenyl}-4-methyl-1,4-dihydrotetrazol-5-one mentioned in Reference Production Example 26, 2.1 g of dimethyl sulfate, and 30 mL of toluene was stirred at 100° C. for 6 hours. At room temperature, 10 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 1.8 g of 1-{2-[2-methyl-4-(5-ethoxycarbonyl-1,4- dimethyl-1H-pyrazol-3-yl)phenoxymethyl]phenyl}-4-methyl-1,4-dihydrotetrazol-5-one.

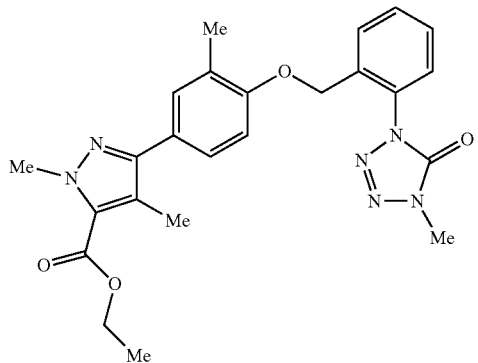 [SMILES: CCOC(=O)c1c(C)c(-c2ccc(OCc3ccccc3-n3nnn(C)c3=O)c(C)c2)nn1C]

¹H-NMR (CDCl₃) δ: 7.72 (1H, d, J=7.1 Hz), 7.56-7.48 (3H, m), 7.38-7.38 (1H, m), 7.29 (1H, dd, J=8.5, 2.1 Hz), 6.85 (1H, d, J=8.5 Hz), 5.20 (2H, s), 4.39 (2H, q, J=7.1 Hz), 4.17 (3H, s), 3.68 (3H, s), 2.35 (3H, s), 2.24 (3H, s), 1.42 (3H, t, J=7.1 Hz).

Reference Production Example 28

At room temperature, 0.28 g of lithium hydroxide was added to a mixture of 1.8 g of 1-{2-[2-methyl-4-(5-ethoxycarbonyl-1,4-dimethyl-1H-pyrazol-3-yl)phenoxymethyl]phenyl}-4-methyl-1,4-dihydrotetrazol-5-one mentioned in Reference Production Example 27, 30 mL of tetrahydrofuran, 10 mL of methanol, and 10 mL of water, followed by stirring for 12 hours. The solvent was distilled off under reduced pressure. After adding 30 mL of 10% hydrochloric acid, the precipitate was collected by filtration, washed with water and hexane, and then dried under reduced pressure to obtain 1.2 g of 2,4-dimethyl-5-{3-methyl-4-[2-(4-methyl-5-oxo-4,5-dihydrotetrazol-1-yl)benzyloxy]phenyl}-2H-pyrazole-3-carboxylic acid.

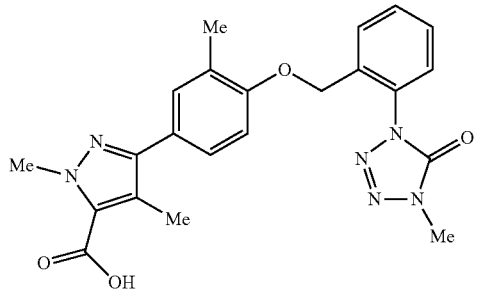 [SMILES: Cc1cc(-c2nn(C)c(C(=O)Cl)c2C)ccc1OCc1ccccc1-n1nnn(C)c1=O]

¹H-NMR (DMSO-D₆) δ: 7.78 (1H, d, J=7.5 Hz), 7.66-7.61 (1H, m), 7.59-7.55 (2H, m), 7.36-7.35 (1H, m), 7.31 (1H, dd, J=8.4, 2.3 Hz), 6.99 (1H, d, J=8.6 Hz), 5.22 (2H, s), 4.05 (3H, s), 3.58 (3H, s), 2.30 (3H, s), 2.12 (3H, s).

Reference Production Example 29

At room temperature, 0.53 g of oxalyl dichloride and 0.1 mL of N,N-dimethylformamide were added to a mixture of 1.2 g of 2,4-dimethyl-5-{3-methyl-4-[2-(4-methyl-5-oxo-4,5-dihydrotetrazol-1-yl)benzyloxy]phenyl}-2H-pyrazole-3-carboxylic acid mentioned in Reference Production Example 28 and 25 mL of tetrahydrofuran, followed by stirring for 3 hours. The solvent was distilled off to obtain 1.2 g of 2,4-dimethyl-5-{3-methyl-4-[2-(4-methyl-5-oxo-4,5-dihydrotetrazol-1-yl)benzyloxy]phenyl}-2H-pyrazole-3-carbonyl chloride.

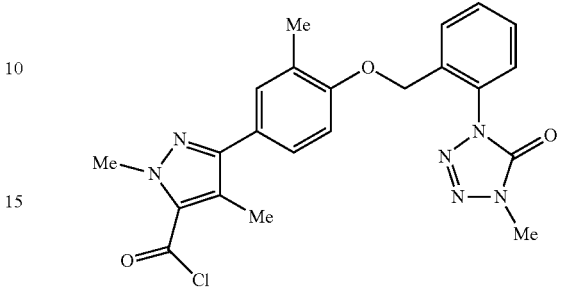

¹H-NMR (CDCl₃) δ: 7.72 (1H, d, J=7.1 Hz), 7.57-7.52 (1H, m), 7.52-7.48 (2H, m), 7.33-7.33 (1H, m), 7.28-7.25 (1H, m), 6.87 (1H, d, J=8.5 Hz), 5.21 (2H, s), 4.15 (3H, s), 3.69 (3H, s), 2.46 (3H, s), 2.25 (3H, s).

Reference Production Example 30

2,4-Dimethyl-5-{3-methyl-4-[2-(4-methyl-5-oxo-4,5-dihydrotetrazol-1-yl)benzyloxy]phenyl}-2H-pyrazole-3-carbonyl chloride (1.2 g) mentioned in Reference Production Example 29 was dissolved in 30 mL of tetrahydrofuran. At room temperature, while stirring 70 mL of an aqueous 28-30% ammonia solution, 30 mL of the tetrahydrofuran solution was added dropwise, followed by stirring for 2 hours. The precipitate was collected by filtration, washed with 30 mL of water and 30 mL of hexane, and then dried under reduced pressure to obtain 1.0 g of 1-{2-[2-methyl-4-(5-aminocarbonyl-1,4-dimethyl-1H-pyrazol-3-yl)phenoxymethyl]phenyl}-4-methyl-1,4-dihydrotetrazol-5-one.

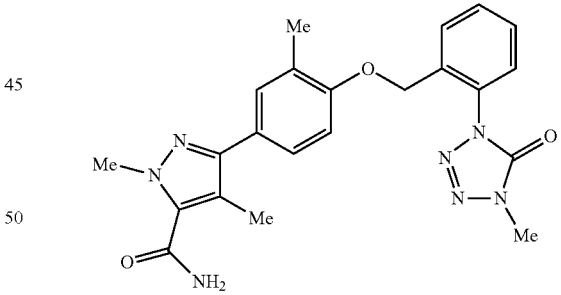

¹H-NMR (CDCl₃) δ: 7.72 (1H, d, J=7.2 Hz), 7.56-7.52 (1H, m), 7.51-7.48 (2H, m), 7.37 (1H, d, J=1.6 Hz), 7.29-7.26 (1H, m), 6.85 (1H, d, J=8.6 Hz), 5.80 (2H, s), 5.20 (2H, s), 4.12 (3H, s), 3.69 (3H, s), 2.34 (3H, s), 2.24 (3H, s).

Reference Production Example 31

A similar reaction was performed as in Reference Production Example 27 using diethyl sulfate in place of dimethyl sulfate to obtain 1-{2-[2-methyl-4-(1-ethyl-5-ethoxycarbonyl-4-methyl-1H-pyrazol-3-yl)phenoxymethyl]phenyl}-4-methyl-1,4-dihydrotetrazol-5-one.

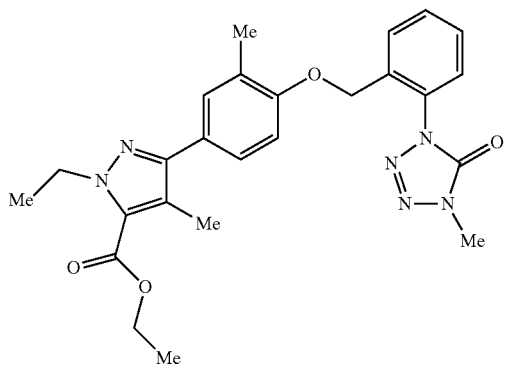 [SMILES: CCOC(=O)c1c(C)c(-c2ccc(OCc3ccccc3-n3nnn(C)c3=O)c(C)c2)nn1CC]

¹H-NMR (CDCl₃) δ: 7.73-7.71 (1H, m), 7.56-7.51 (1H, m), 7.50-7.48 (2H, m), 7.39-7.38 (1H, m), 7.30 (1H, dd, J=8.4, 1.8 Hz), 6.85 (1H, d, J=8.6 Hz), 5.20 (2H, s), 4.58 (2H, q, J=7.2 Hz), 4.39 (2H, q, J=7.2 Hz), 3.69 (3H, s), 2.35 (3H, s), 2.24 (3H, s), 1.43 (6H, q, J=7.2 Hz).

Reference Production Example 32

A similar reaction was performed as in Reference Production Example 28 using 1-{2-[2-methyl-4-(1-ethyl-5-ethoxycarbonyl-4-methyl-1H-pyrazol-3-yl)phenoxymethyl]phenyl}-4-methyl-1,4-dihydrotetrazol-5-one mentioned in Reference Production Example 31 in place of 1-{2-[2-methyl-4-(5-ethoxycarbonyl-1,4-dimethyl-1H-pyrazol-3-yl)phenoxymethyl]phenyl}-4-methyl-1,4-dihydrotetrazol-5-one to obtain 2-ethyl-4-methyl-5-{3-methyl-4-[2-(4-methyl-5-oxo-4,5-dihydrotetrazol-1-yl)benzyloxy]phenyl}-2H-pyrazole-3-carboxylic acid.

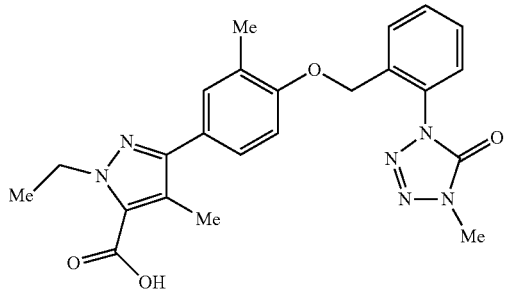 [SMILES: CCn1nc(-c2ccc(OCc3ccccc3-n3nnn(C)c3=O)c(C)c2)c(C)c1C(=O)Cl]

¹H-NMR (CDCl₃) δ: 7.72 (1H, d, J=7.0 Hz), 7.57-7.52 (1H, m), 7.51-7.49 (2H, m), 7.45-7.44 (1H, m), 7.38 (1H, d, J=7.7 Hz), 6.88 (1H, d, J=8.2 Hz), 5.21 (2H, s), 4.76 (2H, q, J=7.1 Hz), 3.71 (3H, s), 2.40 (3H, s), 2.25 (3H, s), 1.50 (3H, t, J=7.1 Hz).

Reference Production Example 33

A similar reaction was performed as in Reference Production Example 29 using 2-ethyl-4-methyl-5-{3-methyl-4-[2-(4-methyl-5-oxo-4,5-dihydrotetrazol-1-yl)benzyloxy]phenyl}-2H-pyrazole-3-carboxylic acid mentioned in Reference Production Example 32 in place of 2,4-dimethyl-5-{3-methyl-4-[2-(4-methyl-5-oxo-4,5-dihydrotetrazol-1-yl)benzyloxy]phenyl}-2H-pyrazole-3-carboxylic acid to obtain 2-ethyl-4-methyl-5-{3-methyl-4-[2-(4-methyl-5-oxo-4,5-dihydrotetrazol-1-yl)benzyloxy]phenyl}-2H-pyrazole-3-carbonyl chloride.

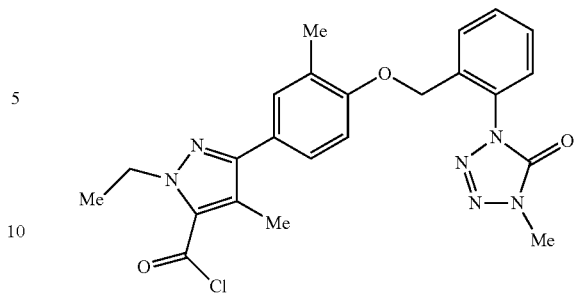

¹H-NMR (CDCl₃) δ: 7.72 (1H, d, J=7.1 Hz), 7.56-7.52 (1H, m), 7.51-7.48 (2H, m), 7.34 (1H, d, J=1.4 Hz), 7.28-7.25 (1H, m), 6.87 (1H, d, J=8.5 Hz), 5.21 (2H, s), 4.53 (2H, q, J=7.1 Hz), 3.69 (3H, s), 2.46 (3H, s), 2.25 (3H, s), 1.44 (3H, t, J=7.1 Hz).

Reference Production Example 34

A similar reaction was performed as in Reference Production Example 30 using 2-ethyl-4-methyl-5-{3-methyl-4-[2-(4-methyl-5-oxo-4,5-dihydrotetrazol-1-yl)benzyloxy]phenyl}-2H-pyrazole-3-carbonyl chloride mentioned in Reference Production Example 33 in place of 2,4-dimethyl-5-{3-methyl-4-[2-(4-methyl-5-oxo-4,5-dihydrotetrazol-1-yl)benzyloxy]phenyl}-2H-pyrazole-3-carbonyl chloride to obtain 1-{2-[2-methyl-4-(5-aminocarbonyl-1-ethyl-4-methyl-1H-pyrazol-3-yl)phenoxymethyl]phenyl}-4-methyl-1,4-dihydrotetrazol-5-one.

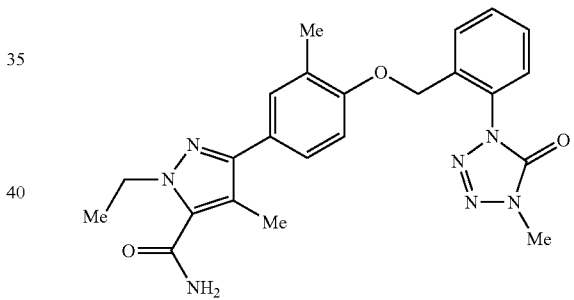

¹H-NMR (CDCl₃) δ: 7.72 (1H, d, J=7.2 Hz), 7.57-7.51 (1H, m), 7.51-7.48 (2H, m), 7.38 (1H, d, J=1.6 Hz), 7.29-7.27 (1H, m), 6.85 (1H, d, J=8.4 Hz), 5.78 (2H, s), 5.20 (2H, s), 4.52 (2H, q, J=7.2 Hz), 3.69 (3H, s), 2.33 (3H, s), 2.24 (3H, s), 1.45 (3H, t, J=7.2 Hz).

Reference Production Example 35

At room temperature, 2.5 g of 55% sodium hydride was added to a mixture of 9.5 g of 5-hydroxy-3-(4-isopropoxy-3-methylphenyl)-1-methyl-1H-pyrazole mentioned in Reference Production Example 7 and 70 mL of N,N-dimethylformamide, followed by stirring for 1 hour. To the reaction mixture, 9.7 g of dimethyl sulfate was added, followed by stirring at 100° C. for 12 hours. To the reaction mixture, 100 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 5.8 g of 5-methoxy-3-(4-isopropoxy-3-methylphenyl)-1-methyl-1H-pyrazole.

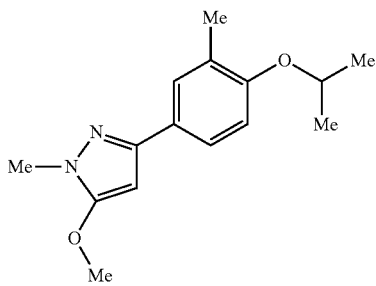 [SMILES: COc1cc(-c2ccc(OC(C)C)c(C)c2)nn1C]

¹H-NMR (CDCl₃) δ: 7.55 (1H, dd, J=2.3, 0.7 Hz), 7.49-7.47 (1H, m), 6.84 (1H, d, J=8.5 Hz), 5.75 (1H, s), 4.56-4.50 (1H, m), 3.92 (3H, s), 3.66 (3H, s), 2.23 (3H, s), 1.34 (6H, d, J=6.2 Hz).

Reference Production Example 36

At room temperature, a mixture of 5.8 g of 5-methoxy-3-(4-isopropoxy-3-methylphenyl)-1-methyl-1H-pyrazole mentioned in Reference Production Example 35, 70 mL of chloroform, and 3.3 g of N-chlorosuccinimide was stirred for 11 hours. To the reaction mixture, 100 mL of water was added and the mixture was extracted with chloroform. The organic layer was washed with water, dried over anhydrous magnesium sulfate, and then concentrated under reduced pressure. The residue thus obtained was subjected to silica gel column chromatography to obtain 5.6 g of 4-chloro-5-methoxy-3-(4-isopropoxy-3-methylphenyl)-1-methyl-1H-pyrazole.

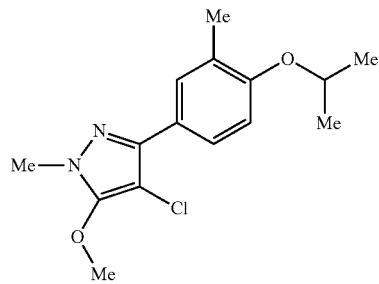 [SMILES: COc1c(Cl)c(-c2ccc(OC(C)C)c(C)c2)nn1C]

¹H-NMR (CDCl₃) δ: 7.62-7.59 (2H, m), 6.88-6.86 (1H, m), 4.59-4.53 (1H, m), 4.11 (3H, s), 3.70 (3H, s), 2.24 (3H, s), 1.35 (6H, d, J=6.0 Hz).

Reference Production Example 37

A mixture of 5.6 g of 4-chloro-5-methoxy-3-(4-isopropoxy-3-methylphenyl)-1-methyl-1H-pyrazole mentioned in Reference Production Example 36 and 120 mL of an aqueous 30% sulfuric acid solution was stirred with heating under reflux for 20 hours. To the reaction mixture, 100 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 1.2 g of 2-methyl-4-(4-chloro-5-methoxy-1-methyl-1H-pyrazol-3-yl)phenol.

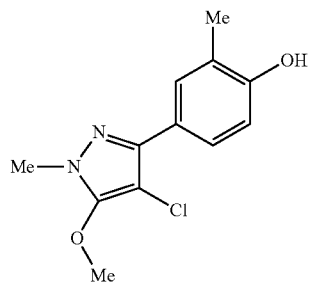 [SMILES: COc1c(Cl)c(-c2ccc(O)c(C)c2)nn1C]

¹H-NMR (CDCl₃) δ: 7.59 (1H, d, J=2.0 Hz), 7.55 (1H, dd, J=8.4, 2.0 Hz), 6.80 (1H, d, J=8.5 Hz), 5.06 (1H, s), 4.11 (3H, s), 3.70 (3H, s), 2.28 (3H, s).

Reference Production Example 38

At room temperature, 1.6 mL of methanol and 1.7 g of 55% sodium hydride were added to a mixture of 8.91 g of 1-{2-[2-methyl-4-(5-chloro-4-formyl-1-methyl-1H-pyrazol-3-yl)phenoxymethyl]phenyl}-4-methyl-1,4-dihydrotetrazol-5-one mentioned in Reference Production Example 2 and 100 mL of tetrahydrofuran, followed by stirring for 3 hours. To the reaction mixture, 50 mL of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 7.82 g of 1-{2-[2-methyl-4-(4-formyl-5-methoxy-1-methyl-1H-pyrazol-3-yl)phenoxymethyl]phenyl}-4-methyl-1,4-dihydrotetrazol-5-one.

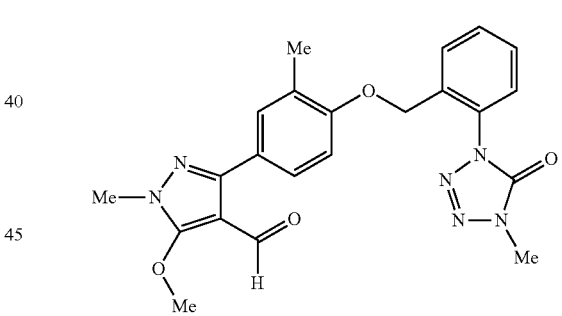

¹H-NMR (CDCl₃) δ: 9.72 (1H, s), 7.72 (1H, d, J=7.6 Hz), 7.56-7.49 (3H, m), 7.39 (1H, s), 7.33 (1H, dd, J=8.6, 2.2 Hz), 6.87 (1H, d, J=8.5 Hz), 5.21 (2H, s), 4.29 (3H, s), 3.71 (3H, s), 3.69 (3H, s), 2.23 (3H, s).

Reference Production Example 39

A mixture of 2.17 g of 1-{2-[2-methyl-4-(4-formyl-5-methoxy-1-methyl-1H-pyrazol-3-yl)phenoxymethyl]phenyl}-4-methyl-1,4-dihydrotetrazol-5-one mentioned in Reference Production Example 38, 0.52 g of hydroxylamine hydrochloride, 1 mL of pyridine, 40 mL of ethanol, and 10 mL of chloroform was stirred with heating at 40° C. for 4 hours. To the reaction mixture, 1N hydrochloric acid was added to thereby adjust to pH2, and then the mixture was extracted with chloroform. The organic layer was washed with water, dried over anhydrous magnesium sulfate, and then concentrated under reduced pressure. The residue thus obtained was subjected to silica gel column chromatography to obtain 1.16 g of 1-{2-[2-methyl-4-(4-carboaldehyde oxime-5-methoxy-1-methyl-1H-pyrazol-3-yl)phenoxymethyl]phenyl}-4-methyl-1,4-dihydrotetrazol-5-one.

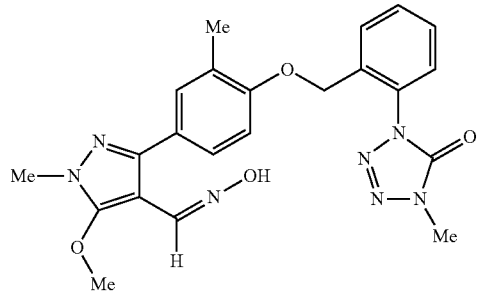 [SMILES: COc1c(C=NO)c(-c2ccc(OCc3ccccc3-n3nnn(C)c3=O)c(C)c2)nn1C]

$^1$H-NMR (CDCl$_3$) δ: 8.08 (1H, s), 7.72 (1H, t, J=3.9 Hz), 7.54-7.49 (3H, m), 7.35 (1H, t, J=1.0 Hz), 7.24 (1H, t, J=1.4 Hz), 6.84 (1H, d, J=8.4 Hz), 5.20 (2H, s), 4.04 (3H, s), 3.75 (3H, s), 3.69 (3H, s), 2.22 (3H, s).

Reference Production Example 40

A similar reaction was performed as in Reference Production Example 7 using 3-{3-methyl-4-[2-(4-methyl-5-oxo-4,5-dihydrotetrazol-1-yl)benzyloxy]phenyl}-3-oxopropionic acid ethyl ester mentioned in Reference Production Example 41 in place of 3-(4-isopropoxy-3-methylphenyl)-3-oxopropionic acid ethyl ester to obtain 7.91 g of 1-{2-[4-(5-hydroxy-1-methyl-1H-pyrazol-3-yl)-2-methylphenoxymethyl]phenyl}-4-methyl-1,4-dihydrotetrazol-5-one.

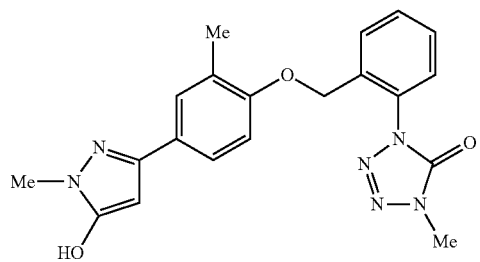 [SMILES: Cc1cc(-c2cc(O)n(C)n2)ccc1OCc1ccccc1-n1nnn(C)c1=O]

$^1$H-NMR (DMSO-D$_6$) δ: 7.77 (1H, d, J=7.1 Hz), 7.65-7.54 (5H, m), 7.02 (1H, d, J=8.5 Hz), 6.10 (1H, s), 5.25 (2H, s), 3.67 (3H, s), 3.58 (3H, s), 2.11 (3H, s).

Reference Production Example 41

A similar reaction was performed as in Reference Production Example 6 using 1-[2-(4-acetyl-2-methylphenoxymethyl)phenyl]-4-methyl-1,4-dihydro-tetrazol-5-one mentioned in Reference Production Example 42 in place of 1-(4-isopropoxy-3-methylphenyl)ethanone to obtain 8.74 g of 3-{3-methyl-4-[2-(4-methyl-5-oxo-4,5-dihydrotetrazol-1-yl)benzyloxy]phenyl}-3-oxopropionic acid ethyl ester.

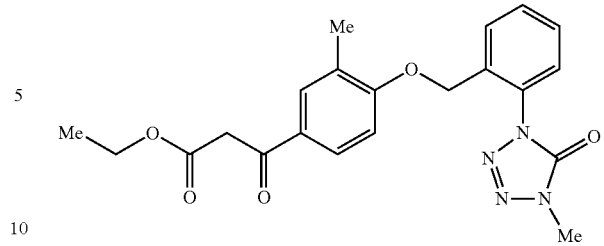

$^1$H-NMR (CDCl$_3$) δ: 7.77-7.74 (2H, m), 7.67 (1H, d, J=6.6 Hz), 7.57-7.50 (3H, m), 6.85 (1H, d, J=8.2 Hz), 5.25 (2H, s), 4.21 (2H, q, J=7.2 Hz), 3.93 (2H, s), 3.68 (3H, s), 2.22 (3H, s), 1.26 (3H, t, J=7.1 Hz).

Reference Production Example 42

A similar reaction was performed as in Production Example 1 using 1-(4-hydroxy-3-methylphenyl)ethanone in place of 2-chloro-4-(5-methoxy-1,4-dimethyl-1H-pyrazol-3-yl)phenol to obtain 17.7 g of 1-[2-(4-acetyl-2-methylphenoxymethyl)phenyl]-4-methyl-1,4-dihydro-tetrazol-5-one.

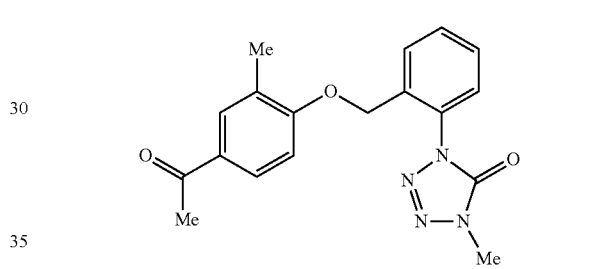

$^1$H-NMR (CDCl$_3$) δ: 7.78-7.75 (2H, m), 7.68 (1H, d, J=6.6 Hz), 7.57-7.49 (3H, m), 6.83 (1H, d, J=8.7 Hz), 5.25 (2H, s), 3.68 (3H, s), 2.54 (3H, s), 2.22 (3H, s).

Reference Production Example 43

A similar reaction was performed as in Reference Production Example 11 using 3-(4-isopropoxy-2,5-dimethylphenyl)-5methoxy-1-methyl-1H-pyrazole mentioned in Reference Production Example 44 in place of 1,4-dimethyl-3-(4-isopropoxy-3-methylphenyl)-5-methoxy-1H-pyrazole to obtain 0.68 g of 4-(5-methoxy-1-methyl-1H-pyrazol-3-yl)-2,5-dimethylphenol.

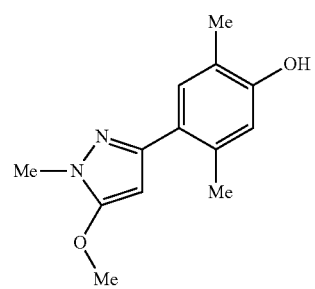 [SMILES: COc1cc(-c2cc(C)c(O)cc2C)nn1C]

$^1$H-NMR (CDCl$_3$) δ: 6.96 (1H, s), 6.71 (1H, s), 5.58 (1H, s), 3.91 (3H, s), 3.49 (3H, s), 2.23 (3H, s), 2.11 (3H, s).

Reference Production Example 44

A similar reaction was performed as in Reference Production Example 35 using 5-(4-isopropoxy-2,5-dimethylphenyl)-2-methyl-2H-pyrazol-3-ol mentioned in Reference Production Example 45 in place of 5-hydroxy-3-(4-isopropoxy-3-methylphenyl)-1-methyl-1H-pyrazole to obtain 0.68 g of 3-(4-isopropoxy-2,5-dimethylphenyl)-5methoxy-1-methyl-1H-pyrazole.

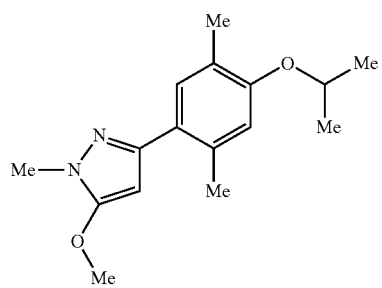 [SMILES: COc1cc(-c2cc(C)c(OC(C)C)cc2C)nn1C]

$^1$H-NMR (CDCl$_3$) δ: 6.96 (1H, s), 6.72 (1H, s), 5.57 (1H, s), 4.56 (1H, sept, J=6.1 Hz), 3.91 (3H, s), 3.49 (3H, s), 2.17 (3H, s), 2.15 (3H, s), 1.37 (6H, d, J=6.2 Hz).

Reference Production Example 45

A similar reaction was performed as in Reference Production Example 7 using 3-(4-isopropoxy-2,5-dimethylphenyl)-3-oxopropionic acid ethyl ester mentioned in Reference Production Example 46 in place of 3-(4-isopropoxy-3-methylphenyl)-3-oxopropionic acid ethyl ester to obtain 33.5 g of 5-(4-isopropoxy-2,5-dimethylphenyl)-2-methyl-2H-pyrazol-3-ol.

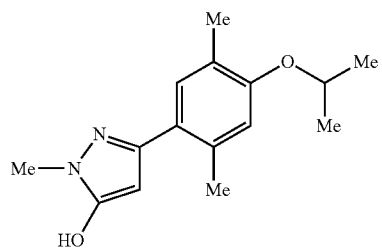 [SMILES: Cc1cc(-c2cc(O)n(C)n2)c(C)cc1OC(C)C]

$^1$H-NMR (CDCl$_3$) δ: 6.98 (1H, s), 6.73 (1H, s), 5.57 (1H, s), 4.57 (1H, sept, J=6.0 Hz), 3.49 (3H, s), 2.18 (3H, s), 2.17 (3H, s), 1.37 (6H, d, J=6.1 Hz).

Reference Production Example 46

A similar reaction was performed as in Reference Production Example 6 using 1-(4-isopropoxy-2,5-dimethylphenyl)ethanone mentioned in Reference Production Example 47 in place of 1-(4-isopropoxy-3-methylphenyl)ethanone to obtain 44.3 g of 3-(4-isopropoxy-2,5-dimethylphenyl)-3-oxopropionic acid ethyl ester.

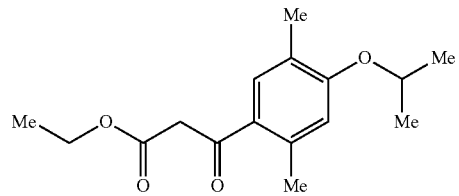 [SMILES: CCOC(=O)CC(=O)c1cc(C)c(OC(C)C)cc1C]

$^1$H-NMR (CDCl$_3$) δ: 7.51 (1H, s), 6.66 (1H, s), 4.64 (1H, sept, J=6.0 Hz), 4.21 (2H, q, J=7.2 Hz), 3.93 (2H, s), 2.56 (3H, s), 2.18 (3H, s), 1.36 (6H, d, J=6.1 Hz), 1.26 (3H, t, J=7.1 Hz).

Reference Production Example 47

A similar reaction was performed as in Reference Production Example 5 using 1-(2,5-dimethyl-4-hydroxyphenyl)ethanone in place of 1-(4-hydroxy-3-methylphenyl)ethanone to obtain 30.9 g of 1-(4-isopropoxy-2,5-dimethylphenyl)ethanone.

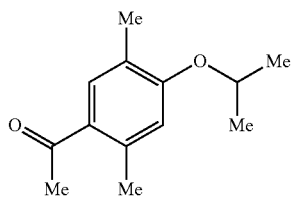 [SMILES: CC(=O)c1cc(C)c(OC(C)C)cc1C]

$^1$H-NMR (CDCl$_3$) δ: 7.58 (1H, s), 6.65 (1H, s), 4.63 (1H, sept, J=6.1 Hz), 2.54 (3H, s), 2.54 (3H, s), 2.19 (3H, s), 1.36 (6H, d, J=6.0 Hz).

According to the above-mentioned processes, compounds EP1A-001 to EP1N-342 can be obtained.

The compounds EP1A-001 to EP1N-342 are respectively compounds represented by the following formulas:

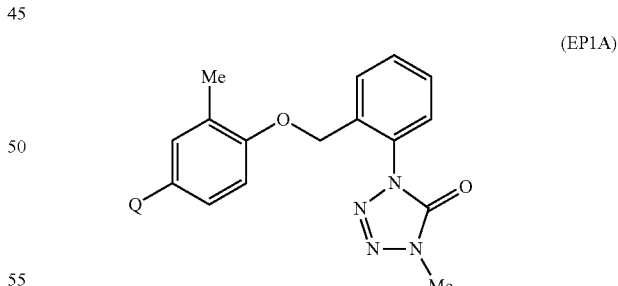

(EP1A)

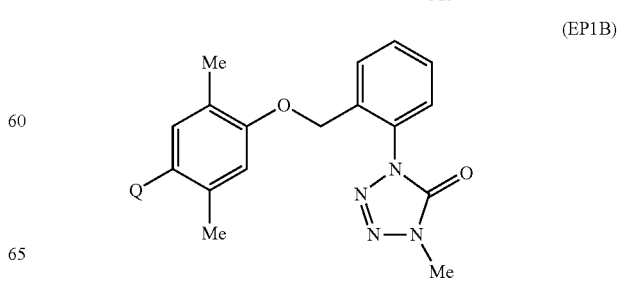

(EP1B)

(EP1C) 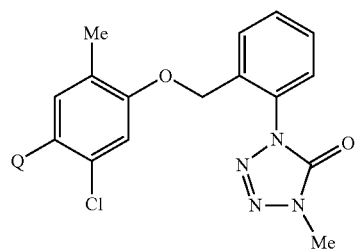
(EP1D) 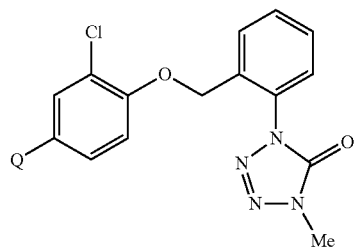
(EP1E) 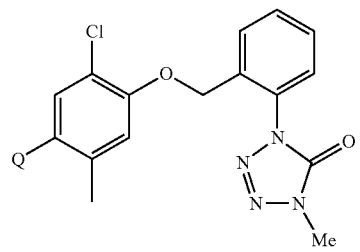
(EP1F) 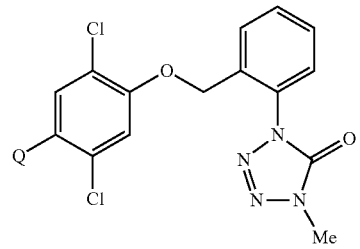
(EP1G) 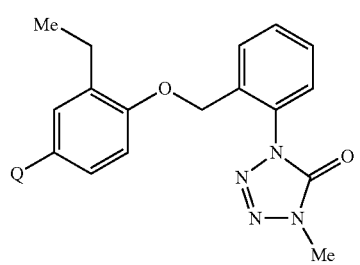
(EP1H) 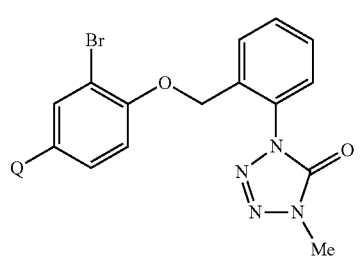
(EP1I) 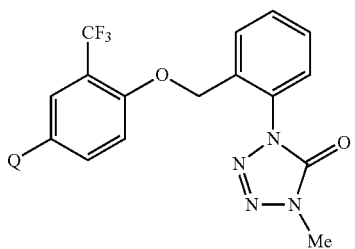
(EP1J) 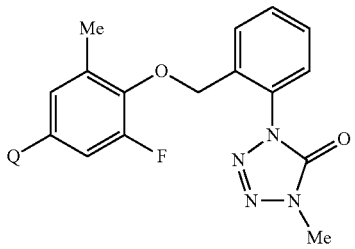
(EP1K) 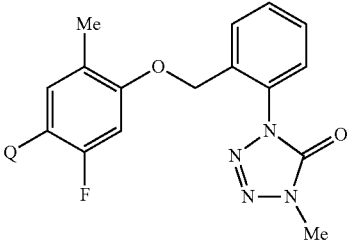
(EP1L) 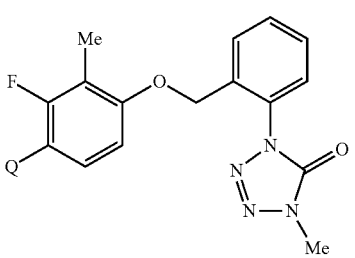
(EP1M) 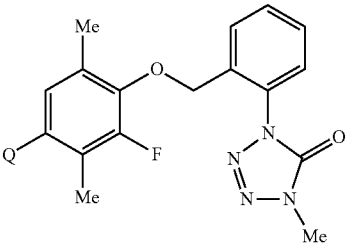
(EP1N) 
wherein Q is a substituent corresponding to each of substituent numbers 1 to 342 shown below.
[substituent number; Q], [1; 5-methoxy-1-methyl-1H-pyrazol-3-yl group], [2; 5-methoxy-1,4-dimethyl-1H-pyrazol-3- yl group], [3; 4-ethyl-5-methoxy-1-methyl-1H-pyrazol-3-yl group], [4; 5-methoxy-1-methyl-4-propyl-1H-pyrazol-3-yl group], [5; 4-isopropyl-5-methoxy-1-methyl-1H-pyrazol-3-yl group], [6; 4-fluoro-5-methoxy-1-methyl-1H-pyrazol-3-yl group], [7; 4-chloro-5-methoxy-1-methyl-1H-pyrazol-3-yl group], [8; 4-bromo-5-methoxy-1-methyl-1H-pyrazol-3-yl group], [9; 4-iodo-5-methoxy-1-methyl-1H-pyrazol-3-yl group], [10; 4-cyano-5-methoxy-1-methyl-1H-pyrazol-3-yl group], [11; 5-ethoxy-1-methyl-1H-pyrazol-3-yl group], [12; 1,4-dimethyl-5-ethoxy-1H-pyrazol-3-yl group], [13; 4-ethyl-5-ethoxy-1-methyl-1H-pyrazol-3-yl group], [14; 5-ethoxy-1-methyl-4-propyl-1H-pyrazol-3-yl group], [15; 5-ethoxy-4-isopropyl-1-methyl-1H-pyrazol-3-yl group], [16; 5-ethoxy-4-fluoro-1-methyl-1H-pyrazol-3-yl group], [17; 4-chloro-5-ethoxy-1-methyl-1H-pyrazol-3-yl group], [18; 4-bromo-5-ethoxy-1-methyl-1H-pyrazol-3-yl group], [19; 5-ethoxy-4-iodo-1-methyl-1H-pyrazol-3-yl group], [20; 4-cyano-5-ethoxy-1-methyl-1H-pyrazol-3-yl group], [21; 1-methyl-5-propoxy-1H-pyrazol-3-yl group], [22; 1,4-dimethyl-5-propoxy-1H-pyrazol-3-yl group], [23; 4-fluoro-1-methyl-5-propoxy-1H-pyrazol-3-yl group], [24; 4-chloro-1-methyl-5-propoxy-1H-pyrazol-3-yl group], [25; 5-isopropoxy-1-methyl-1H-pyrazol-3-yl group], [26; 1,4-dimethyl-5-isopropoxy-1H-pyrazol-3-yl group], [27; 4-fluoro-5-isopropoxy-1-methyl-1H-pyrazol-3-yl group], [28; 4-chloro-5-isopropoxy-1-methyl-1H-pyrazol-3-yl group], [29; 5-difluoromethoxy-1-methyl-1H-pyrazol-3-yl group], [30; 5-difluoromethoxy-1,4-dimethyl-1H-pyrazol-3-yl group]

[substituent number; Q], [31; 5-difluoromethoxy-4-ethyl-1-methyl-1H-pyrazol-3-yl group], [32; 5-difluoromethoxy-1-methyl-4-propyl-1H-pyrazol-3-yl group], [33; 5-difluoromethoxy-4-isopropyl-1-methyl-1H-pyrazol-3-yl group], [34; 5-difluoromethoxy-4-fluoro-1-methyl-1H-pyrazol-3-yl group], [35; 4-chloro-5-difluoromethoxy-1-methyl-1H-pyrazol-3-yl group], [36; 4-bromo-5-difluoromethoxy-1-methyl-1H-pyrazol-3-yl group], [37; 5-difluoromethoxy-4-iodo-1-methyl-1H-pyrazol-3-yl group], [38; 4-cyano-5-difluoromethoxy-1-methyl-1H-pyrazol-3-yl group], [39; 5-(2,2-difluoroethoxy)-1-methyl-1H-pyrazol-3-yl group], [40; 5-(2,2-difluoroethoxy)-1,4-dimethyl-1H-pyrazol-3-yl group], [41; 5-(2,2-difluoroethoxy)-4-fluoro-1-methyl-1H-pyrazol-3-yl group], [42; 4-chloro-5-(2,2-difluoroethoxy)-1-methyl-1H-pyrazol-3-yl group], [43; 1-methyl-5-trifluoromethoxy-1H-pyrazol-3-yl group], [44; 1,4-dimethyl-5-trifluoromethoxy-1H-pyrazol-3-yl group], [45; 4-ethyl-1-methyl-5-trifluoromethoxy-1H-pyrazol-3-yl group], [46; 1-methyl-4-propyl-5-trifluoromethoxy-1H-pyrazol-3-yl group], [47; 4-isopropyl-1-methyl-5-trifluoromethoxy-1H-pyrazol-3-yl group], [48; 4-fluoro-1-methyl-5-trifluoromethoxy-1H-pyrazol-3-yl group], [49; 4-chloro-1-methyl-5-trifluoromethoxy-1H-pyrazol-3-yl group], [50; 4-bromo-1-methyl-5-trifluoromethoxy-1H-pyrazol-3-yl group], [51; 4-iodo-1-methyl-5-trifluoromethoxy-1H-pyrazol-3-yl group], [52; 4-cyano-1-methyl-5-trifluoromethoxy-1H-pyrazol-3-yl group], [53; 1-methyl-5-(2,2,2-trifluoroethoxy)-1H-pyrazol-3-yl group], [54; 1,4-dimethyl-5-(2,2,2-trifluoroethoxy)-1H-pyrazol-3-yl group], [55; 4-fluoro-1-methyl-5-(2,2,2-trifluoroethoxy)-1H-pyrazol-3-], [56; 4-chloro-1-methyl-5-(2,2,2-trifluoroethoxy)-1H-pyrazol-3-i], [57; 1-methyl-5-(2-propynyloxy)-1H-pyrazol-3-yl group], [58; 1,4-dimethyl-5-(2-propynyloxy)-1H-pyrazol-3-yl group], [59; 4-ethyl-1-methyl-5-(2-propynyloxy)-1H-pyrazol-3-yl group], [60; 1-methyl-4-propyl-5-(2-propynyloxy)-1H-pyrazol-3-yl group]

[substituent number; Q], [61; 4-isopropyl-1-methyl-5-(2-propynyloxy)-1H-pyrazol-3-yl group], [62; 4-fluoro-1-methyl-5-(2-propynyloxy)-1H-pyrazol-3-yl group], [63; 4-chloro-1-methyl-5-(2-propynyloxy)-1H-pyrazol-3-yl group], [64; 4-bromo-1-methyl-5-(2-propynyloxy)-1H-pyrazol-3-yl group], [65; 4-iodo-1-methyl-5-(2-propynyloxy)-1H-pyrazol-3-yl group], [66; 4-cyano-1-methyl-5-(2-propynyloxy)-1H-pyrazol-3-yl group], [67; 5-(2-butynyloxy)-1-methyl-1H-pyrazol-3-yl group], [68; 5-(2-butynyloxy)-1,4-dimethyl-1H-pyrazol-3-yl group], [69; 5-(2-butynyloxy)-4-fluoro-1-methyl-1H-pyrazol-3-yl group], [70; 5-(2-butynyloxy)-4-chloro-1-methyl-1H-pyrazol-3-yl group], [71; 5-(3-butynyloxy)-1-methyl-1H-pyrazol-3-yl group], [72; 5-(3-butynyloxy)-1,4-dimethyl-1H-pyrazol-3-yl group], [73; 5-(3-butynyloxy)-4-fluoro-1-methyl-1H-pyrazol-3-yl group], [74; 5-(3-butynyloxy)-4-chloro-1-methyl-1H-pyrazol-3-yl group], [75; 5-methylthio-1-methyl-1H-pyrazol-3-yl group], [76; 1,4-dimethyl-5-methylthio-1H-pyrazol-3-yl group], [77; 4-ethyl-5-methylthio-1-methyl-1H-pyrazol-3-yl group], [78; 5-methylthio-1-methyl-4-propyl-1H-pyrazol-3-yl group], [79; 4-isopropyl-5-methylthio-1-methyl-1H-pyrazol-3-yl group], [80; 4-fluoro-5-methylthio-1-methyl-1H-pyrazol-3-yl group], [81; 4-chloro-5-methylthio-1-methyl-1H-pyrazol-3-yl group], [82; 4-bromo-5-methylthio-1-methyl-1H-pyrazol-3-yl group], [83; 4-iodo-5-methylthio-1-methyl-1H-pyrazol-3-yl group], [84; 4-cyano-5-methylthio-1-methyl-1H-pyrazol-3-yl group], [85; 5-ethylthio-1-methyl-1H-pyrazol-3-yl group], [86; 5-ethylthio-1,4-dimethyl-1H-pyrazol-3-yl group], [87; 5-ethylthio-4-fluoro-1-methyl-1H-pyrazol-3-yl group], [88; 4-chloro-5-ethylthio-1-methyl-1H-pyrazol-3-yl group], [89; 5-difluoromethylthio-1-methyl-1H-pyrazol-3-yl group], [90; 5-difluoromethylthio-1,4-dimethyl-1H-pyrazol-3-yl group]

[substituent number; Q], [91; 5-difluoromethylthio-4-ethyl-1-methyl-1H-pyrazol-3-yl group], [92; 5-difluoromethylthio-1-methyl-4-propyl-1H-pyrazol-3-yl group], [93; 5-difluoromethylthio-4-isopropyl-1-methyl-1H-pyrazol-3-yl group], [94; 5-difluoromethylthio-4-fluoro-1-methyl-1H-pyrazol-3-yl group], [95; 4-chloro-5-difluoromethylthio-1-methyl-1H-pyrazol-3-yl group], [96; 4-bromo-5-difluoromethylthio-1-methyl-1H-pyrazol-3-yl group], [97; 5-difluoromethylthio-4-iodo-1-methyl-1H-pyrazol-3-yl group], [98; 4-cyano-5-difluoromethylthio-1-methyl-1H-pyrazol-3-yl group], [99; 1-methyl-5-trifluoromethylthio-1H-pyrazol-3-yl group], [100; 1,4-dimethyl-5-trifluoromethylthio-1H-pyrazol-3-yl group], [101; 4-ethyl-1-methyl-5-trifluoromethylthio-1H-pyrazol-3-yl group], [102; 1-methyl-4-propyl-5-trifluoromethylthio-1H-pyrazol-3-yl group], [103; 4-isopropyl-1-methyl-5-trifluoromethylthio-1H-pyrazol-3-yl group], [104; 4-fluoro-1-methyl-5-trifluoromethylthio-1H-pyrazol-3-yl group], [105; 4-chloro-1-methyl-5-trifluoromethylthio-1H-pyrazol-3-yl group], [106; 4-bromo-1-methyl-5-trifluoromethylthio-1H-pyrazol-3-yl group], [107; 4-iodo-1-methyl-5-trifluoromethylthio-1H-pyrazol-3-yl group], [108; 4-cyano-1-methyl-5-trifluoromethylthio-1H-pyrazol-3-yl group], [109; 5-dimethylamino-1-methyl-1H-pyrazol-3-yl group], [110; 5-dimethylamino-1,4-dimethyl-1H-pyrazol-3-yl group], [111; 5-dimethylamino-4-fluoro-1-methyl-1H-pyrazol-3-yl group], [112; 4-chloro-5-dimethylamino-1-methyl-1H-pyrazol-3-yl group], [113; 5-diethylamino-1-methyl-1H-pyrazol-3-yl group], [114; 5-diethylamino-1,4-dimethyl-1H-pyrazol-3-yl group], [115; 5-diethylamino-4-fluoro-1-methyl-1H-pyrazol-3-yl group], [116; 4-chloro-5-diethylamino-1-methyl-1H-pyrazol-3-yl group], [117; 5-cyano-1-methyl-1H-pyrazol-3-yl group], [118; 5-cyano-1,4-dimethyl-1H-pyrazol-3-yl group], [119; 5-cyano-4-ethyl- 1-methyl-1H-pyrazol-3-yl group], [120; 5-cyano-1-methyl-4-propyl-1H-pyrazol-3-yl group]

[substituent number; Q], [121; 5-cyano-4-isopropyl-1-methyl-1H-pyrazol-3-yl group], [122; 5-cyano-4-fluoro-1-methyl-1H-pyrazol-3-yl group], [123; 4-chloro-5-cyano-1-methyl-1H-pyrazol-3-yl group], [124; 4-bromo-5-cyano-1-methyl-1H-pyrazol-3-yl group], [125; 5-cyano-4-iodo-1-methyl-1H-pyrazol-3-yl group], [126; 4,5-dicyano-1-methyl-1H-pyrazol-3-yl group], [127; 1-ethyl-5-methoxy-1H-pyrazol-3-yl group], [128; 1-ethyl-5-methoxy-4-methyl-1H-pyrazol-3-yl group], [129; 1-ethyl-4-fluoro-5-methoxy-1H-pyrazol-3-yl group], [130; 4-chloro-1-ethyl-5-methoxy-1H-pyrazol-3-yl group], [131; 5-ethoxy-1-ethyl-1H-pyrazol-3-yl group], [132; 5-ethoxy-1-ethyl-4-methyl-1H-pyrazol-3-yl group], [133; 5-ethoxy-1-ethyl-4-fluoro-1H-pyrazol-3-yl group], [134; 4-chloro-5-ethoxy-1-ethyl-1H-pyrazol-3-yl group], [135; 5-difluoromethoxy-1-ethyl-1H-pyrazol-3-yl group], [136; 5-difluoromethoxy-1-ethyl-4-methyl-1H-pyrazol-3-yl group], [137; 5-difluoromethoxy-1-ethyl-4-fluoro-1H-pyrazol-3-yl group], [138; 4-chloro-5-difluoromethoxy-1-ethyl-1H-pyrazol-3-yl group], [139; 1-ethyl-5-trifluoromethoxy-1H-pyrazol-3-yl group], [140; 1-ethyl-4-methyl-5-trifluoromethoxy-1H-pyrazol-3-yl group], [141; 1-ethyl-4-fluoro-5-trifluoromethoxy-1H-pyrazol-3-yl group], [142; 4-chloro-1-ethyl-5-trifluoromethoxy-1H-pyrazol-3-yl group], [143; 1-ethyl-5-(2-propynyloxy)-1H-pyrazol-3-yl group], [144; 1-ethyl-4-methyl-5-(2-propynyloxy)-1H-pyrazol-3-yl group], [145; 1-ethyl-4-fluoro-5-(2-propynyloxy)-1H-pyrazol-3-yl group], [146; 4-chloro-1-ethyl-5-(2-propynyloxy)-1H-pyrazol-3-yl group], [147; 1-ethyl-5-methylthio-1H-pyrazol-3-yl group], [148; 1-ethyl-5-methylthio-4-methyl-1H-pyrazol-3-yl group], [149; 1-ethyl-4-fluoro-5-methylthio-1H-pyrazol-3-yl group], [150; 4-chloro-1-ethyl-5-methylthio-1H-pyrazol-3-yl group]

[substituent number; Q], [151; 5-difluoromethylthio-1-ethyl-1H-pyrazol-3-yl group], [152; 5-difluoromethylthio-1-ethyl-4-methyl-1H-pyrazol-3-yl group], [153; 5-difluoromethylthio-1-ethyl-4-fluoro-1H-pyrazol-3-yl group], [154; 4-chloro-5-difluoromethylthio-1-ethyl-1H-pyrazol-3-yl group], [155; 1-ethyl-5-trifluoromethylthio-1H-pyrazol-3-yl group], [156; 1-ethyl-4-methyl-5-trifluoromethylthio-1H-pyrazol-3-yl group], [157; 1-ethyl-4-fluoro-5-trifluoromethylthio-1H-pyrazol-3-yl group], [158; 4-chloro-1-ethyl-5-trifluoromethylthio-1H-pyrazol-3-yl group], [159; 5-cyano-1-ethyl-1H-pyrazol-3-yl group], [160; 5-cyano-1-ethyl-4-methyl-1H-pyrazol-3-yl group], [161; 5-cyano-1-ethyl-4-fluoro-1H-pyrazol-3-yl group], [162; 4-chloro-5-cyano-1-ethyl-1H-pyrazol-3-yl group], [163; 5-methoxy-1-propyl-1H-pyrazol-3-yl group], [164; 5-methoxy-4-methyl-1-propyl-1H-pyrazol-3-yl group], [165; 4-fluoro-5-methoxy-1-propyl-1H-pyrazol-3-yl group], [166; 4-chloro-5-methoxy-1-propyl-1H-pyrazol-3-yl group], [167; 5-ethoxy-1-propyl-1H-pyrazol-3-yl group], [168; 5-ethoxy-4-methyl-1-propyl-1H-pyrazol-3-yl group], [169; 5-ethoxy-4-fluoro-1-propyl-1H-pyrazol-3-yl group], [170; 4-chloro-5-ethoxy-1-propyl-1H-pyrazol-3-yl group], [171; 5-difluoromethoxy-1-propyl-1H-pyrazol-3-yl group], [172; 5-difluoromethoxy-4-methyl-1-propyl-1H-pyrazol-3-yl group], [173; 5-difluoromethoxy-4-fluoro-1-propyl-1H-pyrazol-3-yl group], [174; 4-chloro-5-difluoromethoxy-1-propyl-1H-pyrazol-3-yl group], [175; 1-propyl-5-trifluoromethoxy-1H-pyrazol-3-yl group], [176; 4-methyl-1-propyl-5-trifluoromethoxy-1H-pyrazol-3-yl group], [177; 4-fluoro-1-propyl-5-trifluoromethoxy-1H-pyrazol-3-yl group], [178; 4-chloro-1-propyl-5-trifluoromethoxy-1H-pyrazol-3-yl group], [179; 1-propyl-5-(2-propynyloxy)-1H-pyrazol-3-yl group], [180; 4-methyl-1-propyl-5-(2-propynyloxy)-1H-pyrazol-3-yl group]

[substituent number; Q], [181; 4-fluoro-1-propyl-5-(2-propynyloxy)-1H-pyrazol-3-yl group], [182; 4-chloro-1-propyl-5-(2-propynyloxy)-1H-pyrazol-3-yl group], [183; 5-methylthio-1-propyl-1H-pyrazol-3-yl group], [184; 5-methylthio-4-methyl-1-propyl-1H-pyrazol-3-yl group], [185; 4-fluoro-5-methylthio-1-propyl-1H-pyrazol-3-yl group], [186; 4-chloro-5-methylthio-1-propyl-1H-pyrazol-3-yl group], [187; 5-difluoromethylthio-1-propyl-1H-pyrazol-3-yl group], [188; 5-difluoromethylthio-4-methyl-1-propyl-1H-pyrazol-3-yl group], [189; 5-difluoromethylthio-4-fluoro-1-propyl-1H-pyrazol-3-yl group], [190; 4-chloro-5-difluoromethylthio-1-propyl-1H-pyrazol-3-yl group], [191; 1-propyl-5-trifluoromethylthio-1H-pyrazol-3-yl group], [192; 4-methyl-1-propyl-5-trifluoromethylthio-1H-pyrazol-3-yl group], [193; 4-fluoro-1-propyl-5-trifluoromethylthio-1H-pyrazol-3-yl group], [194; 4-chloro-1-propyl-5-trifluoromethylthio-1H-pyrazol-3-yl group], [195; 5-cyano-1-propyl-1H-pyrazol-3-yl group], [196; 5-cyano-4-methyl-1-propyl-1H-pyrazol-3-yl group], [197; 5-cyano-4-fluoro-1-propyl-1H-pyrazol-3-yl group], [198; 4-chloro-5-cyano-1-propyl-1H-pyrazol-3-yl group], [199; 1-isopropyl-5-methoxy-1H-pyrazol-3-yl group], [200; 1-isopropyl-5-methoxy-4-methyl-1H-pyrazol-3-yl group], [201; 4-fluoro-1-isopropyl-5-methoxy-1H-pyrazol-3-yl group], [202; 4-chloro-1-isopropyl-5-methoxy-1H-pyrazol-3-yl group], [203; 5-ethoxy-1-isopropyl-1H-pyrazol-3-yl group], [204; 5-ethoxy-1-isopropyl-4-methyl-1H-pyrazol-3-yl group], [205; 5-ethoxy-4-fluoro-1-isopropyl-1H-pyrazol-3-yl group], [206; 4-chloro-5-ethoxy-1-isopropyl-1H-pyrazol-3-yl group], [207; 5-difluoromethoxy-1-isopropyl-1H-pyrazol-3-yl group], [208; 5-difluoromethoxy-1-isopropyl-4-methyl-1H-pyrazol-3-yl group], [209; 5-difluoromethoxy-4-fluoro-1-isopropyl-1H-pyrazol-3-yl group], [210; 4-chloro-5-difluoromethoxy-1-isopropyl-1H-pyrazol-3-yl group]

[substituent number; Q], [211; 1-isopropyl-5-trifluoromethoxy-1H-pyrazol-3-yl group], [212; 4-methyl-1-isopropyl-5-trifluoromethoxy-1H-pyrazol-3-yl group], [213; 4-fluoro-1-isopropyl-5-trifluoromethoxy-1H-pyrazol-3-yl group], [214; 4-chloro-1-isopropyl-5-trifluoromethoxy-1H-pyrazol-3-yl group], [215; 1-isopropyl-5-(2-propynyloxy)-1H-pyrazol-3-yl group], [216; 4-methyl-1-isopropyl-5-(2-propynyloxy)-1H-pyrazol-3-yl group], [217; 4-fluoro-1-isopropyl-5-(2-propynyloxy)-1H-pyrazol-3-yl group], [218; 4-chloro-1-isopropyl-5-(2-propynyloxy)-1H-pyrazol-3-yl group], [219; 1-isopropyl-5-methylthio-1H-pyrazol-3-yl group], [220; 1-isopropyl-5-methylthio-4-methyl-1H-pyrazol-3-yl group], [221; 4-fluoro-1-isopropyl-5-methylthio-1H-pyrazol-3-yl group], [222; 4-chloro-1-isopropyl-5-methylthio-1H-pyrazol-3-yl group], [223; 5-difluoromethylthio-1-isopropyl-1H-pyrazol-3-yl group], [224; 5-difluoromethylthio-1-isopropyl-4-methyl-1H-pyrazol-3-yl group], [225; 5-difluoromethylthio-4-fluoro-1-isopropyl-1H-pyrazol-3-yl group], [226; 4-chloro-5-difluoromethylthio-1-isopropyl-1H-pyrazol-3-yl group], [227; 1-isopropyl-5-trifluoromethylthio-1H-pyrazol-3-yl group], [228; 4-methyl-1-isopropyl-5-trifluoromethylthio-1H-pyrazol-3-yl group], [229; 4-fluoro-1-isopropyl-5-trifluoromethylthio-1H-pyrazol-3-yl group], [230; 4-chloro-1-isopropyl-5-trifluoromethylthio-1H-pyrazol-3-yl group], [231; 5-cyano-1-isopropyl-1H-pyrazol-3-yl group], [232; 5-cyano-1-isopropyl-4-methyl-1H-pyrazol-3-yl group], [233; 5-cyano-4-fluoro-1-isopropyl-1H-pyrazol-3-yl group], [234; 4-chloro-5-cyano-1-isopropyl-1H-pyrazol-3-yl group], [235; 1-difluoromethyl-5-methoxy-1H-pyrazol-3-yl group],

[236; 1-difluoromethyl-5-methoxy-4-methyl-1H-pyrazol-3-yl group], [237; 1-difluoromethyl-4-fluoro-5-methoxy-1H-pyrazol-3-yl group], [238; 4-chloro-1-difluoromethyl-5-methoxy-1H-pyrazol-3-yl group], [239; 1-difluoromethyl-5-ethoxy-1H-pyrazol-3-yl group], [240; 1-difluoromethyl-5-ethoxy-4-methyl-1H-pyrazol-3-yl group]

[substituent number; Q], [241; 1-difluoromethyl-5-ethoxy-4-fluoro-1H-pyrazol-3-yl group], [242; 4-chloro-5-ethoxy-1-difluoromethyl-1H-pyrazol-3-yl group], [243; 5-difluoromethoxy-1-difluoromethyl-1H-pyrazol-3-yl group], [244; 5-difluoromethoxy-1-difluoromethyl-4-methyl-1H-pyrazol-3-yl group], [245; 5-difluoromethoxy-1-difluoromethyl-4-fluoro-1H-pyrazol-3-yl group], [246; 4-chloro-5-difluoromethoxy-1-difluoromethyl-1H-pyrazol-3-yl group], [247; 1-difluoromethyl-5-trifluoromethoxy-1H-pyrazol-3-yl group], [248; 1-difluoromethyl-4-methyl-5-trifluoromethoxy-1H-pyrazol-3-yl group], [249; 1-difluoromethyl-4-fluoro-5-trifluoromethoxy-1H-pyrazol-3-yl group], [250; 4-chloro-1-difluoromethyl-5-trifluoromethoxy-1H-pyrazol-3-yl group], [251; 1-difluoromethyl-5-(2-propynyloxy)-1H-pyrazol-3-yl group], [252; 1-difluoromethyl-4-methyl-5-(2-propynyloxy)-1H-pyrazol-3-yl group], [253; 1-difluoromethyl-4-fluoro-5-(2-propynyloxy)-1H-pyrazol-3-yl group], [254; 4-chloro-1-difluoromethyl-5-(2-propynyloxy)-1H-pyrazol-3-yl group], [255; 1-difluoromethyl-5-methylthio-1H-pyrazol-3-yl group], [256; 1-difluoromethyl-5-methylthio-4-methyl-1H-pyrazol-3-yl group], [257; 1-difluoromethyl-4-fluoro-5-methylthio-1H-pyrazol-3-yl group], [258; 4-chloro-1-difluoromethyl-5-methylthio-1H-pyrazol-3-yl group], [259; 5-difluoromethylthio-1-difluoromethyl-1H-pyrazol-3-yl group], [260; 5-difluoromethylthio-1-difluoromethyl-4-methyl-1H-pyrazol-3-yl group], [261; 5-difluoromethylthio-1-difluoromethyl-4-fluoro-1H-pyrazol-3-yl group], [262; 4-chloro-5-difluoromethylthio-1-difluoromethyl-1H-pyrazol-3-yl group], [263; 5-trifluoromethylthio-1-difluoromethyl-1H-pyrazol-3-yl group], [264; 1-difluoromethyl-4-methyl-5-trifluoromethylthio-1H-pyrazol-3-yl group], [265; 1-difluoromethyl-4-fluoro-5-trifluoromethylthio-1H-pyrazol-3-yl group], [266; 4-chloro-1-difluoromethyl-5-trifluoromethylthio-1H-pyrazol-3-yl group], [267; 5-cyano-1-difluoromethyl-1H-pyrazol-3-yl group], [268; 5-cyano-1-difluoromethyl-4-methyl-1H-pyrazol-3-yl group], [269; 5-cyano-1-difluoromethyl-4-fluoro-1H-pyrazol-3-yl group], [270; 4-chloro-5-cyano-1-difluoromethyl-1H-pyrazol-3-yl group]

[substituent number; Q], [271; 5-methoxy-1-trifluoromethyl-1H-pyrazol-3-yl group], [272; 5-methoxy-4-methyl-1-trifluoromethyl-1H-pyrazol-3-yl group], [273; 4-fluoro-5-methoxy-1-trifluoromethyl-1H-pyrazol-3-yl group], [274; 4-chloro-5-methoxy-1-trifluoromethyl-1H-pyrazol-3-yl group], [275; 5-ethoxy-1-trifluoromethyl-1H-pyrazol-3-yl group], [276; 5-ethoxy-4-methyl-1-trifluoromethyl-1H-pyrazol-3-yl group], [277; 5-ethoxy-4-fluoro-1-trifluoromethyl-1H-pyrazol-3-yl group], [278; 4-chloro-5-ethoxy-1-trifluoromethyl-1H-pyrazol-3-yl group], [279; 5-difluoromethoxy-1-trifluoromethyl-1H-pyrazol-3-yl group], [280; 5-difluoromethoxy-4-methyl-1-trifluoromethyl-1H-pyrazol-3-yl group], [281; 5-difluoromethoxy-4-fluoro-1-trifluoromethyl-1H-pyrazol-3-yl group], [282; 4-chloro-5-difluoromethoxy-1-trifluoromethyl-1H-pyrazol-3-yl group], [283; 5-trifluoromethoxy-1-trifluoromethyl-1H-pyrazol-3-yl group], [284; 4-methyl-5-trifluoromethoxy-1-trifluoromethyl-1H-pyrazol-3-yl group], [285; 4-fluoro-5-trifluoromethoxy-1-trifluoromethyl-1H-pyrazol-3-yl group], [286; 4-chloro-5-trifluoromethoxy-1-trifluoromethyl-1H-pyrazol-3-yl group], [287; 5-(2-propynyloxy)-1-trifluoromethyl-1H-pyrazol-3-yl group], [288; 4-methyl-5-(2-propynyloxy)-1-trifluoromethyl-1H-pyrazol-3-yl group], [289; 4-fluoro-5-(2-propynyloxy)-1H-pyrazole-1-trifluoromethyl-3-yl group], [290; 4-chloro-5-(2-propynyloxy)-1-trifluoromethyl-1H-pyrazol-3-yl group], [291; 5-methylthio-1-trifluoromethyl-1H-pyrazol-3-yl group], [292; 5-methylthio-4-methyl-1-trifluoromethyl-1H-pyrazol-3-yl group], [293; 4-fluoro-5-methylthio-1-trifluoromethyl-1H-pyrazol-3-yl group], [294; 4-chloro-5-methylthio-1-trifluoromethyl-1H-pyrazol-3-yl group], [295; 5-difluoromethylthio-1-trifluoromethyl-1H-pyrazol-3-yl group], [296; 5-difluoromethylthio-4-methyl-1-trifluoromethyl-1H-pyrazol-3-yl group], [297; 5-difluoromethylthio-4-fluoro-1-trifluoromethyl-1H-pyrazol-3-yl group], [298; 4-chloro-5-difluoromethylthio-1-trifluoromethyl-1H-pyrazol-3-yl group], [299; 5-trifluoromethylthio-1-trifluoromethyl-1H-pyrazol-3-yl group], [300; 4-methyl-5-trifluoromethylthio-1-trifluoromethyl-1H-pyrazol-3-yl group]

[substituent number; Q], [301; 4-fluoro-5-trifluoromethylthio-1-trifluoromethyl-1H-pyrazol-3-yl group], [302; 4-chloro-5-trifluoromethylthio-1-trifluoromethyl-1H-pyrazol-3-yl group], [303; 5-cyano-1-trifluoromethyl-1H-pyrazol-3-yl group], [304; 5-cyano-4-methyl-1-trifluoromethyl-1H-pyrazol-3-yl group], [305; 5-cyano-4-fluoro-1-trifluoromethyl-1H-pyrazol-3-yl group], [306; 4-chloro-5-cyano-1-trifluoromethyl-1H-pyrazol-3-yl group], [307; 1-(2,2-difluoroethyl)-5-methoxy-1H-pyrazol-3-yl group], [308; 1-(2,2-difluoroethyl)-5-methoxy-4-methyl-1H-pyrazol-3-yl group], [309; 1-(2,2-difluoroethyl)-4-fluoro-5-methoxy-1H-pyrazol-3-yl group], [310; 4-chloro-1-(2,2-difluoroethyl)-5-methoxy-1H-pyrazol-3-yl group], [311; 1-(2,2-difluoroethyl)-5-ethoxy-1H-pyrazol-3-yl group], [312; 1-(2,2-difluoroethyl)-5-ethoxy-4-methyl-1H-pyrazol-3-yl group], [313; 1-(2,2-difluoroethyl)-5-ethoxy-4-fluoro-1H-pyrazol-3-yl group], [314; 4-chloro-5-ethoxy-1-(2,2-difluoroethyl)-1H-pyrazol-3-yl group], [315; 5-difluoromethoxy-1-(2,2-difluoroethyl)-1H-pyrazol-3-yl group], [316; 5-difluoromethoxy-1-(2,2-difluoroethyl)-4-methyl-1H-pyrazol-3-yl group], [317; 5-difluoromethoxy-1-(2,2-difluoroethyl)-4-fluoro-1H-pyrazol-3-yl group], [318; 4-chloro-5-difluoromethoxy-1-(2,2-difluoroethyl)-1H-pyrazol-3-yl group], [319; 1-(2,2-difluoroethyl)-5-trifluoromethoxy-1H-pyrazol-3-yl group], [320; 1-(2,2-difluoroethyl)-4-methyl-5-trifluoromethoxy-1H-pyrazol-3-yl group], [321; 1-(2,2-difluoroethyl)-4-fluoro-5-trifluoromethoxy-1H-pyrazol-3-yl group], [322; 4-chloro-1-(2,2-difluoroethyl)-5-trifluoromethoxy-1H-pyrazol-3-yl group], [323; 1-(2,2-difluoroethyl)-5-(2-propynyloxy)-1H-pyrazol-3-yl group], [324; 1-(2,2-difluoroethyl)-4-methyl-5-(2-propynyloxy)-1H-pyrazol-3-yl group], [325; 1-(2,2-difluoroethyl)-4-fluoro-5-(2-propynyloxy)-1H-pyrazol-3-yl group], [326; 4-chloro-1-(2,2-difluoroethyl)-5-(2-propynyloxy)-1H-pyrazol-3-yl group], [327; 1-(2,2-difluoroethyl)-5-methylthio-1H-pyrazol-3-yl group], [328; 1-(2,2-difluoroethyl)-5-methylthio-4-methyl-1H-pyrazol-3-yl group], [329; 1-(2,2-difluoroethyl)-4-fluoro-5-methylthio-1H-pyrazol-3-yl group], [330; 4-chloro-1-(2,2-difluoroethyl)-5-methylthio-1H-pyrazol-3-yl group]

[substituent number; Q], [331; 5-difluoromethylthio-1-(2,2-difluoroethyl)-1H-pyrazol-3-yl group], [332; 5-difluoromethylthio-1-(2,2-difluoroethyl)-4-methyl-1H-pyrazol-3-yl group], [333; 5-difluoromethylthio-1-(2,2-difluoroethyl)-4-fluoro-1H-pyrazol-3-yl group], [334; 4-chloro-5-difluoromethylthio-1-(2,2-difluoroethyl)-1H-pyrazol-3-yl group], [335; 5-trifluoromethylthio-1-(2,2-difluoroethyl)-1H-pyrazol-3-yl group], [336; 1-(2,2-difluoroethyl)-4-methyl-5-trifluoromethylthio-1H-pyrazol-3-yl group], [337; 1-(2,2-difluoroethyl)-4-fluoro-5-trifluoromethylthio-1H-pyrazol-3-yl group], [338; chloro-1-(2,2-difluoroethyl)-5-trifluoromethylthio-1H-pyrazol-3-yl group], [339; 5-cyano-1-(2,2-difluoroethyl)-1H-pyrazol-3-yl group], [340; 5-cyano-1-(2,2-difluoroethyl)-4-methyl-1H-pyrazol-3-yl group], [341; 5-cyano-1-(2,2-difluoroethyl)-4-fluoro-1H-pyrazol-3-yl group], [342; 4-chloro-5-cyano-1-(2,2-difluoroethyl)-1H-pyrazol-3-yl group]

In accordance with the above method, it is possible to obtain compounds EB1A-001 to EG1N-342.

The compounds EB1A-001 to EG1N-342 are compounds represented by the following formulas:

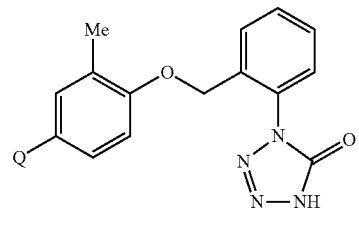
(EB1A)

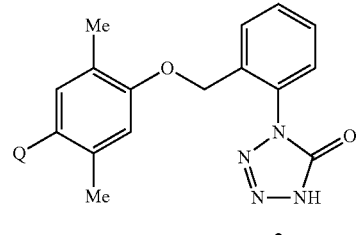
(EB1B)

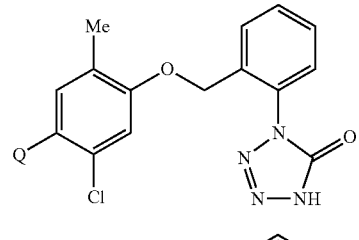
(EB1C)

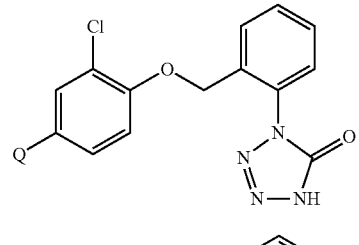
(EB1D)

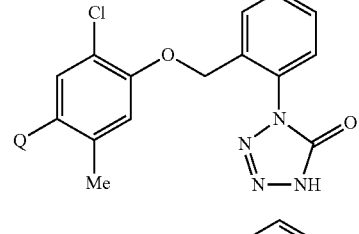
(EB1E)

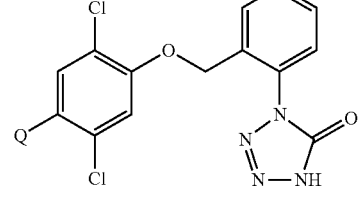
(EB1F)

-continued

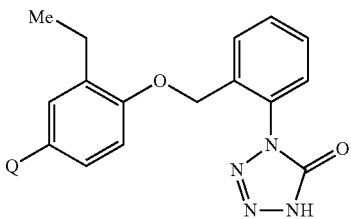
(EB1G)

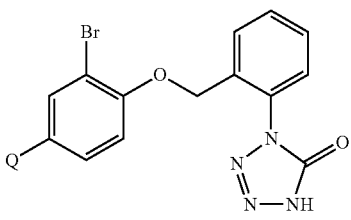
(EB1H)

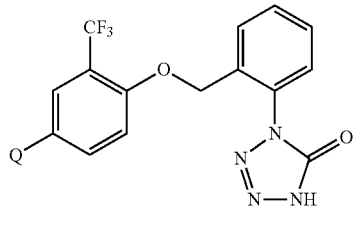
(EB1I)

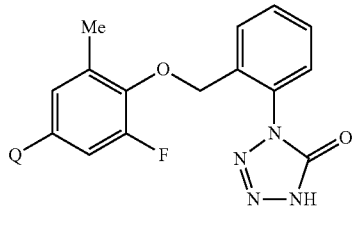
(EB1J)

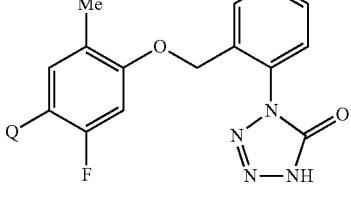
(EB1K)

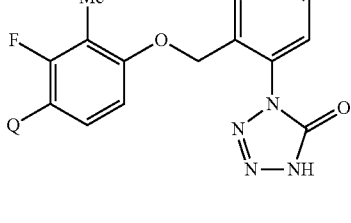
(EB1L)

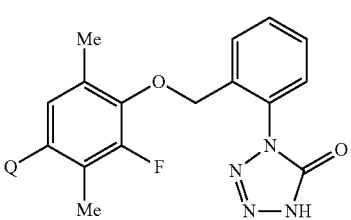
(EB1M)

-continued (EB1N)

(EC1A)

(EC1B)

(EC1C)

(EC1D)

(EC1E)

(EC1F)

(EC1G)

-continued (EC1H)

(EC1I)

(EC1J)

(EC1K)

(EC1L)

(EC1M)

(EC1N)

(ED1A)

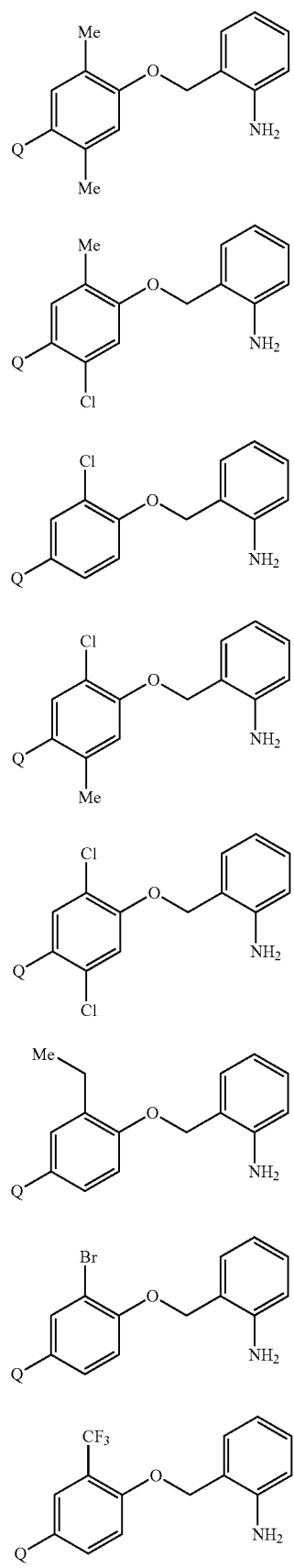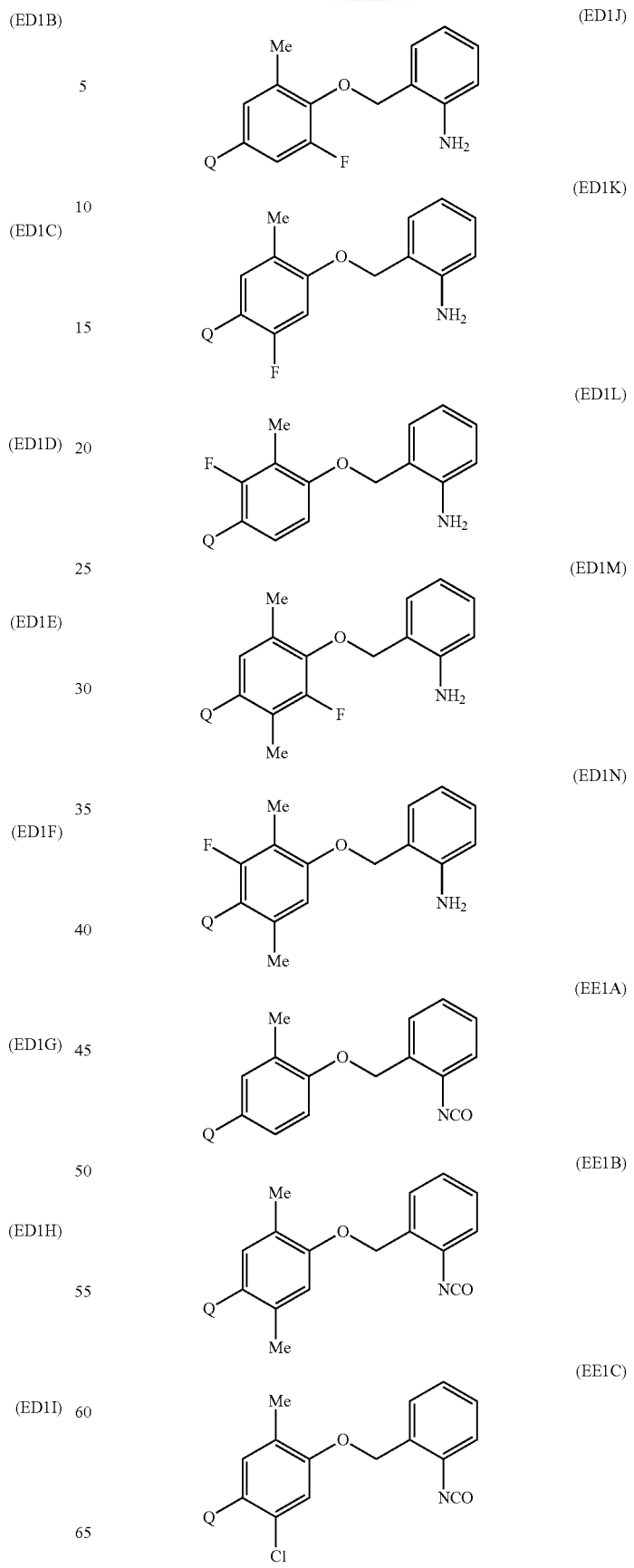

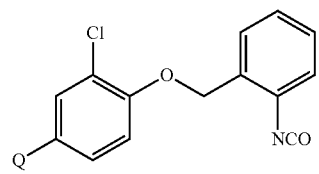 (EE1D)
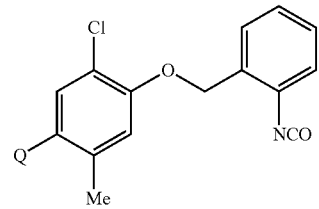 (EE1E)
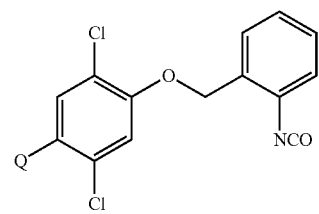 (EE1F)
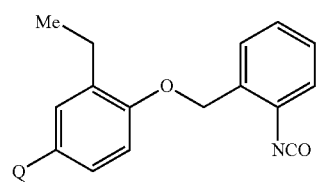 (EE1G)
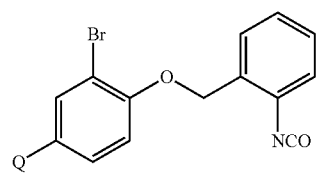 (EE1H)
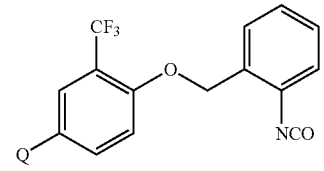 (EE1I)
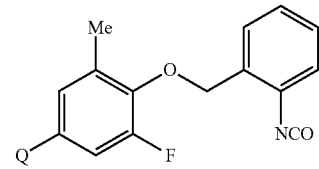 (EE1J)
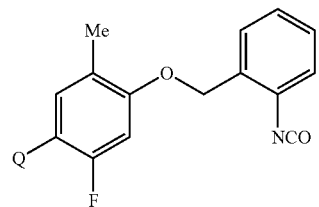 (EE1K)
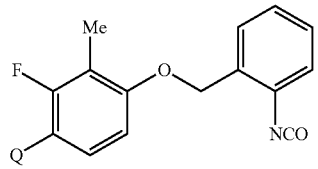 (EE1L)
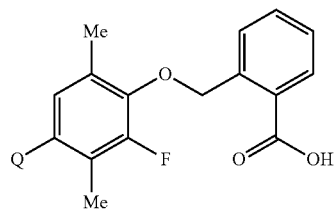 (EF1M)
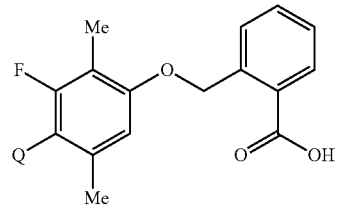 (EF1N)
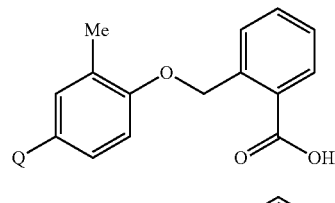 (EF1A)
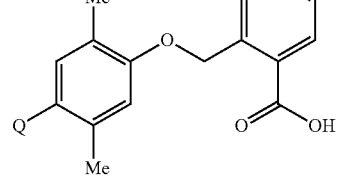 (EF1B)
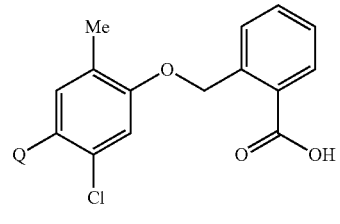 (EF1C)
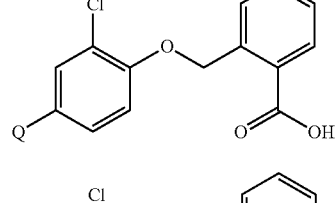 (EF1D)
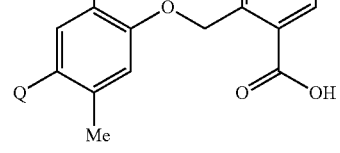 (EF1E)

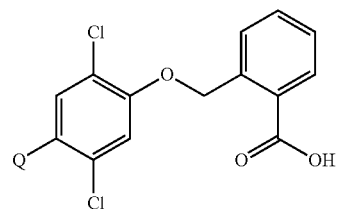
(EF1F)
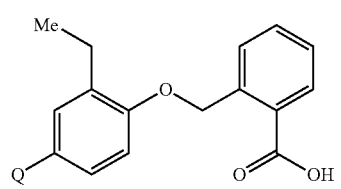
(EF1G)
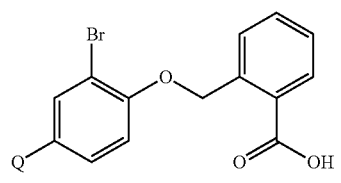
(EF1H)
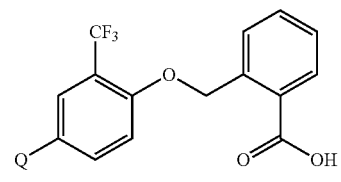
(EF1I)
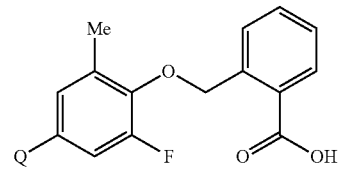
(EF1J)
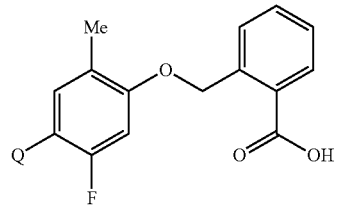
(EF1K)
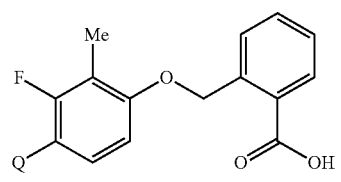
(EF1L)
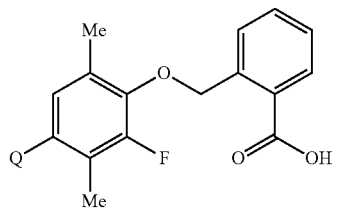
(EF1M)
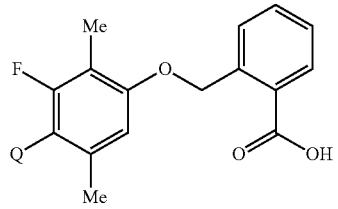
(EF1N)
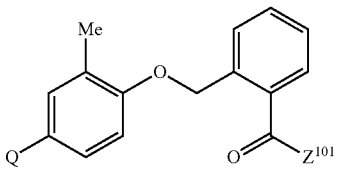
(EG1A)
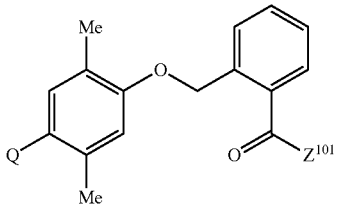
(EG1B)
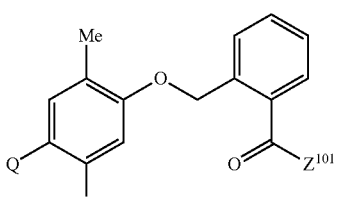
(EG1C)
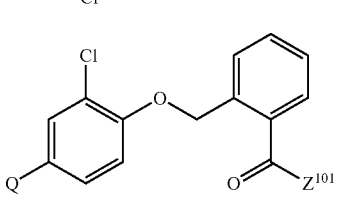
(EG1D)
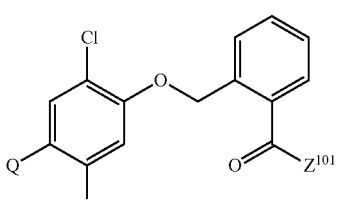
(EG1E)
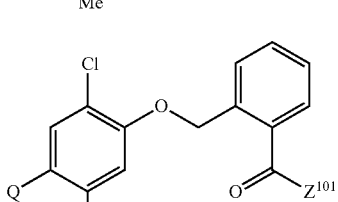
(EG1F)
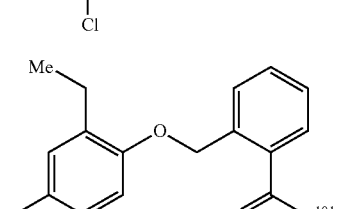
(EG1G)

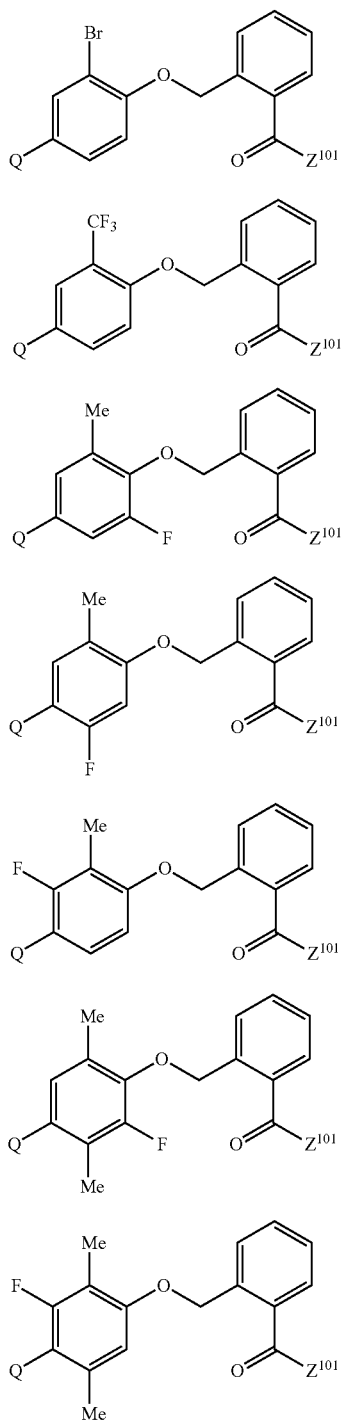

wherein $Z^{101}$ is the same as defined above, and Q represents a substituent corresponding to each of substituent numbers 1 to 342.

Formulation Examples will be shown below. Parts are by weight.

Formulation Example 1

Fifty parts (50 parts) of any one of the present compounds 1 to 10, 3 parts of calcium ligninsulfoate, 2 parts of lauryl- magnesium sulfate, and 45 parts of synthetic hydrated silicon oxide are thoroughly ground and mixed to obtain each formulation.

Formulation Example 2

Twenty parts (20 parts) of any one of the present compounds 1 to 10 and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds 1 to 10, 88 parts of kaolin clay, and 10 parts of talc are thoroughly ground and mixed to obtain each formulation.

Formulation Example 4

Five parts (5 parts) of any one of the present compounds 1 to 10, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds 1 to 10, 1 part of synthetic hydrated silicon oxide, 2 parts of calcium ligninsulfoate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds 1 to 10, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling pests.

The control effect was evaluated by visually observing the area of lesion spots on each of test plants at the time of investigation, and comparing the area of lesion spots on a plant treated with the present control agent with that on an untreated plant. The untreated plant is a plant tested under the same conditions as in Test Examples, except that foliage application of a diluted solution of a formulation containing the present compound with water is not performed.

Test Example 1

Each of plastic pots was filled with sandy loam and rice (cultivar: NIHONBARE) was sowed and grown in a greenhouse for 20 days. Each of the present compounds 1 to 8, 11, and 12 was diluted with water to adjust to a predetermined concentration of 500 ppm. The obtained diluted solutions were sprayed over stems and leaves so that they sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compounds 1 to 8, 11, and 12 were 30% or less with respect to the lesion area on the non-treated plant.

Test Example 2

Each of plastic pots was filled with sandy loam and wheat (cultivar: SHIROGANE) was sowed and grown in a greenhouse for 9 days. Each of the present compounds 1 to 5, 11, and 1 was diluted with water to adjust to a predetermined concentration of 500 ppm. The obtained diluted solution was sprayed over stems and leaves of the wheat so that they sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with each of the present compounds 1 to 5, 11, and 12 was 30% or less of that on an untreated plant.

Test Example 3

Each of plastic pots was filled with sandy loam and barley (cultivar: MIKAMO GOLDEN) was sowed and grown in a greenhouse for 7 days. Each of the present compounds 1 to 8, 10 to 12, and 14 was diluted with water to adjust to a predetermined concentration of 500 ppm. The obtained diluted solution was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on the plant treated with 1 to 8, 10 to 12, and 14 was 30% or less of that on an untreated plant.

Test Example 4

Each of plastic pots was filled with sandy loam and kidney bean (cultivar: NAGAUZURA INNGEN) was sowed and grown in a greenhouse for 8 days. Each of the present compounds 1 to 4, 11, and 14 was diluted with water to adjust to a predetermined concentration of 500 ppm. The obtained diluted solution was sprayed over stems and leaves of the kidney bean so that they sufficiently adhered to the surface of the leaves of the kidney bean. After spraying, the plant was air-dried and a PDA medium containing hyphae of kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with any one of the present compounds 1 to 4, 11, and 14 was 30% or less of that on an untreated plant.

Test Example 5

Each of plastic pots was filled with sandy loam and wheat (cultivar: APOGEE) was sowed and grown in a greenhouse for 10 days. Each of the present compounds 1 to 8, 11, 12, and 14 was diluted with water to adjust to a predetermined concentration of 500 ppm. The obtained diluted solution was sprayed over stems and leaves of the wheat so that they sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with each of the present compounds 1 to 8, 11, 12, and 14 was 30% or less of that on an untreated plant.

Test Example 6

Each of plastic pots was filled with sandy loam and cucumber (cultivar: SAGAMI HANJIRO) was sowed and grown in a greenhouse for 12 days. Each of the present compounds 1 to 8, and 14 was diluted with water to adjust to a predetermined concentration of 500 ppm. The obtained diluted solution was sprayed over stems and leaves of the cucumber so that they sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with each of the present compounds 1 to 8, and 14 was 30% or less of that on an untreated plant.

Test Example 7

Each of plastic pots was filled with sandy loam and rice (cultivar: NIHONBARE) was sowed and grown in a greenhouse for 20 days. Each of the present compounds 1 to 12, and 14 was diluted with water to adjust to a predetermined concentration of 200 ppm. The obtained diluted solutions were sprayed over stems and leaves so that they sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compounds 1 to 12, and 14 were 30% or less with respect to the lesion area on the non-treated plant.

Test Example 8

Each of plastic pots was filled with sandy loam and wheat (cultivar: SHIROGANE) was sowed and grown in a greenhouse for 9 days. Each of the present compounds 1 to 12, and 14 was diluted with water to adjust to a predetermined concentration of 200 ppm. The obtained diluted solution was sprayed over stems and leaves of the wheat so that they sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with each of the present compounds 1 to 12, and 14 was 30% or less of that on an untreated plant.

Test Example 9

Each of plastic pots was filled with sandy loam and barley (cultivar: MIKAMO GOLDEN) was sowed and grown in a greenhouse for 7 days. Each of the present compounds 1 to 12, and 14 was diluted with water to adjust to a predetermined concentration of 200 ppm. The obtained diluted solution was sprayed over stems and leaves of the barley so that they sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with each of the present compounds 1 to 12, and 14 was 30% or less of that on an untreated plant.

Test Example 10

Each of plastic pots was filled with sandy loam and kidney bean (cultivar: NAGAUZURA INNGEN) was sowed and grown in a greenhouse for 8 days. Each of the present compounds 1 to 6, 8, and 9 was diluted with water to adjust to a predetermined concentration of 200 ppm. The obtained diluted solution was sprayed over stems and leaves of the kidney bean so that they sufficiently adhered to the surface of the leaves of the kidney bean. After spraying, the plant was air-dried and a PDA medium containing hyphae of kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with any one of the present compounds 1 to 6, 8, and 9 was 30% or less of that on an untreated plant.

Test Example 11

Each of plastic pots was filled with sandy loam and wheat (cultivar: APOGEE) was sowed and grown in a greenhouse for 10 days. Each of the present compounds 1 to 8, and 9 was diluted with water to adjust to a predetermined concentration of 200 ppm. The obtained diluted solution was sprayed over stems and leaves of the wheat so that they sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with each of the present compounds 1 to 8, and was 30% or less of that on an untreated plant.

Test Example 12

Each of plastic pots was filled with sandy loam and cucumber (cultivar: SAGAMI HANJIRO) was sowed and grown in a greenhouse for 12 days. Each of the present compounds 1 to 9, 11, and 12 was diluted with water to adjust to a predetermined concentration of 200 ppm. The obtained diluted solution was sprayed over stems and leaves of the cucumber so that they sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with each of the present compounds 1 to 9, 11, and 12 was 30% or less of that on an untreated plant.

Test Example 13

Each of plastic pots was filled with sandy loam and soybean (cultivar: KUROSENGOKU) was sowed and grown in a greenhouse for 13 days. Each of the present compounds 1, 2, 4, 5, 8, 9, 11, and 12 was diluted with water to adjust to a predetermined concentration of 200 ppm. The obtained diluted solution was sprayed over stems and leaves of the soybean so that they sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was left to stand for 3 days in a greenhouse at 23° C. in the daytime and 20° C. at night under high humidity condition and cultivated in a greenhouse for 14 days, and then the area of lesion spots was investigated. As a result, it has been found that the area of lesion spots on the plant treated with each of the present compounds 1, 2, 4, 5, 8, 9, 11, and 12 was 30% or less of that on an untreated plant.

Test Example 14

Each of plastic pots was filled with sandy loam and barley (cultivar: MIKAMO GOLDEN) was sowed and grown in a greenhouse for 7 days. Each of the present compounds 1 to 9, 11, 12, and 14 was diluted with water to adjust to a predetermined concentration of 200 ppm. The obtained diluted solution was sprayed over stems and leaves of the barley so that they sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on the plant treated with each of the present compounds 1 to 9, 11, 12, and 14 was 30% or less of that on an untreated plant.

Test Example 15

Each of plastic pots was filled with sandy loam and cucumber (cultivar: SAGAMI HANJIRO) was sowed and grown in a greenhouse for 19 days. Each of the present compounds 1 to 4, 8, 9, 11, 12, and 14 was diluted with water to adjust to a predetermined concentration of 200 ppm. The obtained diluted solution was sprayed over stems and leaves of the cucumber so that they sufficiently adhered to the surface of the leaves of the cucumber. After spraying, the plant was air-dried. After one day, the plant was inoculated by sprinkling with spores of cucumber *corynespora* leaf spot fungus (*Corynespora cassicola*). After the inoculation, the plant was cultivated in a greenhouse at 24° C. in the daytime and 20° C. at night for 7 days, and then the area of lesion spots was investigated. As a result, the area of lesion spots on the plant treated with each of the present compounds 1 to 4, 8, 9, 11, 12, and 14 was 30% or less of that on an untreated plant.

Test Example 16

Each of plastic pots was filled with sandy loam and cucumber (cultivar: SAGAMI HANJIRO) was sowed and grown in a greenhouse for 19 days. Each of the present compounds 1 to 6, 8, 9, 11, 12, and 14 was diluted with water to adjust to a predetermined concentration of 200 ppm. The obtained diluted solution was sprayed over stems and leaves of the cucumber so that they sufficiently adhered to the surface of the leaves of the cucumber. After spraying, the plant was air-dried. After one day, the plant was inoculated by sprinkling with spores of cucumber anthracnose fungus (*Colletotrichum lagenarium*). After the inoculation, the plant was at first left to stand at 23° C. under high humidity condition for one day and then cultivated in a greenhouse at 24° C. in the daytime and 20° C. at night for 6 days. Thereafter, the area of lesion spots was investigated. As a result, the area of lesion spots on the plant treated with each of the present compounds 1 to 6, 8, 9, 11, 12, and 14 was 30% or less of that on an untreated plant.

Comparative Test Example

Each of plastic pots was filled with sandy loam and wheat (cultivar: SHIROGANE) was sowed and grown in a greenhouse for 9 days. Each of 1-{2-[2-Methyl-4-(1,5-dimethyl-1H-pyrazol-3-yl)phenoxymethyl]phenyl}-4-methyl-1,4-dihydrotetrazol-5-one and 1-{2-[2-methyl-4-(4-chloro-1,5-dimethyl-1H-pyrazol-3-yl)phenoxymethyl]phenyl}-4-methyl-1,4-dihydrotetrazol-5-one was diluted with water to adjust to a predetermined concentration of 500 ppm. The obtained diluted solution was sprayed over stems and leaves of the wheat so that they sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with each of 1-{2-[2-Methyl-4-(1,5-dimethyl-1H-pyrazol-3-yl)phenoxymethyl]phenyl}-4-methyl-1,4-dihydrotetrazol-5-one and 1-{2-[2-methyl-4-(4-chloro-1,5-dimethyl-1H-pyrazol-3-yl)phenoxymethyl]phenyl}-4-methyl-1,4-dihydrotetrazol-5-one was 70% or more of that on an untreated plant.

The invention claimed is:

1. A tetrazolinone compound represented by formula (1):

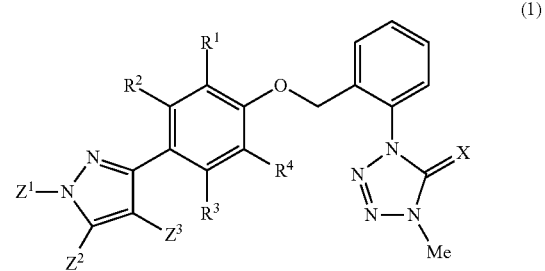

wherein
$R^1$ represents a C1-C3 alkyl group optionally having a fluorine atom, or a halogen atom;
$R^2$ and $R^4$ each independently represents a hydrogen atom or a fluorine atom;
$R^3$ represents a hydrogen atom, a C1-C3 alkyl group, or a halogen atom;
$Z^1$ represents a C1-C3 alkyl group optionally having a halogen atom;
$Z^2$ represents a C1-C3 alkoxy group optionally having a halogen atom, a C3-C4 alkynyloxy group optionally having a halogen atom, a C1-C3 alkylthio group optionally having a halogen atom, a C2-C4 dialkylamino group, or a cyano group;
$Z^3$ represents a hydrogen atom, a C1-C3 alkyl group optionally having a halogen atom, a halogen atom, or a cyano group; and
X represents an oxygen atom or a sulfur atom.

2. The tetrazolinone compound according to claim 1, wherein $R^1$ is a C1-C3 alkyl group or a halogen atom;
$R^2$ and $R^4$ are hydrogen atoms;
$R^3$ is a hydrogen atom, a C1-C3 alkyl group, or a halogen atom;
$Z^1$ is a C1-C3 alkyl group;
$Z^2$ is a cyano group, a C1-C3 alkoxy group, or a C1-C3 alkylthio group;
$Z^3$ is a C1-C3 alkyl group or a halogen atom; and
X is an oxygen atom.

3. The tetrazolinone compound according to claim 1, wherein $R^1$ is a C1-C3 alkyl group;
$R^2$, $R^3$, and $R^4$ are hydrogen atoms;
$Z^1$ is a C1-C3 alkyl group;
$Z^2$ is a cyano group;
$Z^3$ is a C1-C3 alkyl group; and
X is an oxygen atom.

4. A pest control agent comprising the tetrazolinone compound according to claim 1.

5. A method for controlling pests, which comprises treating plants or soil with an effective amount of the tetrazolinone compound according to claim 1.

* * * * *